United States Patent [19]
Joliff et al.

[11] Patent Number: 6,027,920
[45] Date of Patent: Feb. 22, 2000

[54] SYSTEM FOR PROTEIN EXPRESSION AND SECRETION ESPECIALLY IN CORYNEBACTERIA

[75] Inventors: Gwennaël Joliff, Paris; Armel Guyonvarch, L'Hay les Roses; Purification Relano, Fontenay Aux Roses; Gérard Leblon, Les Ulis; Francis Duchiron, Avon; Michel Renaud, Les Ulis, all of France

[73] Assignee: Orsan, Paris, France

[21] Appl. No.: 08/508,761

[22] Filed: Jul. 31, 1995

Related U.S. Application Data

[63] Continuation of application No. 08/039,028, filed as application No. PCT/FR92/00744, Jul. 29, 1992, abandoned.

[30] Foreign Application Priority Data

Jul. 30, 1991 [FR] France ................................... 91/09652
Aug. 2, 1991 [FR] France ................................... 91/09870

[51] Int. Cl.[7] ............................. C07K 14/34; C12N 1/21; C12N 15/77; C12P 21/02
[52] U.S. Cl. ................... 435/69.7; 435/69.8; 435/252.3; 435/252.32; 435/320.1; 530/350; 530/387.1; 536/23.4; 536/23.7
[58] Field of Search ................................... 435/69.1, 69.7, 435/252.3, 252.32, 320.1, 69.8; 530/350, 387.1; 536/23.1, 23.2, 23.4, 23.7

[56] References Cited

U.S. PATENT DOCUMENTS 4,965,197  10/1990  Liebl et al. ............................. 435/69.8

FOREIGN PATENT DOCUMENTS 2575492  7/1986  France .
8809821  12/1988  WIPO .

OTHER PUBLICATIONS

Wilkins Bergey's Manual of Systematic Bacteriology vol. 2 pp. 1261–1434.

M.–A. Petit et al., "Hypersecretion of a cellulase from *clostridium thermocellum* in *bacillus subtilis* by induction of chromosomal dna amplification", Bio/Technology, vol. 8, No. 6, Jun. 1990.

Figure 11:
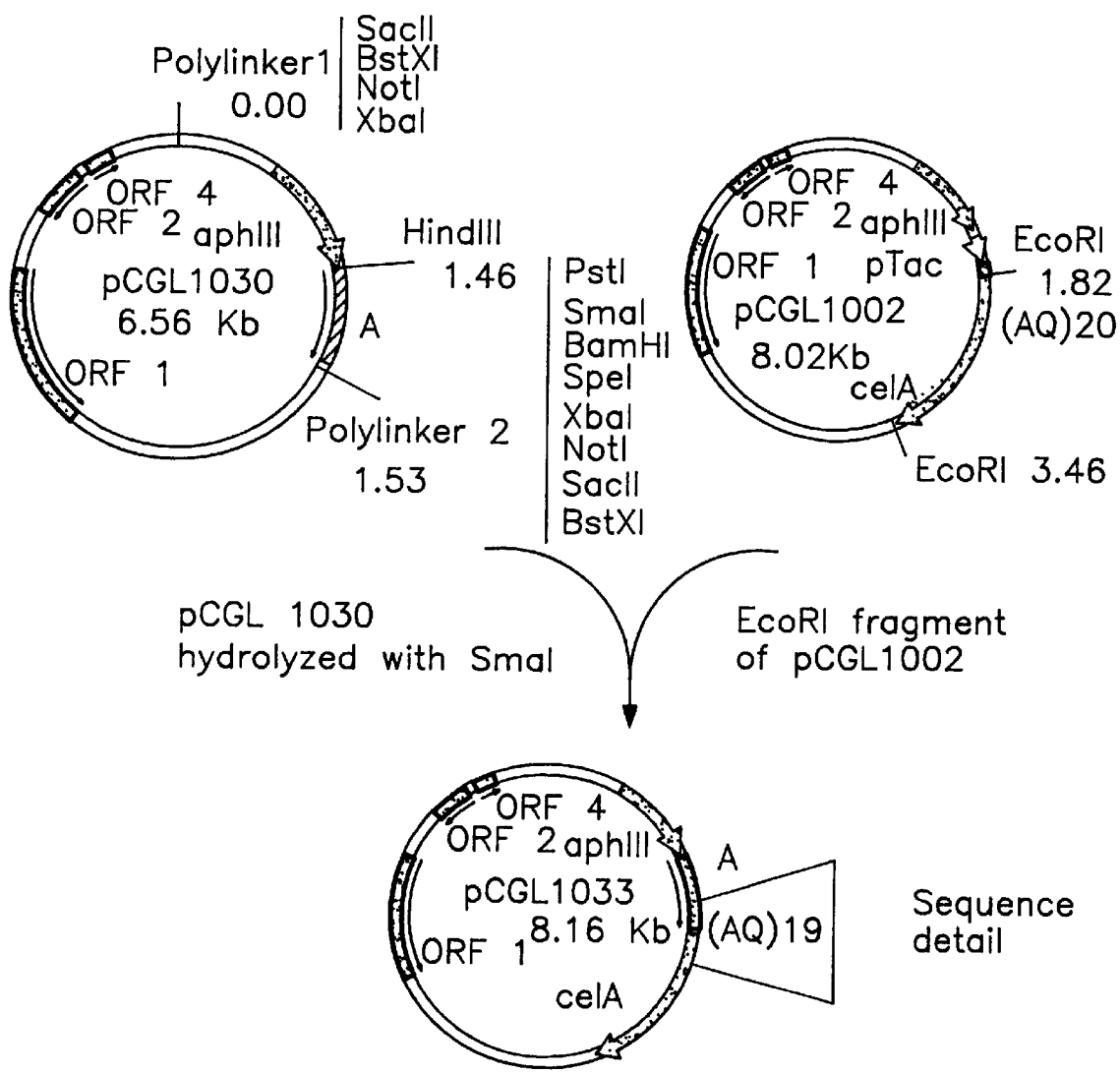

PROMEGA product catalogue 1990/91 published by PROMEGA Corporation, Madison, Wisconsin, USA, pp. 10, Fig. 2A, 11, Table 2A, 72–73, and 76–77.

Patent Abstracts of Japan, vol. 13, No. 3 (C–557) (3351) Jan. 6, 1989 & JP–A–63 214 189 (Asahi Chem Ind Co Ltd).

Database WPIL, Derwent Publications Ltd., London, GB; Accession No. 91–310282, DW9142 & US–A–7560035 (Nat Inst of Health), Oct. 09, 1991.

Y. Morinaga et al., "Expression of *Escherichia coli* promoters in *Brevibacterium lactofermentum* using the shuttle vector pEB003", J. Biotechnology, vol. 5, No. 4, May 5, 1987, pp. 305–312.

A. Schwarzer et al., "Manipulation of *Corynebacterium Glutamicum* by Gene Disruption & Replacement", Bio/Technology, vol. 9, No. 1, Jan. 1991, pp. 84–87, Nature America, Inc.

*Primary Examiner*—George C. Elliott
*Assistant Examiner*—Robert Schwartzman
*Attorney, Agent, or Firm*—Jacobson, Price, Holman & Stern, PLLC

[57] ABSTRACT

A DNA cassette for expression and secretion of a given amino acid, polypeptide or protein in a host strain of corynebacterium, including a sequence which encodes the amino acid, polypeptide or protein, and a region of chromosomal or plasmid DNA, wherein the sequence is situated in the region of chromosomal or plasmid DNA such that the sequence is transcribed with, at the sequence's 5' end, at least one portion of a sequence encoding the signal sequence of the protein PS1 or PS2, the at least one portion ensuring the secretion of the amino acid, polypeptide or protein after translation when the DNA cassette is incorporated into the host strain of corynebacterium.

28 Claims, 31 Drawing Sheets

FIG. 2A (1st plate)

```
AAGCTTCAAGGGGAAAACAAGGGCCTT AAAAGTTATCCACAG ATCCGAAGTG    52
ATCCGCGCACTGGGGTG AAAAGTTATCCACAG GAAGCGGAGGGGCGG ATTGA  104
AAAA TTCAGCGAAATGCGAAAAGGTGGAGGGGAAATGCTGCGAGTCTTGCGG    156
ATTCCCGGCGTGGC ATTGAAAAA AGTCTAAAGTTGAACTTAAGATTGAGGTC   208
ATTCTGAAGTTGTGACCTGCATCAGAAGAGTTACATACCCACATATGTAACC    260
TTCTGGACTAAGATCACGACAGACTGAAAAGAACTGAAGACTCTCAAGGCAT    312
AGCCCACGTGTGTTTGTCGGGCCGGAAGCGGGGAACTTTCGGGACGGATCTA    364
ACTCATTGCGGGCCTGTGCGCAGTATCCAAAAATCAAAATGAGAAGGAAAAC    416
```

```
TTC ATG CGC GAC ACC GCA TTT CGT TCC ATC AAG GCT AAA    455
    Met Arg Asp Thr Ala Phe Arg Ser Ile Lys Ala Lys
GCT CAG GCT AAG CGC CGT TCC CTC TGG ATT GCA GCA GGC    494
Ala Gln Ala Lys Arg Arg Ser Leu Trp Ile Ala Ala Gly
GCT GTC CCA ACC GCA ATT GCG TTG ACT ATG TCC CTG GCA    533
Ala Val Pro Thr Ala Ile Ala Leu Thr Met Ser Leu Ala
CCT ATG GCT TCG GCT CAG TCC AGC AAC CTT TCC TCT GAT    572
Pro Met Ala Ser Ala Gln Ser Ser Asn Leu Ser Ser Asp
GCC GTA GTT GGC AGC ATC GCG CAG GGC GTC ACC GAT GGC    611
Ala Val Val Gly Ser Ile Ala Gln Gly Val Thr Asp Gly
CTG ACT GAC TAC CTG AAG CCT CGC GTC GAA GAG CTT CCT    650
Leu Thr Asp Tyr Leu Lys Pro Arg Val Glu Glu Leu Pro
GCT GGT GAA GTC ACC TAC CCA GAG ATC GCC GGG CTG CCT    689
Ala Gly Glu Val Thr Tyr Pro Glu Ile Ala Gly Leu Pro
GAT GGT GTG CGC GTG ATC AGC GCT GAG TGG GCA ACC TCC    728
Asp Gly Val Arg Val Ile Ser Ala Glu Trp Ala Thr Ser
AAG CAT GTC ATT TTG ACT ATT CAG TCT GCA GCA ATG CCA    767
Lys His Val Ile Leu Thr Ile Gln Ser Ala Ala Met Pro
GAG CGC CCA ATC AAG GTC CAG CTG CTG CTT CCG CGT GAC    806
Glu Arg Pro Ile Lys Val Gln Leu Leu Leu Pro Arg Asp
TGG TAC TCT TCC CCG AAC CGT GAG TTC CCT GAA ATC TGG    845
Trp Tyr Ser Ser Pro Asn Arg Glu Phe Pro Glu Ile Trp
GCA CTT GAC GGT CTG CGC CGC ATT GAA GAG CAG AGT GGT    884
Ala Leu Asp Gly Leu Arg Arg Ile Glu Glu Gln Ser Gly
```

FIG. 2B (2nd plate)

```
TGG ACC ATT GAG ACC AAC ATT GAG CAG TAC TAC GCC GAT    923
Trp Thr Ile Glu Thr Asn Ile Glu Gln Tyr Tyr Ala Asp

AAG AAC GCC ATT GTT GTG CTC CCA ATC GGT GGC GAG AGC    962
Lys Asn Ala Ile Val Val Leu Pro Ile Gly Gly Glu Ser

TCC TTC TAC TCT GAC TGG GAA GAG CCA AAC AAC GGC AAG   1001
Ser Phe Tyr Ser Asp Trp Glu Glu Pro Asn Asn Gly Lys

AAC TAC CAG TGG GAG ACC TTC CTG ACT CAG GAG CTC GCA   1040
Asn Tyr Gln Trp Glu Thr Phe Leu Thr Gln Glu Leu Ala

CCG ATC CTG GAC AAG GGC TTC CGT TCC AAC ACC GAT CGC   1079
Pro Ile Leu Asp Lys Gly Phe Arg Ser Asn Thr Asp Arg

GCC ATC ACC GGT ATC TCC ATG GGC GGT ACC GCT GCG GTT   1118
Ala Ile Thr Gly Ile Ser Met Gly Gly Thr Ala Ala Val

ACC ATC GCA ACC CAC CAC CCA GAC ATG TTT AAG TTC GTC   1157
Asn Ile Ala Thr His His Pro Asp Met Phe Lys Phe Val

GGT TCC TTC TCC GGC TAT CTG GAC ACC ACC TCC GCT GGC   1196
Gly Ser Phe Ser Gly Tyr Leu Asp Thr Thr Ser Ala Gly

ATG CCA ATC GCT ATT TCC GCA GCC CTG GCA GAC GCC GGC   1235
Met Pro Ile Ala Ile Ser Ala Ala Leu Ala Asp Ala Gly

GGA TAC GAT GCC AAC GCA ATG TGG GGA CCA GTC GGT TCT   1274
Gly Tyr Asp Ala Asn Ala Met Trp Gly Pro Val Gly Ser

GAG CGC TGG CAG GAA AAC GAT CCA AAG AGC ACC GTA GAC   1313
Glu Arg Trp Gln Glu Asn Asp Pro Lys Ser Asn Val Asp

AAG CTC AAG GGC AAG ACC ATC TAC GTT TTC TCT GTT AAC   1352
Lys Leu Lys Gly Lys Thr Ile Tyr Val Ser Ser Gly Asn

GGT GCA GAT GAC TTC GGT AAG GAA GAC TCT GTA GCT ATT   1391
Gly Ala Asp Asp Phe Gly Lys Glu Asp Ser Val Ala Ile

GGA CCT GCA AAC GCG ACA GGT GTC GGT CTG GAA GTT ATG   1430
Gly Pro Ala Asn Ala Thr Gly Val Gly Leu Glu Val Ile

TCC CGT ATG ATG TCC CAG ACC TCC GTC GAT CGT GCA ACC   1469
Ser Arg Met Thr Ser Gln Thr Ser Val Asp Arg Ala Asn

CAG GCT GGC GTG GAA GTT GTT GCT AGC TTC CGT CCA TCC   1508
Gln Ala Gly Val Glu Val Val Ala Ser Phe Arg Pro Ser

GGC GTG CAC TCA TGG GAA TAC TGG CAG TTC GAG ATG ACT   1547
Gly Val His Ser Trp Glu Tyr Trp Gln Phe Glu Met Thr
```

FIG. 2C (3rd plate)

| | | | | | | | | | | | | |
|---|---|---|---|---|---|---|---|---|---|---|---|---|
| CAG | GCG | TTC | CCT | CAC | ATC | GCT | AAC | GCT | CTT | GGC | ATG | TCC | 1586 |
| Gln | Ala | Phe | Pro | His | Ile | Ala | Asn | Ala | Leu | Gly | Met | Ser | |
| ACT | GAG | GAC | CGT | GGC | GTT | GAG | TGT | GCA | CCT | GTC | GGC | GCA | 1625 |
| Thr | Glu | Asp | Arg | Gly | Val | Glu | Cys | Ala | Pro | Val | Gly | Ala | |
| ATC | GCT | GAC | GCT | GTT | GCC | GAC | GGC | GCG | ATG | GGC | ACC | TGC | 1664 |
| Ile | Ala | Asp | Ala | Val | Ala | Asp | Gly | Ala | Met | Gly | Thr | Cys | |
| CTG | ACC | AAC | GAA | TAC | GAT | GTT | ACC | GGC | GGT | AAG | GCC | CAG | 1703 |
| Leu | Thr | Asn | Glu | Tyr | Asp | Val | Thr | Gly | Gly | Lys | Ala | Gln | |
| GAC | TTC | GCT | AAC | GGT | CGC | GCA | TAC | TGG | TCT | GCA | AAC | ACT | 1742 |
| Asp | Phe | Ala | Asn | Gly | Arg | Ala | Tyr | Trp | Ser | Ala | Asn | Thr | |
| GGC | GCT | TTC | GGC | CTG | GTT | GGA | CGC | ATC | AAC | GCT | CGT | TAC | 1781 |
| Gly | Ala | Phe | Gly | Leu | Val | Gly | Arg | Ile | Asn | Ala | Arg | Tyr | |
| TCT | GAG | CTG | GGT | GGA | CCT | GAC | TCC | TGG | TTG | GGC | TAC | CCA | 1820 |
| Ser | Glu | Leu | Gly | Gly | Pro | Asp | Ser | Trp | Leu | Gly | Tyr | Pro | |
| ACC | TCT | TCT | GAG | TTG | AAG | ACA | CCA | GAC | GGA | CGT | GGC | CGC | 1859 |
| Thr | Ser | Ser | Glu | Leu | Lys | Thr | Pro | Asp | Gly | Arg | Gly | Arg | |
| TTC | GTC | ACC | TTC | GAG | CAC | GGC | TCC | ATC | TAC | TGG | ACC | GCC | 1898 |
| Phe | Val | Thr | Phe | Glu | His | Gly | Ser | Ile | Tyr | Trp | Thr | Ala | |
| ACC | ACT | GGT | CCT | TGG | GAA | ATC | CCA | GGC | GAT | ATG | CTC | GCC | 1937 |
| Thr | Thr | Gly | Pro | Trp | Glu | Ile | Pro | Gly | Asp | Met | Leu | Ala | |
| GCA | TGG | GGC | ACC | CAG | GAC | TAT | GAG | AAG | GGC | AGC | CTC | GGC | 1976 |
| Ala | Trp | Gly | Thr | Gln | Asp | Tyr | Glu | Lys | Gly | Ser | Leu | Gly | |
| TAC | CCA | ACC | GGC | GCC | GCA | GTT | GAA | TAC | AAC | GGT | GGC | CTG | 2015 |
| Tyr | Pro | Thr | Gly | Ala | Ala | Val | Glu | Tyr | Asn | Gly | Gly | Leu | |
| CGC | CAG | CAG | TTC | GAA | GGT | GGC | TAC | GTA | TTC | CGT | ACC | TCC | 2054 |
| Arg | Gln | Gln | Phe | Glu | Gly | Gly | Tyr | Val | Phe | Arg | Thr | Ser | |
| AAT | AAC | CAG | TCT | TAC | TGG | GTT | CGC | GGA | GAA | ATC | TCC | AAG | 2093 |
| Asn | Asn | Gln | Ser | Tyr | Trp | Val | Arg | Gly | Glu | Ile | Ser | Lys | |
| AAG | TAC | GCC | GAT | GAC | GGA | ATC | TTC | GCT | CAG | CTT | GGT | TTC | 2132 |
| Lys | Tyr | Ala | Asp | Asp | Gly | Ile | Phe | Ala | Gln | Leu | Gly | Phe | |
| CCA | ACC | GGC | AAT | GAG | AAG | TTG | ATC | AAC | GGT | GGC | GCT | TTC | 2171 |
| Pro | Thr | Gly | Asn | Glu | Lys | Leu | Ile | Asn | Gly | Gly | Ala | Phe | |
| CAG | GAA | TTC | GAA | AAG | GGC | AAC | ATC | TAC | TGG | TCC | GTG | TCC | 2210 |
| Gln | Glu | Phe | Glu | Lys | Gly | Asn | Ile | Tyr | Trp | Ser | Val | Ser | |

FIG. 2D (4th plate)

```
ACT GGC GCG CAC GTG ATT CTG CAC GGC GAC ATC TTC GAC   2249
Thr Gly Ala His Val Ile Leu His Gly Asp Ile Phe Asp

GCA TGG GGT GCT AAG GGC TGG GAG CAG GGC GAA TAC GGC   2288
Ala Trp Gly Ala Lys Gly Trp Glu Gln Gly Glu Tyr Gly

TTC CCA ACC TCT GAC CAG ACC GCA ATC ACC GCG GGT GGA   2327
Phe Pro Thr Ser Asp Gln Thr Ala Ile Thr Ala Gly Gly

CAG ACC ATT GAT TTC CAG AAC GGC ACC ATC CGT CAG GTC   2366
Gln Thr Ile Asp Phe Gln Asn Gly Thr Ile Arg Gln Val

AAT GGC CGA ATT GAG GAG TCT CGC TAATAGTGA AGCGCATCTA   2409
Asn Gly Arg Ile Glu Glu Ser Arg
```

CGCAACTCTCGCTTCCGGACTTTTGTGCCTGAGCCTTGCTGCTTGTGGGGGA 2461

GTCACTGTTGAAGGAGATGATTCTCCCTCGACAGCGGCAGCCCCAACAGAAA 2513

GCAGCGCTGGGTCAAGCAGCACCGCAAGGTCGAC 2547

FIG. 4A

FIG. 4B

FIG. 6
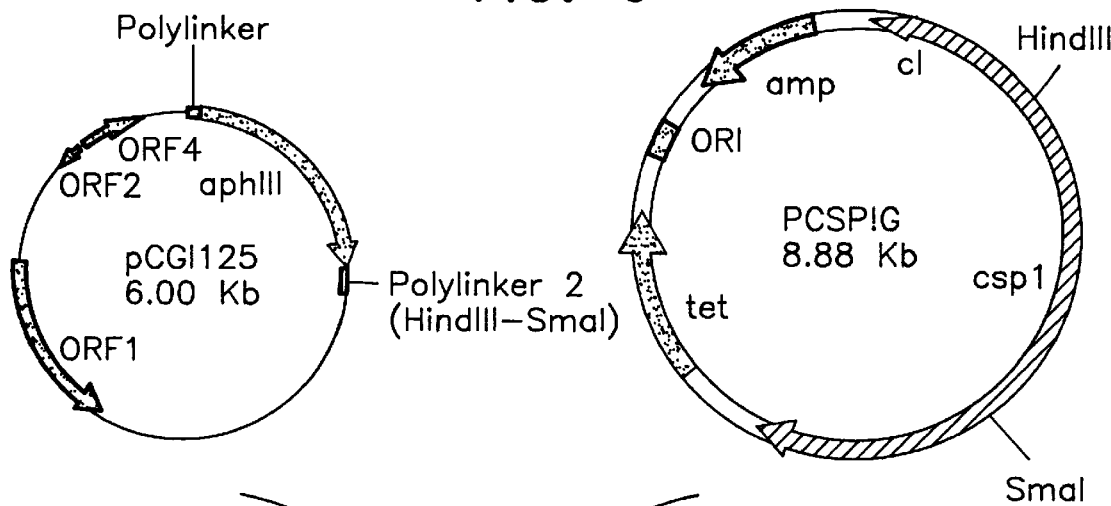
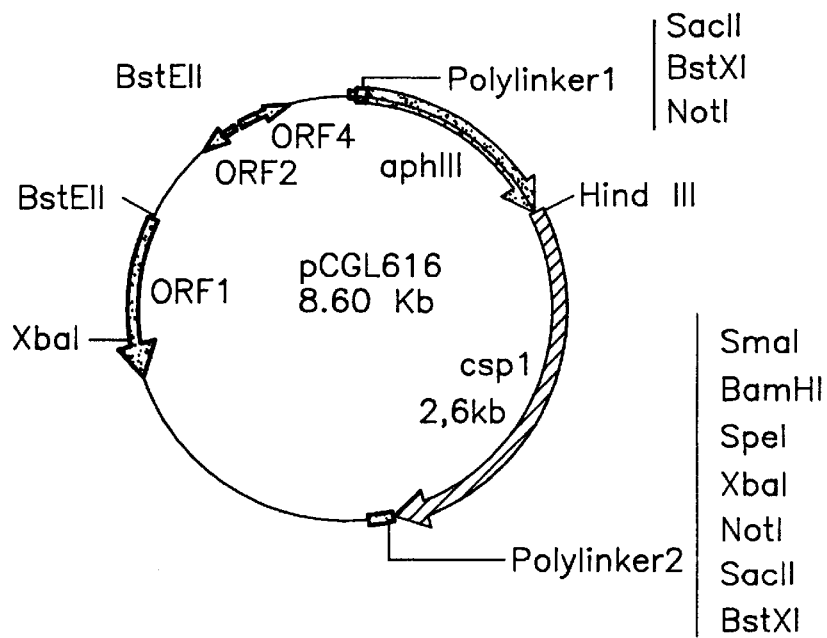

FIG. 12A (1st plate)

```
GAATTCCTGTGAATTAGCCGGTTTAGTACTTTTCAGGGGTGTCTATTCTTAC        52
CAGATCGTCAAGTTGTGGGTAGAGTCACCTGAATATTAATTGCACCGCACGG       104
GTGATATATGCTTATTTGCTCAAGTAGTTCGAGGTTAAGTGTATTTTAGGTG       156
AACAAATTTCAGCTTCGGGTAGAAGACTTTCTATGCGCTTCAGAGCTTCTAT       208
TAGGAAATCTGACACCACTTGATTAAATAGCCTACCCCCGAATTGGGGGATG       260
GGTCATTTTTTGCTGTGAAGGTAGTTTTGATGCATATGACCTGCGTTTATAA       312
AGAAATGTAAACGTGATCAGATCGATATAAAAGAAACAGTTTGTACTCAGGT       364
TTGAAGCATTTTCTCCGATTCGCCTGGCAAAAATCTCAATTGTCGCTTACAG       416
TTTTTCTCAACGACAGGCTGCTAAGCTGCTAGTTCGGTGGCCTAGTGAGTGG       468
CGTTTACTTGGATAAAAGTAATCCCATGTCGTGATCAGCCATTTTGGGTTGT       520
TTCCATAGCAATCCAAAGGTTTCGTCTTTCGATACCTATTCAAGGAGCCTTC       572
```

| GCCTCT | ATG | TTT | AAC | AAC | CGT | ATC | CGC | ACT | GCA | GCT | CTT | 611 |
|        | Met | Phe | Asn | Asn | Arg | Ile | Arg | Thr | Ala | Ala | Leu |     |
| GCT    | GGT | GCA | ATC | GCA | ATC | TCC | ACC | GCA | GCT | TCC | GGC | GTT | 650 |
| Ala    | Gly | Ala | Ile | Ala | Ile | Ser | Thr | Ala | Ala | Ser | Gly | Val |     |
| GCT    | ATC | CCA | GCA | TTC | GCT | CAG | GAG | ACC | AAC | CCA | ACT | TTC | 689 |
| Ala    | Ile | Pro | Ala | Phe | Ala | Gln | Glu | Thr | Asn | Pro | Thr | Phe |     |
| AAC    | ATC | ACC | AAC | GGC | TTC | AAC | GAT | GCT | GAT | GGA | TCC | ACC | 728 |
| Asn    | Ile | Thr | Asn | Gly | Phe | Asn | Asp | Ala | Asp | Gly | Ser | Thr |     |
| ATC    | CAG | CCA | GTT | GGC | CCT | GTT | AAC | CAC | ACC | GAG | GAA | ACC | 767 |
| Ile    | Gln | Pro | Val | Gly | Pro | Val | Asn | His | Thr | Glu | Glu | Thr |     |
| CTC    | CGC | GAC | CTG | ACT | GAC | TCC | ACC | GGC | GCT | TAC | CTG | GAA | 806 |
| Leu    | Arg | Asp | Leu | Thr | Asp | Ser | Thr | Gly | Ala | Tyr | Leu | Glu |     |
| GAG    | TTC | CAG | AAC | GGC | ACC | GTT | GAG | GAA | ATC | GTT | GAA | GCA | 845 |
| Glu    | Phe | Gln | Asn | Gly | Thr | Val | Glu | Glu | Ile | Val | Glu | Ala |     |
| TAC    | CTG | CAG | GTT | CAG | GCT | TCC | GCA | GAC | GGA | TTC | GAT | CCT | 884 |
| Tyr    | Leu | Gln | Val | Gln | Ala | Ser | Ala | Asp | Gly | Phe | Asp | Pro |     |
| TCT    | GAG | CAG | GCT | GCT | TAC | GAG | GCT | TTC | GAG | GCT | GCT | CGC | 923 |
| Ser    | Glu | Gln | Ala | Ala | Tyr | Glu | Ala | Phe | Glu | Ala | Ala | Arg |     |
| GTC    | CGT | GCA | TCC | CAG | GAG | CTC | GCA | GCT | TCC | GCT | GAG | ACC | 962 |
| Val    | Arg | Ala | Ser | Gln | Glu | Leu | Ala | Ala | Ser | Ala | Glu | Thr |     |

FIG. 12B (2nd plate)

```
ATC ACC AAG ACC CGC GAG TCC GTT GCT TAC GCA CTC AAG   1001
Ile Thr Lys Thr Arg Glu Ser Val Ala Tyr Ala Leu Lys

GTT GAC CAG GAA GCT ACC GCT GCT TTC GAG GCA TAC CGC   1040
Val Asp Gln Glu Ala Thr Ala Ala Phe Glu Ala Tyr Arg

AAC GCA CTT CGC GAT GCA GCT ATC TCT ATC AAC CCA GAT   1079
Asn Ala Leu Arg Asp Ala Ala Ile Ser Ile Asn Pro Asp

GGC TCT ATC AAC CCA GAT ACC TCT ATC AAC CTA CTG ATC   1118
Gly Ser Ile Asn Pro Asp Thr Ser Ile Asn Leu Leu Ile

GAT GCT GCT AAC GCT GCT AAC CGC ACC GAT CGT GCA GAG   1157
Asp Ala Ala Asn Ala Ala Asn Arg Thr Asp Arg Ala Glu

ATC GAG GAT TAC GCT CAC CTT TAC ACC CAG ACC GAT ATT   1196
Ile Glu Asp Tyr Ala His Leu Tyr Thr Gln Thr Asp Ile

GCT CTT GAA ACT CCA CAG CTT GCA TAC GCT TTC CAG GAC   1235
Ala Leu Glu Thr Pro Gln Leu Ala Tyr Ala Phe Gln Asp

CTG AAG GCT CTT CAG GCT GAG GTC GAC GCA GAC TTC GAG   1274
Leu Lys Ala Leu Gln Ala Glu Val Asp Ala Asp Phe Glu

TGG TTG GGC GAG TTC GGA ATC GAC CAG GAA GAC GGT ACC   1313
Trp Leu Gly Glu Phe Gly Ile Asp Gln Glu Asp Gly Asn

TAC GTT CAG CGC TAC CAC CTC CCT GCT GTA GAG GCA CTC   1352
Tyr Val Gln Arg Tyr His Leu Pro Ala Val Glu Ala Leu

AAG GCT GAG GTC GAC GCT CGC GTC GCA GCA ATT GAG CCA   1391
Lys Ala Glu Val Asp Ala Arg Val Ala Ala Ile Glu Pro

CTT CGT GCA GAC TCC ATC GCT AAG AAC CTT GAG GCG CAG   1430
Leu Arg Ala Asp Ser Ile Ala Lys Asn Leu Glu Ala Gln

AAG TCT GAC GTT CTG GTT CGC CAG CTC TTC CTC GAG CGT   1469
Lys Ser Asp Val Leu Val Arg Gln Leu Phe Leu Glu Arg

GCA ACC GCA CAG CGC GAC ACC CTG CGT GTT GTA GAG GCG   1508
Ala Thr Ala Gln Arg Asp Thr Leu Arg Val Val Glu Ala

ATC TTC TCT ACC TCT GCT CGT TAC GTT GAA CTC TAC GAG   1547
Ile Phe Ser Thr Ser Ala Arg Tyr Val Glu Leu Tyr Glu

AAC GTC GAG AAC GTT AAC GTT GAG AAC AAG ACC CTT CGC   1586
Asn Val Glu Asn Val Asn Val Glu Asn Lys Thr Leu Arg
```

FIG. 12C (3rd plate)

| | | | | | | | | | | | | |
|---|---|---|---|---|---|---|---|---|---|---|---|---|
| CAG | CAC | TAC | TCT | GCG | CTG | ATC | CCT | AAC | CTC | TTC | ATC | GCA | 1625
| Gln | His | Tyr | Ser | Ala | Leu | Ile | Pro | Asn | Leu | Phe | Ile | Ala |
| GCA | GTT | GCA | AAC | ATC | AGC | GAG | CTC | AAC | GCT | GCA | GAT | GCT | 1664
| Ala | Val | Ala | Asn | Ile | Ser | Glu | Leu | Asn | Ala | Ala | Asp | Ala |
| GAA | GCA | GCA | GCT | TAC | TAC | CTC | CAC | TGG | GAC | ACC | GAC | CTC | 1703
| Glu | Ala | Ala | Ala | Tyr | Tyr | Leu | His | Trp | Asp | Thr | Asp | Leu |
| GCA | ACC | AAC | GAT | GAG | GAC | GAA | GCT | TAC | TAC | AAG | GCT | AAG | 1742
| Ala | Thr | Asn | Asp | Glu | Asp | Glu | Ala | Tyr | Tyr | Lys | Ala | Lys |
| CTC | GAC | TTC | GCT | ATC | GAG | ACC | TAC | GCA | AAG | ATC | CTG | TCC | 1781
| Leu | Asp | Phe | Ala | Ile | Glu | Thr | Tyr | Ala | Lys | Ile | Leu | Phe |
| AAC | GGT | GAA | GTT | TGG | CAG | GAG | CCA | CTG | GCT | TAC | GTC | CAG | 1820
| Asn | Gly | Glu | Val | Trp | Gln | Glu | Pro | Leu | Ala | Tyr | Val | Gln |
| AAC | CTG | GAT | GCA | GGC | GCA | CGT | CAG | GAA | GCA | GCT | GAC | CGT | 1859
| Asn | Leu | Asp | Ala | Gly | Ala | Arg | Gln | Glu | Ala | Ala | Asp | Arg |
| GAG | GCA | GCT | CGC | GCA | GCT | GAC | GAA | GCT | TAC | CGC | GCT | GAG | 1898
| Glu | Ala | Ala | Arg | Ala | Ala | Asp | Glu | Ala | Tyr | Arg | Ala | Glu |
| CAG | CTC | CGC | ATC | GCT | CAG | GAA | GCA | GCT | GAC | GCT | CAG | AAG | 1937
| Gln | Leu | Arg | Ile | Ala | Gln | Glu | Ala | Ala | Asp | Ala | Gln | Lys |
| GCT | ATC | GCT | GAG | GCG | CTT | GCT | AAG | GAA | GCA | GAA | GGC | AAC | 1976
| Ala | Ile | Ala | Glu | Ala | Leu | Ala | Lys | Glu | Ala | Glu | Gly | Asn |
| AAC | GAC | AAC | TCC | TCC | GAC | AAC | ACG | GAG | ACC | GGT | TCT | TCT | 2015
| Asn | Asp | Asn | Ser | Ser | Asp | Asn | Thr | Glu | Thr | Gly | Ser | Ser |
| GAC | ATC | GGA | TCC | TGG | GGA | CCT | TTC | GCA | GCA | ATT | GCA | GCT | 2054
| Asp | Ile | Gly | Ser | Trp | Gly | Pro | Phe | Ala | Ala | Ile | Ala | Ala |
| ATC | ATC | GCA | GCA | ATC | GCA | GCT | ATC | TTC | CCA | TTC | CTC | TCC | 2093
| Ile | Ile | Ala | Ala | Ile | Ala | Ala | Ile | Phe | Pro | Phe | Leu | Ser |
| GGT | ATC | GTT | AAG | TTC | TAA | TTTCGAACCGAGATAGCTAAAAGTTAAA | | | | | | | 2139
| Gly | Ile | Val | Lys | Phe | | | | | | | | |

CCACCTCCTTTCTTGCGGGAGGTGGTTTTTCCCTTGGTAACAGCACCAAAA 2191

GAAAAGCCACCTCCTTGATCTCAAGGAGGTGGCTTATCTTTTATTTACTGGG 2243

GAGCCGGAGGTTGGCGTCGATAAGCAAAAATCTTTTGCTTTTAAGGGAACGT 2295

FIG. 12D (4th plate)

| | |
|---|---|
| GATAATCGGCTTAATGACTCGCCACTGGCGGAATCCGCAAAGGCATCATTGA | 2347 |
| TTTGTTCCAGCGGGTAAGTGCGCACGAGCTTCTCGATCGGGAACTTGCCCTG | 2399 |
| GCGCCACAAATGAACCAGGCGAGGGATGAAATCCTGAGGGACGGCGTCGCCC | 2451 |
| TCAATGATGGTCTGGAACTTCCAACCACGGACCAGTGACGCGCCAACCTCGA | 2503 |
| AGGTAGCTTCCGTGCCAGGGGCAGGGGCGCCGACGAGACCGACGGTACCGTT | 2555 |
| GATCGCCAAGGAATCGGCTGCTTGCCTGGTCACGGCCACGACACCAGTTGTA | 2607 |
| TCGAGAGCGAATTGCACACCATCGCCGGTCAGTTCCTTGATTTTCTCCGCAG | 2659 |
| GATCCTCATCCTTGGAGTTGATCGTGTGGGTAGCTCCGAGCTC | 2702 |

FIG. 17A (1st plate)

```
GCTAGCCTGGGAGCTCTAGGAGATTGTGAAAAACGGGTCAAATTTCTCCGA    52
TGCAGCGCCTATAAAAGTCGTACCAATTCCATTTGAGGGTGCTCAAGTGTGG   104
CCAGGTTATATAACCAGTCAGTCAACTGGTCTCATTCGCTGGTCGGATGAAT   156
TTAATTAAAGAAGAGACTTCATGCAGTTACCGCGCGTTTTGGCGATACACAA   208
TTGATAAACCTAAAGAAATTTTCAAACAATTTTAATTCTTTGTGGTCATATC   260
TGTGCGACACTGCCATAATTGAACGTGAGCCATTTACCAGCCTAAATGCCCGC  312
AGTGAGTTAAGTCTCAAAGCAAGAAGTTGCTCTTTAGGGCATCCGTAGTTTA   364
AAACTATTAACCGTTAGGTATGACAAGCCGGTTGATGTGAACGCAGTTTTTA   416
AAAGTTTCAGGATCAGATTTTTCACAGGCATTTTGCTCCAGCAAACGCCTAG   468
GATGTACATGGTGCCCTCAATGGGAACCACCAACATCACTAAATGGCCCAGA   520
TACACACTTTAAAATCGTGCGCGCATGCAGCCGAGATGGGAACGAGGAAATC   572
```

| ATG | ACA | GTT | GAT | GAG | CAG | GTC | TCT | ACC | TAT | TAC | GAC | ATG | 611 |
|---|---|---|---|---|---|---|---|---|---|---|---|---|---|
| met | thr | val | asp | glu | gln | val | ser | asn | tyr | tyr | asp | met | |
| CTT | CTG | AAG | CGC | AAT | GCT | GGC | GAG | CCT | GAA | TTT | CAC | CAG | 650 |
| leu | leu | lys | arg | asn | ala | gly | glu | pro | glu | phe | his | gln | |
| GCA | GTG | GCA | GAG | GTT | TTG | GAA | TCT | TTG | AAG | ATC | GTC | CTG | 689 |
| ala | val | ala | glu | val | leu | glu | ser | leu | lys | ile | val | leu | |
| GAA | AAG | GAC | CCT | CAT | TAC | GCT | GAT | TAC | GGT | CTC | ATC | CAG | 728 |
| glu | lys | asp | pro | his | tyr | ala | asp | tyr | gly | leu | ile | gln | |
| CGC | CTG | TGC | GAG | CCT | GAG | CGT | CAG | CTC | ATC | TTC | CGT | GTG | 767 |
| arg | leu | cys | glu | pro | glu | arg | gln | leu | ile | phe | arg | val | |
| CCT | TGG | GTT | GAT | GAC | CAG | GGC | CAG | GTC | CAC | GTC | AAC | CGT | 806 |
| pro | trp | val | asp | asp | gln | gly | gln | val | his | val | asn | arg | |
| GGT | TTC | CGC | GTG | CAG | TTC | AAC | TCT | GCA | CTT | GGA | CCA | TAC | 845 |
| gly | phe | arg | val | gln | phe | asn | ser | ala | leu | gly | pro | tyr | |
| AAG | GGC | GGC | CTG | CGC | TTC | CAC | CCA | TCT | GTA | AAC | CTG | GGC | 884 |
| lys | gly | gly | leu | arg | phe | his | pro | ser | val | asn | leu | gly | |
| ATT | GTG | AAG | TTC | CTG | GGC | TTT | GAG | CAG | ATC | TTT | AAA | AAC | 923 |
| ile | val | lys | phe | leu | gly | phe | glu | gln | ile | phe | lys | asn | |
| TCC | CTA | ACC | GGC | CTG | CCA | ATC | GGT | GGT | GGC | AAG | GGT | GGA | 962 |
| ser | leu | thr | gly | leu | pro | ile | gly | gly | gly | lys | gly | gly | |

FIG. 17B (2nd plate)

| | | | | | | | | | | | | |
|---|---|---|---|---|---|---|---|---|---|---|---|---|
| TCC ser | GAC asp | TTC phe | GAC asp | CCT pro | AAG lys | GGC gly | AAG lys | TCC ser | GAT asp | CTG leu | GAA glu | ATC ile | 1001 |
| ATG met | CGT arg | TTC phe | TGC cys | CAG gln | TCC ser | TTC phe | ATG met | ACC thr | GAG glu | CTG leu | CAC his | CGC arg | 1040 |
| CAC his | ATC ile | GGT gly | GAG glu | TAC tyr | CGC arg | GAC asp | GTT val | CCT pro | GCA ala | GGT gly | GAC asp | ATC ile | 1079 |
| GGA gly | GTT val | GGT gly | GGC gly | CGC arg | GAG glu | ATC ile | GGT gly | TAC tyr | CTG leu | TTT phe | GGC gly | CAC his | 1118 |
| TAC tyr | CGT arg | CGC arg | ATG met | GCC ala | AAC asn | CAG gln | CAC his | GAG glu | TCC ser | GGC gly | GTT val | TTG leu | 1157 |
| ACC thr | GGT gly | AAG lys | GGC gly | CTG leu | ACC thr | TGG trp | GGT gly | GGA gly | TCC ser | CTG leu | GTC val | CGC arg | 1196 |
| ACC Thr | GAG glu | GCA ala | ACT thr | GGC gly | TAC tyr | GGC gly | TGC cys | GTT val | TAC tyr | TTC phe | GTG val | AGT ser | 1235 |
| GAA glu | ATG met | ATC ile | AAG lys | GCT ala | AAG lys | GGC gly | GAG glu | AGC ser | ATC ile | AGC ser | GGC gly | CAG gln | 1274 |
| AAG lys | ATC ile | ATC ile | GTT val | TCC ser | GGT gly | TCC ser | GGC gly | AAC asn | GTA val | GCA ala | ACC thr | TAC tyr | 1313 |
| GCG ala | ATT ile | GAA glu | AAG lys | GCT ala | CAG gln | GAA glu | CTC leu | GGC gly | GCA ala | ACC thr | GTT val | ATT ile | 1352 |
| GGT gly | TTC phe | TCC ser | GAT asp | TCC ser | AGC ser | GGT gly | TGG trp | GTT val | CAT his | ACC thr | CCT pro | AAT asn | 1391 |
| GGC gly | GTT val | GAC asp | GTG val | GCT ala | AAG lys | CTC leu | CGC arg | GAA glu | ATC ile | AAG lys | GAA glu | GTT val | 1430 |
| CGC arg | CGC arg | GCA ala | CGC arg | GTA val | TCC ser | GTG val | TAC tyr | GCC ala | GAC asp | GAA glu | GTT val | GAA glu | 1469 |
| GGC gly | GCA ala | ACC thr | TAC tyr | CAC his | ACC thr | GAC asp | GGG gly | TCC ser | ATC ile | TGG trp | GAT asp | CTC leu | 1508 |
| AAG lys | TGC cys | GAT asp | ATC ile | GCT ala | CTT leu | CCT pro | TGT cys | GCA ala | ACT thr | CAG gln | AAC asn | GAG glu | 1547 |
| CTC leu | AAC asn | GGT gly | GAG glu | AAC asn | GCT ala | AAG lys | ACT thr | CTT leu | GCA ala | GAC asp | AAC asn | GGC gly | 1586 |
| TGC cys | CGT arg | TTC phe | GTT val | GCT ala | GAA glu | GGC gly | GCG ala | AAC asn | ATG met | CCT pro | TCC ser | ACC thr | 1625 |

FIG. 17C (3rd plate)

| | | | | | | | | | | | | | |
|---|---|---|---|---|---|---|---|---|---|---|---|---|---|
| CCA | GAG | GCT | GTT | GAG | GTC | TTC | CGT | GAG | CGC | GAC | ATC | CGC | 1164 |
| pro | glu | ala | val | glu | val | phe | arg | glu | arg | asp | ile | arg | |
| TTC | GGA | CCA | GGC | AAG | GCA | GCT | AAC | GCT | GGT | GGC | GTT | GCA | 1703 |
| phe | gly | pro | gly | lys | ala | ala | asn | ala | gly | gly | val | ala | |
| ACC | TCC | GCT | CTG | GAG | ATG | CAG | CAG | AAC | GCT | TCG | CGC | GAT | 1742 |
| thr | ser | ala | leu | glu | met | gln | gln | asn | ala | ser | arg | asp | |
| TCC | TGG | AGC | TTC | GAG | TAC | ACC | GAC | GAG | CGC | CTC | CAG | GTG | 1781 |
| ser | trp | ser | phe | glu | tyr | thr | asp | glu | arg | leu | gln | val | |
| ATC | ATG | AAG | AAC | ATC | TTC | AAG | ACC | TGT | GCA | GAG | ACC | GCA | 1820 |
| ile | met | lys | asn | ile | phe | lys | thr | cys | ala | glu | thr | ala | |
| GCA | GAG | TAT | GGA | CAC | GAG | AAC | GAT | TAC | GTT | GTC | GGC | GCT | 1859 |
| ala | glu | tyr | gly | his | glu | asn | asp | tyr | val | val | gly | ala | |
| AAC | ATT | GCT | GGC | TTC | AAG | AAG | GTA | GCT | GAC | GCG | ATG | CTG | 1898 |
| asn | ile | ala | gly | phe | lys | lys | val | ala | asp | ala | met | leu | |
| GCA | CAG | GGC | GTC | ATC | TAA | GACCCCTGCACTTTACTTAAACCCCTGA | | | | | | | 1944 |
| ala | gln | gly | val | ile | OCH | | | | | | | | |

TCCGCGTTAAGGATCAGGGATTTTTGATTTCTTCCAGGTCAATTATCCGATC    1996

CACATGGGTTAATGCAGCTGTGCGGTGCGCAATGATGATCACCGTGGTGTCT    2048

TTAAGCGTGGCCAGAGTCTGGGAAAGATCCGCTTGATTGAGCGCATCTTGGT    2100

GGCTGGTGGCTTCATCGACAATCAGTACCTGAGGGGTGCGTGCCAAAGCACG    2152

CGCCAGGCAGAGCCGTTGTTGCTGTCCGCCAGATAGGC    2190

FIG. 19

DGF1: 32 mer

5'    AATTCCATGGCAATGGCCGGCCTGTCGACCCC    3'

DGF2: 28 mer

5'    GGGGTCGACAGGCCGGCCATTGCCATGG    3'

DGF3: 120 mer

5'    CAGGCACAGGCTCAGGCCCAGGCACAGGCCCAGGCGCAGG
          CCCAGGCCCAGGCTCAGGCACAGGCGCAGGCGCAGGCGCA
          GGCACAGGCACAGGCTCAGGCGCAGGCTCAGGCTCAGGCA    3'

DGF6: 120 mer

5'    TGAGCCTTGAGCCTGCGCCTGAGCCTGTGCCTGTGCCTGCG
          CCTGCGCCTGCGCCTGTGCCTGAGCCTGGGCCTGGGCCTG
          CGCCTGGGCCTGTGCCTGGGCCTGAGCCTGTGCCTGTGCC    3'

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
       (A) LENGTH: 2547 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Corynebacterium Melassecola (ix) FEATURE:
       (A) NAME/KEY: CDS
       (B) LOCATION: 420..2390

(xi) SEQUENCE DESCRIPTION: SEQ ID NO:1:

```
AAGCTTCAAG GGGAAAACAA GGGCCTTAAA AGTTATCCAC AGATCCGAAG TGATCCGCGC      60

ACTGGGGTGA AAAGTTATCC ACAGGAAGCG GAGGGGCGGA TTGAAAAATT CAGCGAAATG     120

CGAAAAGGTG GAGGGGAAAT GCTGCGAGTC TTGCGGATTC CCGGCGTGGC ATTGAAAAAA     180

GTCTAAAGTT GAACTTAAGA TTGAGGTCAT TCTGAAGTTG TGACCTGCAT CAGAAGAGTT     240

ACATACCCAC ATATGTAACC TTCTGGACTA AGATCACGAC AGACTGAAAA GAACTGAAGA     300

CTCTCAAGGC ATAGCCCACG TGTGTTTGTC GGGCCGGAAG CGGGGAACTT TCGGGACGGA     360

TCTAACTCAT TGCGGGCCTG TGCGCAGTAT CCAAAAATCA AAATGAGAAG GAAAACTTC     419

ATG CGC GAC ACC GCA TTT CGT TCC ATC AAG GCT AAA GCT CAG GCT AAG      467
Met Arg Asp Thr Ala Phe Arg Ser Ile Lys Ala Lys Ala Gln Ala Lys
  1               5                  10                  15

CGC CGT TCC CTC TGG ATT GCA GCA GGC GCT GTC CCA ACC GCA ATT GCG      515
Arg Arg Ser Leu Trp Ile Ala Ala Gly Ala Val Pro Thr Ala Ile Ala
                 20                  25                  30

TTG ACT ATG TCC CTG GCA CCT ATG GCT TCG GCT CAG TCC AGC AAC CTT      563
Leu Thr Met Ser Leu Ala Pro Met Ala Ser Ala Gln Ser Ser Asn Leu
         35                  40                  45

TCC TCT GAT GCC GTA GTT GGC AGC ATC GCG CAG GGC GTC ACC GAT GGC      611
Ser Ser Asp Ala Val Val Gly Ser Ile Ala Gln Gly Val Thr Asp Gly
     50                  55                  60

CTG ACT GAC TAC CTG AAG CCT CGC GTC GAA GAG CTT CCT GCT GGT GAA      659
Leu Thr Asp Tyr Leu Lys Pro Arg Val Glu Glu Leu Pro Ala Gly Glu
 65                  70                  75                  80

GTC ACC TAC CCA GAG ATC GCC GGG CTG CCT GAT GGT GTG CGC GTG ATC      707
Val Thr Tyr Pro Glu Ile Ala Gly Leu Pro Asp Gly Val Arg Val Ile
                 85                  90                  95

AGC GCT GAG TGG GCA ACC TCC AAG CAT GTC ATT TTG ACT ATT CAG TCT      755
Ser Ala Glu Trp Ala Thr Ser Lys His Val Ile Leu Thr Ile Gln Ser
                100                 105                 110

GCA GCA ATG CCA GAG CGC CCA ATC AAG GTG CAG CTG CTG CTT CCG CGT      803
Ala Ala Met Pro Glu Arg Pro Ile Lys Val Gln Leu Leu Leu Pro Arg
            115                 120                 125

GAC TGG TAC TCT TCC CCG AAC CGT GAG TTC CCT GAA ATC TGG GCA CTT      851
Asp Trp Tyr Ser Ser Pro Asn Arg Glu Phe Pro Glu Ile Trp Ala Leu
        130                 135                 140
```

```
GAC GGT CTG CGC GCG ATT GAA GAG CAG AGT GGT TGG ACC ATT GAG ACC       899
Asp Gly Leu Arg Ala Ile Glu Glu Gln Ser Gly Trp Thr Ile Glu Thr
145                 150                 155                 160

AAC ATT GAG CAG TAC TAC GCC GAT AAG AAC GCC ATT GTT GTG CTC CCA       947
Asn Ile Glu Gln Tyr Tyr Ala Asp Lys Asn Ala Ile Val Val Leu Pro
                165                 170                 175

ATC GGT GGC GAG AGC TCC TTC TAC TCT GAC TGG GAA GAG CCA AAC AAC       995
Ile Gly Gly Glu Ser Ser Phe Tyr Ser Asp Trp Glu Glu Pro Asn Asn
            180                 185                 190

GGC AAG AAC TAC CAG TGG GAG ACC TTC CTG ACT CAG GAG CTC GCA CCG      1043
Gly Lys Asn Tyr Gln Trp Glu Thr Phe Leu Thr Gln Glu Leu Ala Pro
        195                 200                 205

ATC CTG GAC AAG GGC TTC CGT TCC AAC ACC GAT CGC GCC ATC ACC GGT      1091
Ile Leu Asp Lys Gly Phe Arg Ser Asn Thr Asp Arg Ala Ile Thr Gly
    210                 215                 220

ATC TCC ATG GGC GGT ACC GCT GCG GTT AAC ATC GCA ACC CAC CAC CCA      1139
Ile Ser Met Gly Gly Thr Ala Ala Val Asn Ile Ala Thr His His Pro
225                 230                 235                 240

GAC ATG TTT AAG TTC GTC GGT TCC TTC TCC GGC TAT CTG GAC ACC ACC      1187
Asp Met Phe Lys Phe Val Gly Ser Phe Ser Gly Tyr Leu Asp Thr Thr
                245                 250                 255

TCC GCT GGC ATG CCA ATC GCT ATT TCC GCA GCC CTG GCA GAC GCC GGC      1235
Ser Ala Gly Met Pro Ile Ala Ile Ser Ala Ala Leu Ala Asp Ala Gly
            260                 265                 270

GGA TAC GAT GCC AAC GCA ATG TGG GGA CCA GTC GGT TCT GAG CGC TGG      1283
Gly Tyr Asp Ala Asn Ala Met Trp Gly Pro Val Gly Ser Glu Arg Trp
        275                 280                 285

CAG GAA AAC GAT CCA AAG AGC AAC GTA GAC AAG CTC AAG GGC AAG ACC      1331
Gln Glu Asn Asp Pro Lys Ser Asn Val Asp Lys Leu Lys Gly Lys Thr
    290                 295                 300

ATC TAC GTT TCC TCT GGT AAC GGT GCA GAT GAC TTC GGT AAG GAA GAC      1379
Ile Tyr Val Ser Ser Gly Asn Gly Ala Asp Asp Phe Gly Lys Glu Asp
305                 310                 315                 320

TCT GTA GCT ATT GGA CCT GCA AAC GCG ACA GGT GTC GGT CTG GAA GTT      1427
Ser Val Ala Ile Gly Pro Ala Asn Ala Thr Gly Val Gly Leu Glu Val
                325                 330                 335

ATC TCC CGT ATG ACT TCC CAG ACC TTC GTC GAT CGT GCA AAC CAG GCT      1475
Ile Ser Arg Met Thr Ser Gln Thr Phe Val Asp Arg Ala Asn Gln Ala
            340                 345                 350

GGC GTG GAA GTT GTT GCT AGC TTC CGT CCA TCC GGC GTG CAC TCA TGG      1523
Gly Val Glu Val Val Ala Ser Phe Arg Pro Ser Gly Val His Ser Trp
        355                 360                 365

GAA TAC TGG CAG TTC GAG ATG ACT CAG GCG TTC CCT CAC ATC GCT AAC      1571
Glu Tyr Trp Gln Phe Glu Met Thr Gln Ala Phe Pro His Ile Ala Asn
    370                 375                 380

GCT CTT GGC ATG TCC ACT GAG GAC CGT GGC GTT GAG TGT GCA CCT GTC      1619
Ala Leu Gly Met Ser Thr Glu Asp Arg Gly Val Glu Cys Ala Pro Val
385                 390                 395                 400

GGC GCA ATC GCT GAC GCT GTT GCC GAC GGC GCG ATG GGC ACC TGC CTG      1667
Gly Ala Ile Ala Asp Ala Val Ala Asp Gly Ala Met Gly Thr Cys Leu
                405                 410                 415

ACC AAC GAA TAC GAT GTT ACC GGC GGT AAG GCC CAG GAC TTC GCT AAC      1715
Thr Asn Glu Tyr Asp Val Thr Gly Gly Lys Ala Gln Asp Phe Ala Asn
            420                 425                 430

GGT CGC GCA TAC TGG TCT GCA AAC ACT GGC GCT TTC GGC CTG GTT GGA      1763
Gly Arg Ala Tyr Trp Ser Ala Asn Thr Gly Ala Phe Gly Leu Val Gly
        435                 440                 445

CGC ATC AAC GCT CGT TAC TCT GAG CTG GGT GGA CCT GAC TCC TGG TTG      1811
Arg Ile Asn Ala Arg Tyr Ser Glu Leu Gly Gly Pro Asp Ser Trp Leu
    450                 455                 460
```

```
GGC TAC CCA ACC TCT TCT GAG TTG AAG ACA CCA GAC GGA CGT GGC CGC    1859
Gly Tyr Pro Thr Ser Ser Glu Leu Lys Thr Pro Asp Gly Arg Gly Arg
465                 470                 475                 480

TTC GTC ACC TTC GAG CAC GGC TCC ATC TAC TGG ACC GCC ACC ACT GGT    1907
Phe Val Thr Phe Glu His Gly Ser Ile Tyr Trp Thr Ala Thr Thr Gly
                    485                 490                 495

CCT TGG GAA ATC CCA GGC GAT ATG CTC GCC GCA TGG GGC ACC CAG GAC    1955
Pro Trp Glu Ile Pro Gly Asp Met Leu Ala Ala Trp Gly Thr Gln Asp
                500                 505                 510

TAT GAG AAG GGC AGC CTC GGC TAC CCA ACC GGC GCC GCA GTT GAA TAC    2003
Tyr Glu Lys Gly Ser Leu Gly Tyr Pro Thr Gly Ala Ala Val Glu Tyr
            515                 520                 525

AAC GGT GGC CTG CGC CAG CAG TTC GAA GGT GGC TAC GTA TTC CGT ACC    2051
Asn Gly Gly Leu Arg Gln Gln Phe Glu Gly Gly Tyr Val Phe Arg Thr
        530                 535                 540

TCC AAT AAC CAG TCT TAC TGG GTT CGC GGA GAA ATC TCC AAG AAG TAC    2099
Ser Asn Asn Gln Ser Tyr Trp Val Arg Gly Glu Ile Ser Lys Lys Tyr
545                 550                 555                 560

GCC GAT GAC GGA ATC TTC GCT CAG CTT GGT TTC CCA ACC GGC AAT GAG    2147
Ala Asp Asp Gly Ile Phe Ala Gln Leu Gly Phe Pro Thr Gly Asn Glu
                565                 570                 575

AAG TTG ATC AAC GGT GGC GCT TTC CAG GAA TTC GAA AAG GGC AAC ATC    2195
Lys Leu Ile Asn Gly Gly Ala Phe Gln Glu Phe Glu Lys Gly Asn Ile
                580                 585                 590

TAC TGG TCC GTG TCC ACT GGC GCG CAC GTG ATT CTG CAC GGC GAC ATC    2243
Tyr Trp Ser Val Ser Thr Gly Ala His Val Ile Leu His Gly Asp Ile
            595                 600                 605

TTC GAC GCA TGG GGT GCT AAG GGC TGG GAG CAG GGC GAA TAC GGC TTC    2291
Phe Asp Ala Trp Gly Ala Lys Gly Trp Glu Gln Gly Glu Tyr Gly Phe
        610                 615                 620

CCA ACC TCT GAC CAG ACC GCA ATC ACC GCG GGT GGA CAG ACC ATT GAT    2339
Pro Thr Ser Asp Gln Thr Ala Ile Thr Ala Gly Gly Gln Thr Ile Asp
625                 630                 635                 640

TTC CAG AAC GGC ACC ATC CGT CAG GTC AAT GGC CGA ATT GAG GAG TCT    2387
Phe Gln Asn Gly Thr Ile Arg Gln Val Asn Gly Arg Ile Glu Glu Ser
                645                 650                 655

CGC TAATAGTGAA GCGCATCTAC GCAACTCTCG CTTCCGGACT TTTGTGCCTG         2440
Arg

AGCCTTGCTG CTTGTGGGGG AGTCACTGTT GAAGGAGATG ATTCTCCCTC GACAGCGGCA  2500

GCCCCAACAG AAAGCAGCGC TGGGTCAAGC AGCACCGCAA GGTCGAC               2547

(2) INFORMATION FOR SEQ ID NO:2:

(i) SEQUENCE CHARACTERISTICS:
        (A) LENGTH: 657 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
                20                  25                  30

Leu Thr Met Ser Leu Ala Pro Met Ala Ser Ala Gln Ser Ser Asn Leu
            35                  40                  45

Ser Ser Asp Ala Val Val Gly Ser Ile Ala Gln Gly Val Thr Asp Gly
        50                  55                  60
```

-continued

```
Leu Thr Asp Tyr Leu Lys Pro Arg Val Glu Glu Leu Pro Ala Gly Glu
 65                  70                  75                  80

Val Thr Tyr Pro Glu Ile Ala Gly Leu Pro Asp Gly Val Arg Val Ile
                 85                  90                  95

Ser Ala Glu Trp Ala Thr Ser Lys His Val Ile Leu Thr Ile Gln Ser
            100                 105                 110

Ala Ala Met Pro Glu Arg Pro Ile Lys Val Gln Leu Leu Leu Pro Arg
        115                 120                 125

Asp Trp Tyr Ser Ser Pro Asn Arg Glu Phe Pro Glu Ile Trp Ala Leu
    130                 135                 140

Asp Gly Leu Arg Ala Ile Glu Glu Gln Ser Gly Trp Thr Ile Glu Thr
145                 150                 155                 160

Asn Ile Glu Gln Tyr Tyr Ala Asp Lys Asn Ala Ile Val Val Leu Pro
                165                 170                 175

Ile Gly Gly Glu Ser Ser Phe Tyr Ser Asp Trp Glu Pro Asn Asn
            180                 185                 190

Gly Lys Asn Tyr Gln Trp Glu Thr Phe Leu Thr Gln Glu Leu Ala Pro
        195                 200                 205

Ile Leu Asp Lys Gly Phe Arg Ser Asn Thr Asp Arg Ala Ile Thr Gly
    210                 215                 220

Ile Ser Met Gly Gly Thr Ala Ala Val Asn Ile Ala Thr His His Pro
225                 230                 235                 240

Asp Met Phe Lys Phe Val Gly Ser Phe Ser Gly Tyr Leu Asp Thr Thr
                245                 250                 255

Ser Ala Gly Met Pro Ile Ala Ile Ser Ala Ala Leu Ala Asp Ala Gly
            260                 265                 270

Gly Tyr Asp Ala Asn Ala Met Trp Gly Pro Val Gly Ser Glu Arg Trp
        275                 280                 285

Gln Glu Asn Asp Pro Lys Ser Asn Val Asp Lys Leu Lys Gly Lys Thr
    290                 295                 300

Ile Tyr Val Ser Ser Gly Asn Gly Ala Asp Asp Phe Gly Lys Glu Asp
305                 310                 315                 320

Ser Val Ala Ile Gly Pro Ala Asn Ala Thr Gly Val Gly Leu Glu Val
                325                 330                 335

Ile Ser Arg Met Thr Ser Gln Thr Phe Val Asp Arg Ala Asn Gln Ala
            340                 345                 350

Gly Val Glu Val Val Ala Ser Phe Arg Pro Ser Gly Val His Ser Trp
        355                 360                 365

Glu Tyr Trp Gln Phe Glu Met Thr Gln Ala Phe Pro His Ile Ala Asn
    370                 375                 380

Ala Leu Gly Met Ser Thr Glu Asp Arg Gly Val Glu Cys Ala Pro Val
385                 390                 395                 400

Gly Ala Ile Ala Asp Ala Val Ala Asp Gly Ala Met Gly Thr Cys Leu
                405                 410                 415

Thr Asn Glu Tyr Asp Val Thr Gly Gly Lys Ala Gln Asp Phe Ala Asn
            420                 425                 430

Gly Arg Ala Tyr Trp Ser Ala Asn Thr Gly Ala Phe Gly Leu Val Gly
        435                 440                 445

Arg Ile Asn Ala Arg Tyr Ser Glu Leu Gly Gly Pro Asp Ser Trp Leu
    450                 455                 460

Gly Tyr Pro Thr Ser Ser Glu Leu Lys Thr Pro Asp Gly Arg Gly Arg
465                 470                 475                 480

Phe Val Thr Phe Glu His Gly Ser Ile Tyr Trp Thr Ala Thr Thr Gly
                485                 490                 495
```

```
Pro Trp Glu Ile Pro Gly Asp Met Leu Ala Ala Trp Gly Thr Gln Asp
            500                 505                 510
Tyr Glu Lys Gly Ser Leu Gly Tyr Pro Thr Gly Ala Ala Val Glu Tyr
        515                 520                 525
Asn Gly Gly Leu Arg Gln Gln Phe Glu Gly Gly Tyr Val Phe Arg Thr
    530                 535                 540
Ser Asn Asn Gln Ser Tyr Trp Val Arg Gly Glu Ile Ser Lys Lys Tyr
545                 550                 555                 560
Ala Asp Asp Gly Ile Phe Ala Gln Leu Gly Phe Pro Thr Gly Asn Glu
                565                 570                 575
Lys Leu Ile Asn Gly Gly Ala Phe Gln Glu Phe Glu Lys Gly Asn Ile
            580                 585                 590
Tyr Trp Ser Val Ser Thr Gly Ala His Val Ile Leu His Gly Asp Ile
        595                 600                 605
Phe Asp Ala Trp Gly Ala Lys Gly Trp Glu Gln Gly Glu Tyr Gly Phe
    610                 615                 620
Pro Thr Ser Asp Gln Thr Ala Ile Thr Ala Gly Gly Gln Thr Ile Asp
625                 630                 635                 640
Phe Gln Asn Gly Thr Ile Arg Gln Val Asn Gly Arg Ile Glu Glu Ser
                645                 650                 655
Arg
```

(2) INFORMATION FOR SEQ ID NO:3:

(i) SEQUENCE CHARACTERISTICS:
        (A) LENGTH: 2702 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (ix) FEATURE:
        (A) NAME/KEY: CDS
        (B) LOCATION: 579..2108

(ix) FEATURE:
        (A) NAME/KEY: misc_feature
        (B) LOCATION: 579..668
        (D) OTHER INFORMATION: /product= "signal sequence of
            secreted protein"

(ix) FEATURE:
        (A) NAME/KEY: misc_feature
        (B) LOCATION: 562..567
        (D) OTHER INFORMATION: /product= "ribosome binding site"

(ix) FEATURE:
        (A) NAME/KEY: misc_feature
        (B) LOCATION: 2188..2233
        (D) OTHER INFORMATION: /product= "hairpin structure,
            putative transcription terminator signal of rho inde-
            pendent type (present at 76 nucleotides from the stop)"

(xi) SEQUENCE DESCRIPTION: SEQ ID NO:3:

```
GAATTCCTGT GAATTAGCCG GTTTAGTACT TTTCAGGGGT GTCTATTCTT ACCAGATCGT      60

CAAGTTGTGG GTAGAGTCAC CTGAATATTA ATTGCACCGC ACGGGTGATA TATGCTTATT     120

TGCTCAAGTA GTTCGAGGTT AAGTGTATTT TAGGTGAACA AATTTCAGCT TCGGGTAGAA     180
```

```
GACTTTCTAT GCGCTTCAGA GCTTCTATTA GGAAATCTGA CACCACTTGA TTAAATAGCC      240

TACCCCCGAA TTGGGGGATG GGTCATTTTT TGCTGTGAAG GTAGTTTTGA TGCATATGAC      300

CTGCGTTTAT AAAGAAATGT AAACGTGATC AGATCGTATA TAAAGAAACA GTTTGTACTC      360

AGGTTTGAAG CATTTTCTCC GATTCGCCTG GCAAAAATCT CAATTGTCGC TTACAGTTTT      420

TCTCAACGAC AGGCTGCTAA GCTGCTAGTT CGGTGGCCTA GTGAGTGGCG TTTACTTGGA      480

TAAAAGTAAT CCCATGTCGT GATCAGCCAT TTTGGGTTGT TTCCATAGCA ATCCAAAGGT      540

TTCGTCTTTC GATACCTATT CAAGGAGCCT TCGCCTCT ATG TTT AAC AAC CGT          593
                                          Met Phe Asn Asn Arg
                                            1                 5

ATC CGC ACT GCA GCT CTT GCT GGT GCA ATC GCA ATC TCC ACC GCA GCT        641
Ile Arg Thr Ala Ala Leu Ala Gly Ala Ile Ala Ile Ser Thr Ala Ala
                10                  15                  20

TCC GGC GTT GCT ATC CCA GCA TTC GCT CAG GAG ACC AAC CCA ACT TTC        689
Ser Gly Val Ala Ile Pro Ala Phe Ala Gln Glu Thr Asn Pro Thr Phe
        25                  30                  35

AAC ATC ACC AAC GGC TTC AAC GAT GCT GAT GGA TCC ACC ATC CAG CCA        737
Asn Ile Thr Asn Gly Phe Asn Asp Ala Asp Gly Ser Thr Ile Gln Pro
    40                  45                  50

GTT GGC CCT GTT AAC CAC ACC GAG GAA ACC CTC CGC GAC CTG ACT GAC        785
Val Gly Pro Val Asn His Thr Glu Glu Thr Leu Arg Asp Leu Thr Asp
55                  60                  65

TCC ACC GGC GCT TAC CTG GAA GAG TTC CAG AAC GGC ACC GTT GAG GAA        833
Ser Thr Gly Ala Tyr Leu Glu Glu Phe Gln Asn Gly Thr Val Glu Glu
70                  75                  80                  85

ATC GTT GAA GCA TAC CTG CAG GTT CAG GCT TCC GCA GAC GGA TTC GAT        881
Ile Val Glu Ala Tyr Leu Gln Val Gln Ala Ser Ala Asp Gly Phe Asp
                90                  95                 100

CCT TCT GAG CAG GCT GCT TAC GAG GCT TTC GAG GCT GCT CGC GTC CGT        929
Pro Ser Glu Gln Ala Ala Tyr Glu Ala Phe Glu Ala Ala Arg Val Arg
                105                 110                 115

GCA TCC CAG GAG CTC GCA GCT TCC GCT GAG ACC ATC ACC AAG ACC CGC        977
Ala Ser Gln Glu Leu Ala Ala Ser Ala Glu Thr Ile Thr Lys Thr Arg
                120                 125                 130

GAG TCC GTT GCT TAC GCA CTC AAG GTT GAC CAG GAA GCT ACC GCT GCT       1025
Glu Ser Val Ala Tyr Ala Leu Lys Val Asp Gln Glu Ala Thr Ala Ala
135                 140                 145

TTC GAG GCA TAC CGC AAC GCA CTT CGA GAT GCA GCT ATC TCT ATC AAC       1073
Phe Glu Ala Tyr Arg Asn Ala Leu Arg Asp Ala Ala Ile Ser Ile Asn
150                 155                 160                 165

CCA GAT GGC TCT ATC AAC CCA GAT ACC TCT ATC AAC CTA CTG ATC GAT       1121
Pro Asp Gly Ser Ile Asn Pro Asp Thr Ser Ile Asn Leu Leu Ile Asp
                170                 175                 180

GCT GCT AAC GCT GCT AAC CGC ACC GAT CGT GCA GAG ATC GAG GAT TAC       1169
Ala Ala Asn Ala Ala Asn Arg Thr Asp Arg Ala Glu Ile Glu Asp Tyr
                185                 190                 195

GCT CAC CTT TAC ACC CAG ACC GAT ATT GCT CTT GAA ACT CCA CAG CTT       1217
Ala His Leu Tyr Thr Gln Thr Asp Ile Ala Leu Glu Thr Pro Gln Leu
                200                 205                 210

GCA TAC GCT TTC CAG GAC CTG AAG GCT CTT CAG GCT GAG GTC GAC GCA       1265
Ala Tyr Ala Phe Gln Asp Leu Lys Ala Leu Gln Ala Glu Val Asp Ala
                215                 220                 225

GAC TTC GAG TGG TTG GGC GAG TTC GGA ATC GAC CAG GAA GAC GGT AAC       1313
Asp Phe Glu Trp Leu Gly Glu Phe Gly Ile Asp Gln Glu Asp Gly Asn
230                 235                 240                 245

TAC GTT CAG CGC TAC CAC CTC CCT GCT GTA CAG GCA CTC AAG GCT CAG       1361
Tyr Val Gln Arg Tyr His Leu Pro Ala Val Gln Ala Leu Lys Ala Gln
                250                 255                 260
```

```
GTC GAC GCT CGC GTC GCA GCA ATT GAG CCA CTT CGT GCA CAC TCC ATC          1409
Val Asp Ala Arg Val Ala Ala Ile Glu Pro Leu Arg Ala His Ser Ile
            265                 270                 275

GCT AAG AAC CTT GAG GCG CAG AAG TCT GAC GTT CTG GTT CGA CAG CTC          1457
Ala Lys Asn Leu Glu Ala Gln Lys Ser Asp Val Leu Val Arg Gln Leu
        280                 285                 290

TTC CTC GAG CGT GCA ACC GCA CAG CGC GAC ACC CTG CGT GTT GTA GAG          1505
Phe Leu Glu Arg Ala Thr Ala Gln Arg Asp Thr Leu Arg Val Val Glu
    295                 300                 305

GCG ATC TTC TCT ACC TCT GCT CGT TAC GTT GAA CTC TAC GAG AAC GTC          1553
Ala Ile Phe Ser Thr Ser Ala Arg Tyr Val Glu Leu Tyr Glu Asn Val
310                 315                 320                 325

GAG AAC GTT AAC GTT GAG AAC AAG ACC CTT CGC CAG CAC TAC TCT GCG          1601
Glu Asn Val Asn Val Glu Asn Lys Thr Leu Arg Gln His Tyr Ser Ala
            330                 335                 340

CTG ATC CCT AAC CTC TTC ATC GCA GCA GTT GCA AAC ATC AGC GAG CTC          1649
Leu Ile Pro Asn Leu Phe Ile Ala Ala Val Ala Asn Ile Ser Glu Leu
        345                 350                 355

AAC GCT GCA GAT GCT GAA GCA GCA GCT TAC TAC CTC CAC TGG GAC ACC          1697
Asn Ala Ala Asp Ala Glu Ala Ala Ala Tyr Tyr Leu His Trp Asp Thr
    360                 365                 370

GAC CTC GCA ACC AAC GAT GAG GAC GAA GCT TAC TAC AAG GCT AAG CTC          1745
Asp Leu Ala Thr Asn Asp Glu Asp Glu Ala Tyr Tyr Lys Ala Lys Leu
375                 380                 385

GAC TTC GCT ATC GAG ACC TAC GCA AAG ATC CTG TTC AAC GGT GAA GTT          1793
Asp Phe Ala Ile Glu Thr Tyr Ala Lys Ile Leu Phe Asn Gly Glu Val
390                 395                 400                 405

TGG CAG GAG CCA CTG GCT TAC GTC CAG AAC CTG GAT GCA GGC GCA CGT          1841
Trp Gln Glu Pro Leu Ala Tyr Val Gln Asn Leu Asp Ala Gly Ala Arg
            410                 415                 420

CAG GAA GCA GCT GAC CGT GAG GCA GCT CGC GCA GCT GAC GAA GCT TAC          1889
Gln Glu Ala Ala Asp Arg Glu Ala Ala Arg Ala Ala Asp Glu Ala Tyr
        425                 430                 435

CGC GCT GAG CAG CTC CGC ATC GCT CAG GAA GCA GCT GAC GCT CAG AAG          1937
Arg Ala Glu Gln Leu Arg Ile Ala Gln Glu Ala Ala Asp Ala Gln Lys
    440                 445                 450

GCT ATC GCT GAG GCG CTT GCT AAG GAA GCA GAA GGC AAC AAC GAC AAC          1985
Ala Ile Ala Glu Ala Leu Ala Lys Glu Ala Glu Gly Asn Asn Asp Asn
455                 460                 465

TCC TCC GAC AAC ACG GAG ACC GGT TCT TCT GAC ATC GGA TCC TGG GGA          2033
Ser Ser Asp Asn Thr Glu Thr Gly Ser Ser Asp Ile Gly Ser Trp Gly
470                 475                 480                 485

CCT TTC GCA GCA ATT GCA GCT ATC ATC GCA GCA ATC GCA GCT ATC TTC          2081
Pro Phe Ala Ala Ile Ala Ala Ile Ile Ala Ala Ile Ala Ala Ile Phe
            490                 495                 500

CCA TTC CTC TCC GGT ATC GTT AAG TTC TAATTTCGAA CCGAGATAGC                2128
Pro Phe Leu Ser Gly Ile Val Lys Phe
        505                 510

TAAAAGTTAA ACCACCTCCT TTCTTGCGGG AGGTGGTTTT TCCCTTGGCT AACAGCACCA        2188

AAAGAAAAGC CACCTCCTTG ATCTCAAGGA GGTGGCTTAT CTTTTATTTA CTGGGGAGCC        2248

GGAGGTTGGC GTCGATAAGC AAAAATCTTT TGCTTTTAAG GAACGTGAT AATCGGCTTA         2308

ATGACTCGCC ACTGGCGGAA TCCGCAAAGG CATCATTGAT TTGTTCCAGC GGGTAAGTGC        2368

GCACGAGCTT CTCGATCGGG AACTTGCCCT GGCGCCACAA ATGAACCAGG CGAGGGATGA        2428

AATCCTGAGG GACGGCGTCG CCCTCAATGA TGGTCTGGAA CTTCCAACCA CGGACCAGTG        2488

ACGCGCCAAC CTCGAAGGTA GCTTCCGTGC CAGGGGCAGG GGCGCCGACG AGACCGACGG        2548

TACCGTTGAT CGCCAAGGAA TCGGCTGCTT GCCTGGTCAC GGCCACGACA CCAGTTGTAT        2608
```

```
CGAGAGCGAA TTGCACACCA TCGCCGGTCA GTTCCTTGAT TTTCTCCGCA GGATCCTCAT    2668

CCTTGGAGTT GATCGTGTGG GTAGCTCCGA GCTC                                2702
```

(2) INFORMATION FOR SEQ ID NO:4:

(i) SEQUENCE CHARACTERISTICS:
        (A) LENGTH: 510 amino acids
        (B) TYPE: amino acid
        (D) TOPOLOGY: linear (ii) MOLECULE TYPE: protein (xi) SEQUENCE DESCRIPTION: SEQ ID NO:4:

```
Met Phe Asn Asn Arg Ile Arg Thr Ala Ala Leu Ala Gly Ala Ile Ala
 1               5                  10                  15

Ile Ser Thr Ala Ala Ser Gly Val Ala Ile Pro Ala Phe Ala Gln Glu
            20                  25                  30

Thr Asn Pro Thr Phe Asn Ile Thr Asn Gly Phe Asn Asp Ala Asp Gly
        35                  40                  45

Ser Thr Ile Gln Pro Val Gly Pro Val Asn His Thr Glu Glu Thr Leu
    50                  55                  60

Arg Asp Leu Thr Asp Ser Thr Gly Ala Tyr Leu Glu Glu Phe Gln Asn
65                  70                  75                  80

Gly Thr Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ala Ser Ala Glu Thr
        115                 120                 125

Ile Thr Lys Thr Arg Glu Ser Val Ala Tyr Ala Leu Lys Val Asp Gln
    130                 135                 140

Glu Ala Thr Ala Ala Phe Glu Ala Tyr Arg Asn Ala Leu Arg Asp Ala
145                 150                 155                 160

Ala Ile Ser Ile Asn Pro Asp Gly Ser Ile Asn Pro Asp Thr Ser Ile
                165                 170                 175

Asn Leu Leu Ile Asp Ala Ala Asn Ala Ala Asn Arg Thr Asp Arg Ala
            180                 185                 190

Glu Ile Glu Asp Tyr Ala His Leu Tyr Thr Gln Thr Asp Ile Ala Leu
        195                 200                 205

Glu Thr Pro Gln Leu Ala Tyr Ala Phe Gln Asp Leu Lys Ala Leu Gln
    210                 215                 220

Ala Glu Val Asp Ala Asp Phe Glu Trp Leu Gly Glu Phe Gly Ile Asp
225                 230                 235                 240

Gln Glu Asp Gly Asn Tyr Val Gln Arg Tyr His Leu Pro Ala Val Gln
                245                 250                 255

Ala Leu Lys Ala Gln Val Asp Ala Arg Val Ala Ile Glu Pro Leu
            260                 265                 270

Arg Ala His Ser Ile Ala Lys Asn Leu Glu Ala Gln Lys Ser Asp Val
        275                 280                 285

Leu Val Arg Gln Leu Phe Leu Glu Arg Ala Thr Ala Gln Arg Asp Thr
    290                 295                 300

Leu Arg Val Val Glu Ala Ile Phe Ser Thr Ser Ala Arg Tyr Val Glu
305                 310                 315                 320

Leu Tyr Glu Asn Val Glu Asn Val Asn Val Glu Asn Lys Thr Leu Arg
                325                 330                 335
```

-continued

```
Gln His Tyr Ser Ala Leu Ile Pro Asn Leu Phe Ile Ala Ala Val Ala
                340                 345                 350

Asn Ile Ser Glu Leu Asn Ala Ala Asp Ala Glu Ala Ala Ala Tyr Tyr
        355                 360                 365

Leu His Trp Asp Thr Asp Leu Ala Thr Asn Asp Glu Asp Glu Ala Tyr
370                 375                 380

Tyr Lys Ala Lys Leu Asp Phe Ala Ile Glu Thr Tyr Ala Lys Ile Leu
385                 390                 395                 400

Phe Asn Gly Glu Val Trp Gln Glu Pro Leu Ala Tyr Val Gln Asn Leu
                405                 410                 415

Asp Ala Gly Ala Arg Gln Glu Ala Ala Asp Arg Glu Ala Ala Arg Ala
                420                 425                 430

Ala Asp Glu Ala Tyr Arg Ala Glu Gln Leu Arg Ile Ala Gln Glu Ala
                435                 440                 445

Ala Asp Ala Gln Lys Ala Ile Ala Glu Ala Leu Ala Lys Glu Ala Glu
450                 455                 460

Gly Asn Asn Asp Asn Ser Ser Asp Asn Thr Glu Thr Gly Ser Ser Asp
465                 470                 475                 480

Ile Gly Ser Trp Gly Pro Phe Ala Ala Ile Ala Ile Ile Ala Ala
                485                 490                 495

Ile Ala Ala Ile Phe Pro Phe Leu Ser Gly Ile Val Lys Phe
            500                 505                 510
```

(2) INFORMATION FOR SEQ ID NO:5:

(i) SEQUENCE CHARACTERISTICS:
        (A) LENGTH: 2190 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (ix) FEATURE:
        (A) NAME/KEY: CDS
        (B) LOCATION: 573..1913

(xi) SEQUENCE DESCRIPTION: SEQ ID NO:5:

```
GCTAGCCTCG GGAGCTCTAG GAGATTGTGA AAAACGGGTC AAATTTCTCC GATGCAGCGC      60

CTATAAAGT  CGTACCAATT CCATTTGAGG GTGCTCAAGT GTGGCCAGGT TATATAACCA     120

GTCAGTCAAC TGGTCTCATT CGCTGGTCGG ATGAATTTAA TTAAAGAAGA GACTTCATGC     180

AGTTACCGCG CGTTTTGGCG ATACACAATT GATAAACCTA AGAAATTTT  CAAACAATTT    240

TAATTCTTTG TGGTCATATC TGTGCGACAC TGCCATAATT GAACGTGAGC ATTTACCAGC    300

CTAAATGCCC GCAGTGAGTT AAGTCTCAAA GCAAGAAGTT GCTCTTTAGG GCATCCGTAG    360

TTTAAAACTA TTAACCGTTA GGTATGACAA GCCGGTTGAT GTGAACGCAG TTTTTAAAAG    420

TTTCAGGATC AGATTTTTCA CAGGCATTTT GCTCCAGCAA ACGCCTAGGA TGTACATGGT    480

GCCCTCAATG GAACCACCA  ACATCACTAA ATGGCCCAGA TACACACTTT AAAATCGTGC    540

GCGCATGCAG CCGAGATGGG AACGAGGAAA TC ATG ACA GTT GAT GAG CAG GTC     593
                                   Met Thr Val Asp Glu Gln Val
                                     1               5

TCT AAC TAT TAC GAC ATG CTT CTG AAG CGC AAT GCT GGC GAG CCT GAA      641
```

|   |   |   |   |   |   |   |   |   |   |   |   |   |   |   |   |
|---|---|---|---|---|---|---|---|---|---|---|---|---|---|---|---|
| Ser | Asn | Tyr | Tyr | Asp | Met | Leu | Leu | Lys | Arg | Asn | Ala | Gly | Glu | Pro | Glu |
|     | 10  |     |     |     | 15  |     |     |     |     | 20  |     |     |     |     |     |

```
TTT CAC CAG GCA GTG GCA GAG GTT TTG GAA TCT TTG AAG ATC GTC CTG         689
Phe His Gln Ala Val Ala Glu Val Leu Glu Ser Leu Lys Ile Val Leu
    25              30                  35

GAA AAG GAC CCT CAT TAC GCT GAT TAC GGT CTC ATC CAG CGC CTG TGC         737
Glu Lys Asp Pro His Tyr Ala Asp Tyr Gly Leu Ile Gln Arg Leu Cys
40                  45                  50                  55

GAG CCT GAG CGT CAG CTC ATC TTC CGT GTG CCT TGG GTT GAT GAC CAG         785
Glu Pro Glu Arg Gln Leu Ile Phe Arg Val Pro Trp Val Asp Asp Gln
                60                  65                  70

GGC CAG GTC CAC GTC AAC CGT GGT TTC CGC GTG CAG TTC AAC TCT GCA         833
Gly Gln Val His Val Asn Arg Gly Phe Arg Val Gln Phe Asn Ser Ala
            75                  80                  85

CTT GGA CCA TAC AAG GGC GGC CTG CGC TTC CAC CCA TCT GTA AAC CTG         881
Leu Gly Pro Tyr Lys Gly Gly Leu Arg Phe His Pro Ser Val Asn Leu
        90                  95                  100

GGC ATT GTG AAG TTC CTG GGC TTT GAG CAG ATC TTT AAA AAC TCC CTA         929
Gly Ile Val Lys Phe Leu Gly Phe Glu Gln Ile Phe Lys Asn Ser Leu
105                 110                 115

ACC GGC CTG CCA ATC GGT GGT GGC AAG GGT GGA TCC GAC TTC GAC CCT         977
Thr Gly Leu Pro Ile Gly Gly Gly Lys Gly Gly Ser Asp Phe Asp Pro
120             125                 130                 135

AAG GGC AAG TCC GAT CTG GAA ATC ATG CGT TTC TGC CAG TCC TCC ATG        1025
Lys Gly Lys Ser Asp Leu Glu Ile Met Arg Phe Cys Gln Ser Ser Met
                140                 145                 150

ACC GAG CTG CAC CGC CAC ATC GGT GAG TAC CGC GAC GTT CCT GCA GGT        1073
Thr Glu Leu His Arg His Ile Gly Glu Tyr Arg Asp Val Pro Ala Gly
            155                 160                 165

GAC ATC GGA GTT GGT GGC CGC GAG ATC GGT TAC CTG TTT GGC CAC TAC        1121
Asp Ile Gly Val Gly Gly Arg Glu Ile Gly Tyr Leu Phe Gly His Tyr
        170                 175                 180

CGT CGC ATG GCC AAC CAG CAC GAG TCC GGC GTT TTG ACC GGT AAG GGC        1169
Arg Arg Met Ala Asn Gln His Glu Ser Gly Val Leu Thr Gly Lys Gly
185                 190                 195

CTG ACC TGG GGT GGA TCC CTG GTC CGC ACC GAG GCA ACT GGC TAC GGC        1217
Leu Thr Trp Gly Gly Ser Leu Val Arg Thr Glu Ala Thr Gly Tyr Gly
200                 205                 210                 215

TGC GTT TAC TTC GTG AGT GAA ATG ATC AAG GCT AAG GGC GAG AGC ATC        1265
Cys Val Tyr Phe Val Ser Glu Met Ile Lys Ala Lys Gly Glu Ser Ile
                220                 225                 230

AGC GGC CAG AAG ATC ATC GTT TCC GGT TCC GGC AAC GTA GCA ACC TAC        1313
Ser Gly Gln Lys Ile Ile Val Ser Gly Ser Gly Asn Val Ala Thr Tyr
            235                 240                 245

GCG ATT GAA AAG GCT CAG GAA CTC GGC GCA ACC GTT ATT GGT TTC TCC        1361
Ala Ile Glu Lys Ala Gln Glu Leu Gly Ala Thr Val Ile Gly Phe Ser
        250                 255                 260

GAT TCC AGC GGT TGG GTT CAT ACC CCT AAT GGC GTT GAC CTG GCT AAG        1409
Asp Ser Ser Gly Trp Val His Thr Pro Asn Gly Val Asp Leu Ala Lys
265                 270                 275

CTC CGC GAA ATC AAG GAA GTT CGC CGC GCA CGT GTA TCC CTG TAC GCC        1457
Leu Arg Glu Ile Lys Glu Val Arg Arg Ala Arg Val Ser Leu Tyr Ala
280                 285                 290                 295

GAC GAA GTT GAA GGC GCA ACC TAC CAC ACC GAC GGG TCC ATC TGG GAT        1505
Asp Glu Val Glu Gly Ala Thr Tyr His Thr Asp Gly Ser Ile Trp Asp
                300                 305                 310

CTC AAG TGC GAT ATC GCT CTT CCT TGT GCA ACT CAG AAC GAG CTC AAC        1553
Leu Lys Cys Asp Ile Ala Leu Pro Cys Ala Thr Gln Asn Glu Leu Asn
            315                 320                 325

GGT GAG AAC GCT AAG ACT CTT GCA GAC AAC GGC TGC CGT TTC GTT GCT        1601
```

-continued

```
Gly Glu Asn Ala Lys Thr Leu Ala Asp Asn Gly Cys Arg Phe Val Ala
            330                 335                 340

GAA GGC GCG AAC ATG CCT TCC ACC CCA GAG GCT GTT GAG GTC TTC CGT    1649
Glu Gly Ala Asn Met Pro Ser Thr Pro Glu Ala Val Glu Val Phe Arg
345                 350                 355

GAG CGC GAC ATC CGC TTC GGA CCA GGC AAG GCA GCT AAC GCT GGT GGC    1697
Glu Arg Asp Ile Arg Phe Gly Pro Gly Lys Ala Ala Asn Ala Gly Gly
360                 365                 370                 375

GTT GCA ACC TCC GCT CTG GAG ATG CAG CAG AAC GCT TCG CGC GAT TCC    1745
Val Ala Thr Ser Ala Leu Glu Met Gln Gln Asn Ala Ser Arg Asp Ser
                380                 385                 390

TGG AGC TTC GAG TAC ACC GAC GAG CGC CTC CAG GTG ATC ATG AAG AAC    1793
Trp Ser Phe Glu Tyr Thr Asp Glu Arg Leu Gln Val Ile Met Lys Asn
            395                 400                 405

ATC TTC AAG ACC TGT GCA GAG ACC GCA GCA GAG TAT GGA CAC GAG AAC    1841
Ile Phe Lys Thr Cys Ala Glu Thr Ala Ala Glu Tyr Gly His Glu Asn
        410                 415                 420

GAT TAC GTT GTC GGC GCT AAC ATT GCT GGC TTC AAG AAG GTA GCT GAC    1889
Asp Tyr Val Val Gly Ala Asn Ile Ala Gly Phe Lys Lys Val Ala Asp
425                 430                 435

GCG ATG CTG GCA CAG GGC GTC ATC TAAGACCCCT GCACTTTACT TAAACCCCTG   1943
Ala Met Leu Ala Gln Gly Val Ile
440                 445

ATCCGCGTTA AGGATCAGGG ATTTTTGATT TCTTCCAGGT CAATTATCCG ATCCACATGG  2003

GTTAATGCAG CTGTGCCGTG CGCAATGATG ATCACCGTGT CTCTTTAAG CGTGGCCAGA   2063

GTCTGGGAAA GATCCGCTTG ATTGAGCGCA TCTTGGTGGC TGGTGGCTTC ATCGACAATC  2123

AGTACCTGAG GGGTGCGTGC CAAAGCACGC GCCAGGCAGA GCCGTTGTTG CTGTCCGCCA  2183

GATAGGC                                                            2190
```

(2) INFORMATION FOR SEQ ID NO:6:

(i) SEQUENCE CHARACTERISTICS:
        (A) LENGTH: 447 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140
```

```
Arg Phe Cys Gln Ser Ser Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Leu Ala Lys Leu Arg Glu Ile Lys Glu Val Arg Arg
        275                 280                 285

Ala Arg Val Ser Leu Tyr Ala Asp Glu Val Glu Gly Ala Thr Tyr His
290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Gly Arg Asp Ile Arg Phe Gly Pro Gly
        355                 360                 365

Lys Ala Ala Asn Ala Gly Gly Val Ala Thr Ser Ala Leu Glu Met Gln
370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Corynebacterium Melassecola (xi) SEQUENCE DESCRIPTION: SEQ ID NO:7:

GAGAAGGAAA ACTTCATG                                              18
```

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:8:

GAUACCUUCC UUUCU                                                            15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus aureus and Streptomyces
            lividans (xi) SEQUENCE DESCRIPTION: SEQ ID NO:9:

AAAAGTTATC CACAG                                                            15

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (xi) SEQUENCE DESCRIPTION: SEQ ID NO:10:

TGGTCATATC TGTGCG                                                           16

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (ix) FEATURE:
            (A) NAME/KEY: misc_feature
            (B) LOCATION: 4
            (D) OTHER INFORMATION: /product= "N=py"

(ix) FEATURE:
            (A) NAME/KEY: misc_feature
            (B) LOCATION: 6
            (D) OTHER INFORMATION: /product= "N=pu"

(xi) SEQUENCE DESCRIPTION: SEQ ID NO:11:

TGGNANNNNN TTGCA                                                                15

(2) INFORMATION FOR SEQ ID NO:12:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Corynebacterium Melassecola (xi) SEQUENCE DESCRIPTION: SEQ ID NO:12:

GGGAACGAGG AAATC                                                                15

(2) INFORMATION FOR SEQ ID NO:13:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Corynebacterium Melassecola (xi) SEQUENCE DESCRIPTION: SEQ ID NO:13:

AAAGGAGGTG ATC                                                                  13

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Corynebacterium Melassecola (xi) SEQUENCE DESCRIPTION: SEQ ID NO:14:

CCCTGATCCG CGTTAAGGTC AGGG                                                      24

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (xi) SEQUENCE DESCRIPTION: SEQ ID NO:15:

TTATTTGATT TCTT                                              14

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (ix) FEATURE:
        (A) NAME/KEY: misc_feature
        (B) LOCATION: throughout the sequence
        (D) OTHER INFORMATION: /product= "N=sequence encoding
            Ala-Gln"

(xi) SEQUENCE DESCRIPTION: SEQ ID NO:16:

CAGNNNNNNN NNNNNNNNNN NNNCAGGCA                            29

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (ix) FEATURE:
        (A) NAME/KEY: misc_feature
        (B) LOCATION: throughout the sequence
        (D) OTHER INFORMATION: /product= "N=sequence encoding
            Ala-Gln"

(xi) SEQUENCE DESCRIPTION: SEQ ID NO:17:

CCGTGTCNNN NNNNNNNNNN NNNNNNNGT                            29

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Corynebacterium Melassecola (xi) SEQUENCE DESCRIPTION: SEQ ID NO:18:

CCATGGCAAT GG                                                12

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (xi) SEQUENCE DESCRIPTION: SEQ ID NO:19:

AATTCCATGG CAATGGCCGG CCTGTCGACC CC                         32

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (xi) SEQUENCE DESCRIPTION: SEQ ID NO:20:

GGGGTCGACA GGCCGGCCAT TGCCATGG                                28

(2) INFORMATION FOR SEQ ID NO:21:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: synthetic (xi) SEQUENCE DESCRIPTION: SEQ ID NO:21:

TGAGCCTGAG CCTGCGCCTG AGCCTGTGCC TGTGCCTGCG CCTGCGCCTG CGCCTGTGCC    60

TGAGCCTGGG CCTGGGCCTG CGCCTGGGCC TGTGCCTGGG CCTGAGCCTG TGCCTGTGCC    120

(2) INFORMATION FOR SEQ ID NO:22:

(i) SEQUENCE CHARACTERISTICS:
        (A) LENGTH: 120 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: synthetic (xi) SEQUENCE DESCRIPTION: SEQ ID NO:22:

Thr Gly Ala Gly Cys Cys Thr Gly Ala Gly Cys Cys Thr Gly Cys Gly
1               5                   10                  15

Cys Cys Thr Gly Ala Gly Cys Cys Thr Gly Thr Gly Cys Cys Thr Gly
            20                  25                  30

Thr Gly Cys Cys Thr Gly Cys Gly Cys Cys Thr Gly Cys Gly Cys Cys
        35                  40                  45

Thr Gly Cys Gly Cys Cys Thr Gly Thr Gly Cys Cys Thr Gly Ala Gly
    50                  55                  60

Cys Cys Thr Gly Gly Gly Cys Cys Thr Gly Gly Gly Cys Cys Thr Gly
65              70                  75                  80

Cys Gly Cys Cys Thr Gly Gly Gly Cys Cys Thr Gly Thr Gly Cys Cys
            85                  90                  95

Thr Gly Gly Gly Cys Cys Thr Gly Ala Gly Cys Cys Thr Gly Thr Gly
            100                 105                 110

Cys Cys Thr Gly Thr Gly Cys Cys
        115                 120

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (xi) SEQUENCE DESCRIPTION: SEQ ID NO:23:

GAATTCCATG GCAATGGCCG GCCTGTCGAC CCC                                 33

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (vi) ORIGINAL SOURCE:
             (A) ORGANISM: synthetic (xi) SEQUENCE DESCRIPTION: SEQ ID NO:24:

AUGGCAAUGG CCGGCCUGUC GACCCC                                                    26

(2) INFORMATION FOR SEQ ID NO:25:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: synthetic (xi) SEQUENCE DESCRIPTION: SEQ ID NO:25:

GAATTCCATG GCACAGNNNN NNGCAATGGC CGGCCTGTCG ACCCC                                45

(2) INFORMATION FOR SEQ ID NO:26:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: RNA (genomic)

(iii) HYPOTHETICAL: NO (iv) ANTI-SENSE: NO (vi) ORIGINAL SOURCE:
             (A) ORGANISM: synthetic (xi) SEQUENCE DESCRIPTION: SEQ ID NO:26:

AUGGCACAGN NNNNNGCAAU GGCCGGCCUG UCGACCCC                                        38

(2) INFORMATION FOR SEQ ID NO:27:

(i) SEQUENCE CHARACTERISTICS:
            (A) LENGTH: 423 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: synthetic (xi) SEQUENCE DESCRIPTION: SEQ ID NO:27:

ACACCGCATT TCGTTCCATC AAGGCTAAAG CTCAGGCTAA GCGCCGTTCC CTCTGGATTG                60

CAGCAGGCGC TGTCCCAACC GCAATTGCGT TGACTATGTC CCTGGCACCT ATGGCTTCGG               120

-continued

CTCAGTCCAG CAACCTTTCC TCTGATGCCG TAGTTGGCAG CATCGCGCAG GGCGTCACCG    180

ATGGCCTGAC TGACTACCTG AAGCCTCGCG TCGAAGACCT GCAGCCCAAT TCCATGGCAA    240

TGGCCGGCCT GTCGACCCCG GCAAACACAT GTGTCAGCGG CAGGTGTGTG CCTTTTAACA    300

CAAAATACCC CTATGGTCCT ACTTCTATTG CCGATAATCA GTCGGAAGTA ACTGCAATGC    360

TCAAAGCAGA ATGGGAAGAC TGGAAGAGCA AGAGAATTAA CCTTCGAACG GTGCAGGAGG    420

ATA                                                                 423

(2) INFORMATION FOR SEQ ID NO:28:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (xi) SEQUENCE DESCRIPTION: SEQ ID NO:28:

CCTTTCCTCT GATGCCGTAG TTGGCAGCAT CGCGCAGGGC GTCACCGATG GCCTGACTGA     60

CTACCTGAAG CCTCGCGTCG AAGACCTGCA GCCCAATTCC ATGGCACAGA AGGCACAGAA    120

GGCACAGAAG GCACAGAAGG CACAGAAGGC CAGAAGGCAC AGAAGGCACA              180

GAAGGCACAG AAGGCAATGG CCGGCCTGTC GACCCCGGCA AACACTGTGT CAGCGGCAGG    240

TGTG                                                                244

(2) INFORMATION FOR SEQ ID NO:29:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic (xi) SEQUENCE DESCRIPTION: SEQ ID NO:29:

CCTTTCCTCT GATGCCGTAG TTGGCAGCAT CGCGCAGGGC GTCACCGATG GCCTGACTGA     60

CTACCTGAAG CCTCGCGTCG AAGACCTGCA GCCCAATTCC ATGGCACAGG CACAGGCTCA    120

GGCCAGGCAC AGGCCCAGGC GCAGGCCCAG GCCCAGGCTC AGGCACAGGC GCAGGCGCAG    180

GCACAGGCAC AGGCTCAGGC GCAGGCTCAG GCTCAGGCAA TGGCCGGCCT GTCGACCCCG    240

GCAAACACTG TGTCAGCGGC AGGT                                          264

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: synthetic (xi) SEQUENCE DESCRIPTION: SEQ ID NO:30:

GAGAAGGAAA                                                                              10

(2) INFORMATION FOR SEQ ID NO:31:

(i) SEQUENCE CHARACTERISTICS:
         (A) LENGTH: 324 amino acids
         (B) TYPE: amino acid
         (C) STRANDEDNESS:
         (D) TOPOLOGY: linear (ii) MOLECULE TYPE: protein (vi) ORIGINAL SOURCE:
         (A) ORGANISM: C. glutamicum (xi) SEQUENCE DESCRIPTION: SEQ ID NO:31:

Glu Leu Pro Ala Gly Glu Val Thr Tyr Pro Glu Ile Ala Gly Leu Pro
1               5                   10                  15

Asp Gly Val Arg Val Ile Ser Ala Glu Trp Ala Thr Ser Lys His Val
            20                  25                  30

Ile Leu Thr Ile Gln Ser Ala Ala Met Pro Glu Arg Pro Ile Lys Val
        35                  40                  45

Gln Leu Leu Leu Pro Arg Asp Trp Tyr Ser Ser Pro Asn Arg Glu Phe
50                  55                  60

Pro Glu Ile Trp Ala Leu Asp Gly Leu Arg Ala Ile Glu Glu Gln Ser
65                  70                  75                  80

Gly Trp Thr Ile Glu Thr Asn Ile Glu Gln Tyr Tyr Ala Asp Lys Asn
                85                  90                  95

Ala Ile Val Val Leu Pro Ile Gly Gly Glu Ser Ser Phe Tyr Ser Asp
            100                 105                 110

Trp Glu Glu Pro Asn Asn Gly Lys Asn Tyr Gln Trp Glu Thr Phe Leu
        115                 120                 125

Thr Gln Glu Leu Ala Pro Ile Leu Asp Lys Gly Phe Arg Ser Asn Thr
130                 135                 140

Asp Arg Ala Ile Thr Gly Ile Ser Met Gly Gly Thr Ala Ala Val Asn
145                 150                 155                 160

Ile Ala Thr His His Pro Asp Met Phe Lys Phe Val Gly Ser Phe Ser
                165                 170                 175

Gly Tyr Leu Asp Thr Thr Ser Ala Gly Met Pro Ile Ala Ile Ser Ala
            180                 185                 190

Ala Leu Ala Asp Ala Gly Gly Tyr Asp Ala Asn Ala Met Trp Gly Pro
        195                 200                 205

Val Gly Ser Glu Arg Trp Gln Glu Asn Asp Pro Lys Ser Asn Val Asp
210                 215                 220

Lys Leu Lys Gly Lys Thr Ile Tyr Val Ser Ser Gly Asn Gly Ala Asp
225                 230                 235                 240

Asp Phe Gly Lys Glu Asp Ser Val Ala Ile Gly Pro Ala Asn Ala Thr
                245                 250                 255

Gly Val Gly Leu Glu Val Ile Ser Arg Met Thr Ser Gln Thr Phe Val

-continued

```
                    260                 265                 270
Asp Arg Ala Asn Gln Ala Gly Val Glu Val Val Ala Ser Phe Arg Pro
        275                 280                 285

Ser Gly Val His Ser Trp Glu Tyr Trp Gln Phe Glu Met Thr Gln Ala
    290                 295                 300

Phe Pro His Ile Ala Asn Ala Leu Gly Met Ser Thr Glu Asp Arg Gly
305                 310                 315                 320

Val Glu Cys Ala
```

(2) INFORMATION FOR SEQ ID NO:32:

(i) SEQUENCE CHARACTERISTICS:
        (A) LENGTH: 309 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: M. kansaii (xi) SEQUENCE DESCRIPTION: SEQ ID NO:32:

```
Val Gly Ala Ala Ala Ala Ala Leu Pro Gly Leu Val Gly Leu Ala
1               5                   10                  15

Gly Gly Ala Ala Thr Ala Gly Ala Phe Ser Arg Pro Gly Leu Pro Val
                20                  25                  30

Glu Tyr Leu Gln Val Pro Ser Ala Ala Met Gly Arg Ser Ile Lys Val
            35                  40                  45

Gln Phe Gln Ser Gly Gly Asp Asn Ser Pro Ala Val Tyr Leu Leu Asp
    50                  55                  60

Gly Leu Arg Ala Gln Asp Asp Tyr Asn Gly Trp Asp Ile Asn Thr Pro
65                  70                  75                  80

Ala Phe Glu Trp Tyr Tyr Gln Ser Gly Leu Ser Val Ile Met Pro Val
                85                  90                  95

Gly Gly Gln Ser Ser Phe Tyr Ser Asp Trp Tyr Ser Pro Ala Cys Gly
                100                 105                 110

Lys Ala Gly Cys Thr Thr Tyr Lys Trp Glu Thr Phe Leu Thr Ser Glu
            115                 120                 125

Leu Pro Gln Trp Leu Ser Ala Asn Arg Ser Val Lys Pro Thr Gly Ser
    130                 135                 140

Ala Ala Val Gly Ile Ser Met Ala Gly Ser Ala Leu Ile Leu Ser
145                 150                 155                 160

Val Tyr His Pro Gln Gln Phe Ile Tyr Ala Gly Ser Leu Ser Ala Leu
                165                 170                 175

Met Asp Pro Ser Gln Gly Met Gly Pro Ser Leu Ile Gly Leu Ala Met
            180                 185                 190

Gly Asp Ala Gly Gly Tyr Lys Ala Ser Asp Met Trp Gly Pro Ser Ser
    195                 200                 205

Asp Pro Ala Trp Gln Arg Asn Asp Pro Ser Leu His Ile Pro Glu Leu
    210                 215                 220

Val Ala Asn Asn Thr Arg Leu Trp Ile Tyr Cys Gly Asn Gly Thr Pro
225                 230                 235                 240

Ser Glu Leu Gly Gly Ala Asn Val Pro Ala Glu Phe Leu Glu Asn Phe
                245                 250                 255

Val Arg Ser Ser Asn Leu Lys Phe Gln Asp Ala Tyr Asn Ala Ala Gly
                260                 265                 270
```

```
Gly His Asn Ala Val Phe Asn Leu Asp Ala Asn Gly Thr His Ser Trp
        275                 280                 285

Glu Tyr Trp Gly Ala Gln Leu Asn Ala Met Lys Gly Asp Leu Gln Ala
        290                 295                 300

Ser Leu Gly Ala Arg
305
```

(2) INFORMATION FOR SEQ ID NO:33:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: M. bovis (xi) SEQUENCE DESCRIPTION: SEQ ID NO:33:

```
Ile Gly Thr Ala Ala Ala Val Val Leu Pro Gly Leu Val Gly Leu Ala
1               5                   10                  15

Gly Gly Ala Ala Thr Ala Gly Ala Phe Ser Arg Pro Gly Leu Pro Val
            20                  25                  30

Glu Tyr Leu Gln Val Pro Ser Pro Ser Met Gly Arg Asp Ile Lys Val
        35                  40                  45

Gln Phe Gln Ser Gly Gly Asn Asn Ser Pro Ala Val Tyr Leu Leu Asp
    50                  55                  60

Gly Leu Arg Ala Gln Asp Asp Tyr Asn Gly Trp Asp Ile Asn Thr Pro
65                  70                  75                  80

Ala Phe Glu Trp Tyr Tyr Gln Ser Gly Leu Ser Ile Val Met Pro Val
                85                  90                  95

Gly Gly Gln Ser Ser Phe Tyr Ser Asp Trp Tyr Ser Pro Ala Cys Gly
            100                 105                 110

Lys Ala Gly Cys Gln Thr Tyr Lys Trp Glu Thr Leu Leu Thr Ser Glu
        115                 120                 125

Leu Pro Gln Trp Leu Ser Ala Asn Arg Ala Val Lys Pro Thr Gly Ser
    130                 135                 140

Ala Ala Ile Gly Leu Ser Met Ala Gly Ser Ser Ala Met Ile Leu Ala
145                 150                 155                 160

Ala Tyr His Pro Gln Gln Phe Ile Tyr Ala Gly Ser Leu Ser Ala Leu
                165                 170                 175

Leu Asp Pro Ser Gln Gly Met Gly Leu Ile Gly Leu Ala Met Gly Asp
            180                 185                 190

Ala Gly Gly Tyr Lys Ala Ala Asp Met Trp Gly Pro Ser Ser Asp Pro
        195                 200                 205

Ala Trp Glu Arg Asn Asp Pro Thr Gln Gln Ile Pro Lys Leu Val Ala
    210                 215                 220

Asn Asn Thr Arg Leu Trp Val Tyr Cys Gly Asn Gly Thr Pro Asn Glu
225                 230                 235                 240

Leu Gly Gly Ala Asn Ile Pro Ala Glu Phe Leu Glu Asn Phe Val Arg
                245                 250                 255

Ser Ser Asn Leu Lys Phe Gln Asp Ala Tyr Lys Pro Ala Gly Gly His
            260                 265                 270

Asn Ala Val Phe Asn Phe Pro Pro Asn Gly Thr His Ser Trp Glu Tyr
        275                 280                 285

Trp Gly Ala Gln Leu Asn Ala Met Lys Gly Asp Leu Gln Ser Ser Leu
```

```
              290                 295                 300
Gly Ala Gly
305

(2) INFORMATION FOR SEQ ID NO:34:

(i) SEQUENCE CHARACTERISTICS:
        (A) LENGTH: 313 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: M. leprae (xi) SEQUENCE DESCRIPTION: SEQ ID NO:34:

Leu Leu Val Gly Ala Ala Thr Leu Pro Ser Leu Ile Ser Leu Ala
1               5                  10                  15

Gly Gly Ala Ala Thr Ala Ser Ala Phe Ser Arg Pro Gly Leu Pro Val
            20                  25                  30

Glu Tyr Leu Gln Val Pro Ser Glu Ala Met Gly Arg Thr Ile Lys Val
        35                  40                  45

Gln Phe Gln Asn Gly Gly Asn Gly Ser Pro Ala Val Tyr Leu Leu Asp
    50                  55                  60

Gly Leu Arg Ala Gln Asp Asp Tyr Asn Gly Trp Asp Ile Asn Thr Ser
65                  70                  75                  80

Ala Phe Glu Trp Tyr Tyr Gln Ser Gly Leu Ser Val Val Met Pro Val
                85                  90                  95

Gly Gly Gln Ser Ser Phe Tyr Ser Asp Trp Tyr Ser Pro Ala Cys Gly
            100                 105                 110

Lys Ala Gly Cys Thr Thr Tyr Lys Trp Glu Thr Phe Leu Thr Ser Glu
        115                 120                 125

Leu Pro Lys Trp Leu Ser Ala Asn Arg Ser Val Lys Ser Thr Gly Ser
    130                 135                 140

Ala Val Val Gly Leu Ser Met Ala Gly Ser Ser Ala Leu Ile Leu Ala
145                 150                 155                 160

Ala Tyr His Pro Asp Gln Phe Ile Tyr Ala Gly Ser Leu Ser Ala Leu
                165                 170                 175

Met Asp Ser Ser Gln Gly Ile Glu Pro Gln Leu Ile Gly Leu Ala Met
            180                 185                 190

Gly Asp Ala Gly Gly Tyr Lys Ala Ala Asp Met Trp Gly Pro Pro Asn
        195                 200                 205

Asp Pro Ala Trp Gln Arg Asn Asp Pro Ile Leu Gln Ala Gly Lys Leu
    210                 215                 220

Val Ala Asn Asn Thr His Leu Trp Val Tyr Cys Gly Asn Gly Thr Pro
225                 230                 235                 240

Ser Glu Leu Gly Gly Thr Asn Val Pro Ala Glu Phe Leu Glu Asn Phe
                245                 250                 255

Val His Gly Ser Asn Leu Lys Phe Lys Asp Ala Tyr Asn Gly Ala Gly
            260                 265                 270

Gly His Asn Ala Val Phe Asn Leu Asn Ala Asp Gly Thr His Ser Trp
        275                 280                 285

Glu Tyr Trp Gly Ala Gln Leu Asn Ala Met Lys Pro Asp Leu Gln Asn
    290                 295                 300

Thr Leu Met Ala Val Pro Arg Ser Gly
305                 310
```

-continued (2) INFORMATION FOR SEQ ID NO:35:

(i) SEQUENCE CHARACTERISTICS:
(A) LENGTH: 308 amino acids
(B) TYPE: amino acid
(C) STRANDEDNESS:
(D) TOPOLOGY: linear (ii) MOLECULE TYPE: protein (vi) ORIGINAL SOURCE:
(A) ORGANISM: M. tuberculosis (xi) SEQUENCE DESCRIPTION: SEQ ID NO:35:

```
Ile Ala Ala Met Gly Ala Val Leu Val Tyr Gly Leu Val Gly Thr Phe
1               5                   10                  15

Gly Gly Pro Ala Thr Ala Gly Ala Phe Ser Arg Pro Gly Leu Pro Val
            20                  25                  30

Glu Tyr Leu Gln Val Pro Ser Ala Ser Met Gly Arg Asp Ile Lys Val
        35                  40                  45

Gln Phe Gln Gly Gly Gly Pro His Ala Val Tyr Leu Leu Asp Gly Leu
    50                  55                  60

Arg Ala Gln Asp Asp Tyr Asn Gly Trp Asp Ile Asn Thr Pro Ala Phe
65                  70                  75                  80

Glu Glu Tyr Tyr Gln Ser Gly Leu Ser Val Ile Met Pro Val Gly Gly
                85                  90                  95

Gln Ser Ser Phe Tyr Thr Asp Trp Tyr Gln Pro Ser Gln Ser Asn Gly
            100                 105                 110

Gln Asn Tyr Thr Tyr Lys Trp Glu Thr Phe Leu Thr Arg Glu Met Pro
        115                 120                 125

Ala Trp Leu Gln Ala Asn Lys Gly Val Ser Pro Thr Gly Asn Ala Ala
    130                 135                 140

Val Gly Leu Ser Met Ser Gly Gly Ser Ala Leu Ile Leu Ala Ala Tyr
145                 150                 155                 160

Tyr Pro Gln Gln Phe Pro Tyr Ala Ala Ser Leu Ser Gly Phe Leu Asn
                165                 170                 175

Pro Ser Glu Gly Trp Trp Pro Thr Leu Ile Gly Leu Ala Met Asn Asp
            180                 185                 190

Ser Gly Gly Tyr Asn Ala Asn Ser Met Trp Gly Pro Ser Ser Asp Pro
        195                 200                 205

Ala Trp Lys Arg Asn Asp Pro Met Val Gln Ile Pro Arg Leu Val Ala
    210                 215                 220

Asn Asn Thr Arg Ile Trp Val Tyr Cys Gly Asn Gly Thr Pro Ser Asp
225                 230                 235                 240

Leu Gly Gly Asp Asn Ile Pro Ala Lys Phe Leu Glu Gly Leu Thr Leu
                245                 250                 255

Arg Thr Asn Gln Thr Phe Arg Asp Thr Tyr Ala Ala Asp Gly Gly Arg
            260                 265                 270

Asn Gly Val Phe Asn Phe Pro Pro Asn Gly Thr His Ser Trp Pro Tyr
        275                 280                 285

Trp Asn Glu Gln Leu Val Ala Met Lys Ala Asp Ile Gln His Val Leu
    290                 295                 300

Asn Gly Ala Thr
305
```

(2) INFORMATION FOR SEQ ID NO:36:

(i) SEQUENCE CHARACTERISTICS:
    (A) LENGTH: 321 amino acids
    (B) TYPE: amino acid
    (C) STRANDEDNESS:
    (D) TOPOLOGY: linear (ii) MOLECULE TYPE: protein (vi) ORIGINAL SOURCE:
    (A) ORGANISM: M. bovis (xi) SEQUENCE DESCRIPTION: SEQ ID NO:36:

```
Arg Leu Val Val Gly Ala Val Gly Ala Ala Leu Val Ser Gly Leu Val
 1               5                  10                  15

Gly Ala Val Gly Gly Thr Ala Thr Ala Gly Ala Phe Ser Arg Pro Gly
            20                  25                  30

Leu Pro Val Glu Tyr Leu Gln Val Pro Ser Pro Ser Met Gly Arg Asp
        35                  40                  45

Ile Lys Val Gln Phe Gln Ser Gly Gly Ala Asn Ser Pro Ala Leu Tyr
    50                  55                  60

Leu Leu Asp Gly Leu Arg Ala Gln Asp Asp Phe Ser Gly Trp Asp Ile
65                  70                  75                  80

Asn Thr Pro Ala Phe Glu Trp Tyr Asp Gln Ser Gly Leu Ser Val Val
                85                  90                  95

Met Pro Val Gly Gly Gln Ser Ser Phe Tyr Ser Asp Trp Tyr Gln Pro
            100                 105                 110

Ala Cys Gly Lys Ala Gly Cys Gln Thr Tyr Lys Trp Glu Thr Phe Leu
        115                 120                 125

Thr Ser Glu Leu Pro Gly Trp Leu Gln Ala Asn Arg His Val Lys Pro
    130                 135                 140

Thr Gly Ser Ala Val Val Gly Leu Ser Met Ala Ala Ser Ser Ala Leu
145                 150                 155                 160

Thr Leu Ala Ile Tyr His Pro Gln Gln Phe Val Tyr Ala Gly Ala Met
                165                 170                 175

Ser Gly Leu Leu Asp Pro Ser Gln Ala Met Gly Pro Thr Leu Ile Gly
            180                 185                 190

Leu Ala Met Gly Asp Ala Gly Gly Tyr Lys Ala Ser Asp Met Trp Gly
        195                 200                 205

Pro Lys Glu Asp Pro Ala Trp Gln Arg Asn Asp Pro Leu Leu Asn Val
    210                 215                 220

Gly Lys Leu Ile Ala Asn Asn Thr Arg Val Trp Val Tyr Cys Gly Asn
225                 230                 235                 240

Gly Lys Pro Ser Asp Leu Gly Gly Asn Asn Leu Pro Ala Lys Phe Leu
                245                 250                 255

Glu Gly Phe Val Arg Thr Ser Asn Ile Lys Phe Gln Asp Ala Tyr Asn
            260                 265                 270

Ala Gly Gly Gly His Asn Gly Val Phe Asp Phe Pro Asp Ser Gly Thr
        275                 280                 285

His Ser Trp Glu Tyr Trp Gly Ala Gln Leu Asn Ala Met Lys Pro Asp
    290                 295                 300

Leu Gln Arg Ala Leu Gly Ala Thr Pro Asn Thr Gly Pro Ala Pro Gln
305                 310                 315                 320

Gly
```

(2) INFORMATION FOR SEQ ID NO:37:

(i) SEQUENCE CHARACTERISTICS:
        (A) LENGTH: 321 amino acids

-continued

```
        (B)  TYPE: amino acid
        (C)  STRANDEDNESS:
        (D)  TOPOLOGY: linear (ii) MOLECULE TYPE: protein (vi) ORIGINAL SOURCE:
        (A) ORGANISM: M. tuberculosis (xi) SEQUENCE DESCRIPTION: SEQ ID NO:37:

Arg Arg Leu Val Val Gly Ala Val Ala Arg Leu Val Ser Gly Leu Val
1               5                   10                  15

Gly Ala Val Gly Gly Thr Ala Thr Ala Gly Ala Phe Ser Arg Pro Gly
                20                  25                  30

Leu Pro Val Glu Tyr Leu Gln Val Pro Ser Pro Ser Met Gly Arg Asp
            35                  40                  45

Ile Lys Val Gln Phe Gln Ser Gly Gly Ala Asn Ser Pro Ala Leu Tyr
        50                  55                  60

Leu Leu Asp Gly Leu Arg Ala Gln Asp Asp Phe Ser Gly Trp Asp Ile
65                  70                  75                  80

Asn Thr Pro Ala Phe Glu Trp Tyr Asp Gln Ser Gly Leu Ser Val Val
                85                  90                  95

Met Pro Val Gly Gly Gln Ser Ser Phe Tyr Ser Asp Trp Tyr Gln Pro
                100                 105                 110

Ala Cys Arg Lys Ala Gly Cys Gln Thr Tyr Lys Trp Glu Thr Phe Leu
            115                 120                 125

Thr Ser Glu Leu Pro Gly Trp Leu Gln Ala Asn Arg His Val Lys Pro
            130                 135                 140

Thr Gly Ser Ala Val Val Gly Leu Ser Met Ala Ala Ser Ser Ala Leu
145                 150                 155                 160

Thr Leu Ala Ile Tyr His Pro Gln Gln Phe Val Tyr Ala Gly Ala Met
                165                 170                 175

Ser Gly Leu Leu Asp Pro Ser Gln Ala Met Gly Pro Thr Leu Ile Gly
                180                 185                 190

Leu Ala Met Gly Asp Ala Gly Gly Tyr Lys Ala Ser Asp Met Trp Gly
            195                 200                 205

Pro Lys Glu Asp Pro Ala Trp Gln Arg Asn Asp Pro Leu Leu Asn Val
            210                 215                 220

Gly Lys Leu Ile Ala Asn Asn Thr Arg Val Trp Val Tyr Cys Gly Asn
225                 230                 235                 240

Gly Lys Pro Ser Asp Leu Gly Gly Asn Asn Leu Pro Ala Lys Phe Leu
                245                 250                 255

Glu Gly Phe Val Arg Thr Ser Asn Ile Lys Phe Gln Asp Ala Tyr Asn
                260                 265                 270

Ala Gly Gly Arg His Asn Gly Val Phe Asp Phe Pro Asp Ser Gly Thr
                275                 280                 285

His Ser Trp Glu Tyr Trp Gly Ala Gln Leu Asn Ala Met Lys Pro Asp
            290                 295                 300

Leu Gln Arg His Trp Val Pro Arg Pro Thr Pro Gly Pro Pro Gln Gly
305                 310                 315                 320

Ala
```

SYSTEM FOR PROTEIN EXPRESSION AND SECRETION ESPECIALLY IN CORYNEBACTERIA

This application is a continuation of application Ser. No. 08/039,028, filed Mar. 29, 1993, abandoned, which is a 371 of PCT/FR92/00744 filed Jul. 29, 1992.

The present invention relates especially to systems for expression and secretion of proteins which can be used in particular in corynebacteria, as well as to a method using these systems, as well as to new proteins associated with these expression systems.

Corynebacteria constitute a group of Gram-positive bacteria, of irregular morphology, which is represented by a wide variety of strains.

In spite of the fact that Gram-positive cells have a simple structure which facilitates the secretion of proteins into the external medium, the secretion of proteins by corynebacteria has not been very widely studied up until now. Only the diphtheria toxin secreted by certain strains of Corynebacterium diphtheriae infected by tox+ lysogenic phages (Smith 1980: J. Bacteriol. 141 pp 1142; Smith et al. 1980: J. Bacteriol. 141 pp 184; Greenfield et al. 1983: PNAS USA 80 pp 6853) and the study of the nucleotide sequence of a gene involved in the secretion of a DNase by Corvnebacterium alutamicum (W. Liebl et A.S. Sinksey 1986: Genetics and Biotechnology of Bacteria, Vol. 2 pp 383–388) have been reported.

American Patent U.S. Pat. No. 4,965,197 describes a system for expression and secretion which can be used in Corynebacterium on the basis of the DNAse described above; however, it appears that this protein is not predominant and that under these conditions, the corresponding system for secretion is not very important.

Accordingly, the invention relates to a system for expression and secretion in a bacterium of the corynebacterium type containing the elements for the secretion of two proteins which are predominant in the culture supernatant of certain corynebacteria.

It relates especially to a system for expression/secretion of a given amino acid, polypeptide or protein by a strain of corynebacterium, characterized in that the sequence which encodes the said amino acid, polypeptide or the said protein is situated in a region of chromosomal or plasmid DNA where the said sequence is transcribed with towards the 5' end at least one portion of the sequence encoding the signal sequence of the protein PS1 or PS2, the said portion ensuring the secretion of the said amino acid, polypeptide or of the said protein after translation when the system is incorporated into the said strain of corynebacterium.

More particularly, the present invention relates to a system for expression and secretion of a corynebacterium comprising:

- a strain of corynebacterium,
- a secretion cassette containing a first functional DNA sequence for expression in the said strain of corynebacterium, a second DNA sequence which encodes an amino acid, a polypeptide and/or a protein, and a third DNA sequence inserted between the said first and second DNA sequences which encode the elements of a protein chosen from PS1 or PS2, which ensure the secretion of the said amino acids, polypeptides and/or proteins by the said strain of corynebacterium.

Firstly, it should be understood that within the framework of the present invention, the term "corynebacterium" designates not only strains of the genus Corynebacterium but also related bacteria such as Brevibacterium.

The expression system of the present invention may be present in a plasmid which replicates autonomously in corynebacteria and in this case, the plasmid will contain a replication origin which is functional in the strain, for example in Corynebacterium a replication origin PBL 1, but may also be carried by a nonreplicative plasmid designed especially for chromosomal integration, in this case the plasmid will contain the elements permitting chromosomal recombination and integration; in the case of integration, the expression system will be finally present in the chromosome of the bacterium in question.

In particular, in the case of chromosomal integration, it has been possible to demonstrate that the insertion of a heterologous DNA sequence into the gene csp1 encoding PS1 or csp2 encoding PS2 did not affect the growth of the corresponding strain. Under these conditions, it is possible to integrate a sequence encoding an amino acid, a polypeptide or a protein in phase in csp1 or csp2 so as to obtain the expression/secretion of the products of expression of the inserted coding sequence.

Among the functional DNA sequences for the expression in the strain of corynebacterium, there should be mentioned both the elements for homologous expression and the elements for heterologous expression, that is to say that they can be elements which already exist in the host bacterium or alternatively which on the contrary are derived from a different bacterium.

These expression elements will essentially contain a promoter and a ribosome-binding site, but it is also possible to provide for other elements especially elements of the type for regulating the expression.

Among the expression elements which can be used in corynebacteria, there will be used more particularly the Ptac promoter which is a strong promoter, a trp/lac hybrid which is inducible by IPTG and is shown to be functional in corynebacteria such as E. coli; but it is possible to use other promoters, for example, as will be described below, promoters or other elements for the expression of the structural gene of corynebacteria, for example the gdha promoter. It is also possible to provide for the use of, for example, the expression elements, especially the promoter for one of the proteins PS1 and/or PS2, as identified within the framework of the present invention.

The expression elements may also contain DNA sequences ensuring the regulation of the expression of the genes downstream.

Among the elements ensuring good expression, provision can be made for the possibility of placing at the end of the coding sequence a translational stop element, in the form of one or more stop codons, or a transcriptional stop element.

Among the elements ensuring the secretion, there should be mentioned, as indicated above, all or a portion of the signal sequence of one of the proteins PS1 or PS2 as well as the equivalents of these sequences, without modification or loss of the secretion property.

Finally, it is certain that it is possible to make, using known techniques such as point mutations, minor modifications to the secretion sequences while preserving the same type of secretion property, accordingly, the present invention is also intended to cover these equivalent sequences.

Finally, the expression system of the present invention may contain other elements, especially elements such as transcription terminators, for example the terminator for proteins PS1 and/or PS2, or for gdhA.

In certain cases, it may be advantageous to incorporate into the expression and secretion sequences all or a portion of protein PS1 in order to obtain fused proteins whose secretion and level of expression can be improved under these conditions.

The expression systems according to the invention may contain heterologous elements which permit construction in bacteria different from corynebacteria for example as mentioned above a replication origin which is functional in *E. coli* but also other elements such as a marker gene which may facilitate the transfer into Corynebacterium.

The marker gene may, of course, be of very varied type as long as it is functional in corynebacteria, it may be a gene for positive or negative selection such as a specific resistance, however, under the current state of research, these genes are not easily available. The celA gene for *Clostridium thermocellum* cellulase (celA) which confers the $CMC^+$ phenotype will therefore preferably be used, but it is possible to use other marker genes, especially lacZ of *E. coli*.

In the case where the marker gene is celA, the transformant bacteria are selected for the $CMC^+$ character after insertion of the coding sequence into an appropriate restriction site such as BstXI.

In the method according to the invention, provision will preferably be made to allow the marker gene to be easily eliminated after checking the construct especially by placing restriction sites between the marker gene and the coding sequence.

The coding sequence may be natural, synthetic or mixed.

The expression and the secretion system of the present invention is of course designed more particularly to ensure the production of products of industrial importance, accordingly, the coding sequences will encode more particularly a peptide, a polypeptide or a protein of industrial importance but it may also be a sequence not directly encoding a protein of industrial importance, but a protein which may be involved in the maturation and/or the production of an amino acid, a polypeptide or a protein which is of industrial importance.

The methods according to the invention are more particularly designed for the expression of amino acid sequences, especially repetitive sequences, they are therefore mainly synthetic sequences.

This second DNA sequence encoding these different products may also contain certain elements designed to ensure the maturation of the secreted product.

In the case of a synthetic sequence, the choice of the coding sequence permits the constitution:

of any amino acid sequence;

of a repetitive amino acid sequence with n repetitions of the type $(aa_1 \ldots aa_x)n$;

of a repetitive sequence containing in the COOH-terminal position $aa_x$ a positively- or negatively-charged amino acid. This amino acid can make it possible to improve genetic expression but it advantageously makes it possible (i) to isolate the polypeptide due to its marked ionic character;

(ii) to cleave by means of a specific protein the polypeptide into $(aa_1 \ldots aa_x)$ units;

(iii) to remove if necessary the terminal amino acid $aa_x$ by means of specific carboxypeptidases;

of a repetitive sequence containing in the $NH_2$- or COOH-terminal portion $aa_1$ or $aa_x$ an amino acid conferring a desired advantage. In the examples, the expressed sequence encodes a polypeptide of the structure $(ala\text{-}gln)_{20}$ and $(ala\text{-}gln\text{-}lys)_{10}$. The ala-gln or ala-gln-lys sequence can be released by subsequent enzymatic treatment. Other polymers of this type such as Ala-Gln-Tyr or Ala-Gln-Met may be provided which can be released by enzymatic or chemical treatment.

The choice of codons of the coding sequence can influence the expression in corynebacteria, it is preferably advisable to provide for a sequence having a GC content of the order of 50 to 60%.

In the case of the example, the sequence encoding $(AQ)_{20}$ is GCX CAG with X=A or T or C or G; indeed, while none of the codons is preferred for alanine, on the other hand, the CAG codon is very clearly preferred for glutamine. In this case, the percentage of GC is of the order of 75%, which may constitute a limitation, accordingly, the use of polymers containing 3 amino acids in which the third is rich in A and T is envisaged in order to reduce the percentage to 55%.

Tyr, Lys and Met possess two A or T in the first two bases of their codon and therefore make it possible to reduce the percentage of GC from 75% to about 60%, which becomes closer to the percentage of GC found in corynebacteria. Moreover, of course, the industrial importance of these two amino acids in the COOH-terminal position of glutamine (Q) has been considered and exists.

The present invention also relates to strains of corynebacteria containing an expression and secretion system as described above, and more particularly when the strain is a Brevibacterium especially a strain of *Brevibacterium lactofermentum*.

Finally, the present invention relates to a method for producing amino acids, polypeptides or proteins, characterized in that there is cultured in a culture medium a transformant strain of corynebacterium as described above, in which the second DNA sequence encodes the said amino acids, the said polypeptide and/or the said protein and in that the said product is optionally separated from the culture medium after culturing. Indeed, by means of this method, the useful product was secreted and is therefore present in the culture medium from which it can be isolated by known methods, whether they are separation techniques, such as chromatography, selective precipitation for example, it being obviously necessary for the latter to be adapted to the nature of the molecule produced.

It is also possible to provide for the separation of the bacterial concentrate, then the separation of the given protein, fused or otherwise with PS1 or PS2 from this concentrate, for example using a surface-active agent. Indeed, PS1 and PS2 being parietal proteins, a portion of the proteins secreted with this system remains anchored in the wall, which can facilitate their separation since the bacterium is not lysed with certain detergents.

The transformation of corynebacteria with plasmids is preferably carried out by electroporation (Bonamy C., Guyonvarch A., Reyes, O., David F. and Leblon G. (1990) FEMS Microbiology Letters 66: 263–270) or by any other appropriate method.

The fermentation conditions which permit the preparation of amino acids, peptides and/or proteins obviously depend on the type of product obtained as well as the specific strain used, these are elements which must be specifically determined for each strain according to the knowledge of the person skilled in the art.

The present invention also relates to expression systems containing all or a portion of the signals for the expression of csp1, csp2 and gdhA or all or a portion of these three genes, as well as strains expressing this type of system, especially strains of corynebacteria.

In the methods using the constructs described, the expression/secretion of the given amino acid, polypeptide or protein will be regulated by the temperature, the culture medium and/or the nature of the sugars for PS1 and PS2 and the concentration of salts (especially $NH_4^+$), metabolites (glutamate) and sugars (glucose/fructose) for the systems with gdhA.

The present invention also relates to the proteins containing all or a portion of the PS1 or PS2 sequence, in particular containing one or more antigenic sites of these proteins. The said proteins can also be used by way of a typical element, especially in diagnostic kits, as well as the corresponding antibodies.

The invention also relates to the strains of corynebacteria in which the given protein is anchored on the wall of the PS1 or PS2 portion fulfilling this anchoring function or alternatively in which the antigenic epitopes of PS1 or PS2 are exposed on the wall.

The examples below are designed to show other characteristics and advantages of the present invention and are not in any way limiting.

Figure 1:
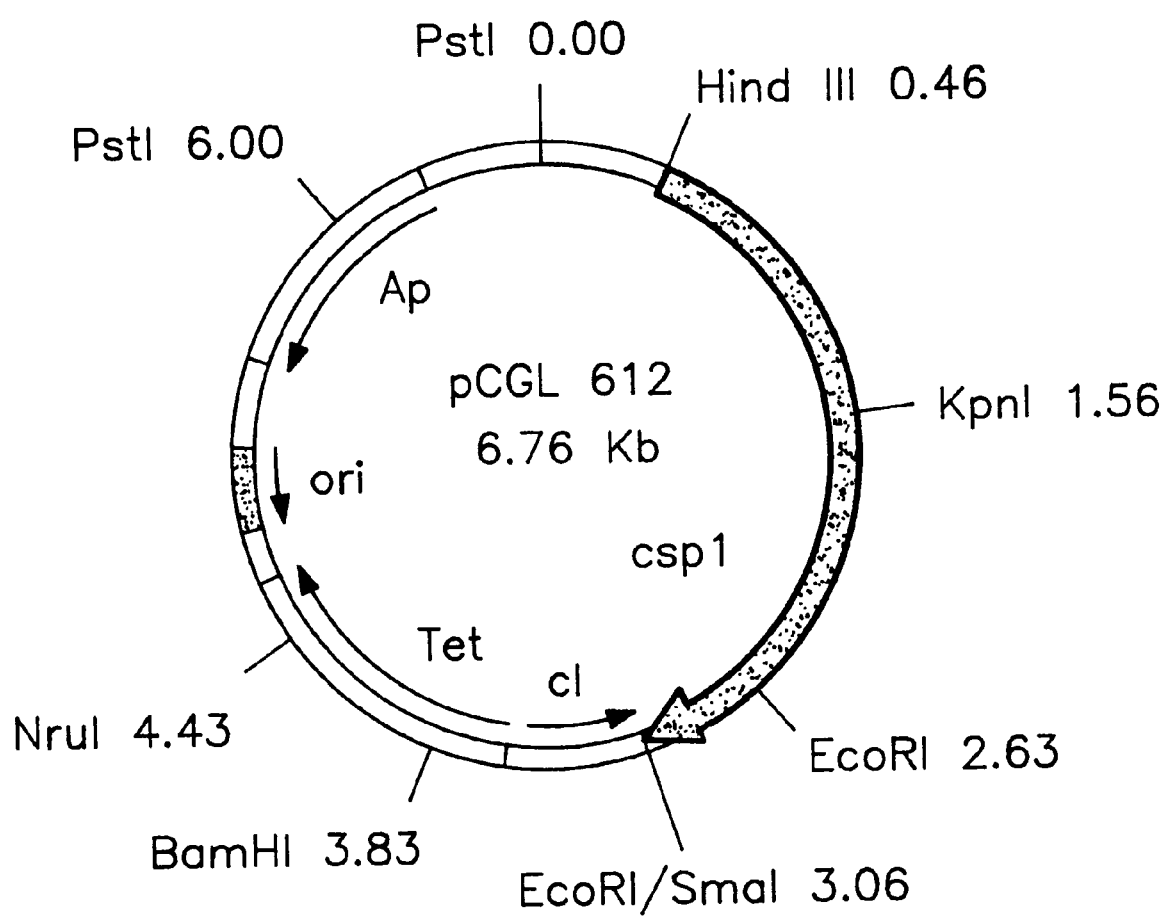

FIG. 1. Diagram of the plasmid pCGL612. Plasmid derived from pUN121 (Nilsson, B., Uhlen, M., Josephson, S., Gatenbeck, S., and Philipson, L. (1983) An improved positive selection plasmid vector constructed by oligonucleotide mediated mutagenesis. Nucleic Acids Res 11: 8019–8029.) containing a 2.6-kb fragment of *C. melassecola* ATCC17965 containing the entire cspl gene which permits the synthesis of protein PS1.

FIG. 2(SEQ ID NO: 1). Nucleotide sequence (SEQ ID NO: 1) and corresponding amino acid sequence (SEQ ID NO: 1) (SEQ ID NO: 2) of the csp1 gene of *Corynebacterium glutamicum* termed *Corynebacterium melassecola* ATCC17965. The numbering of the nucleotides is present on the right-hand side of the figure. The repetitive nucleotide sequences are boxed. The probable Shine-Dalgarno sequence is underlined. A 24-bp palindrome which probably corresponds to the transcription terminator is indicated by opposite arrows. This sequence appears in the EMBL nucleotide sequence data bank under the accession number X66078.

Figure 3:
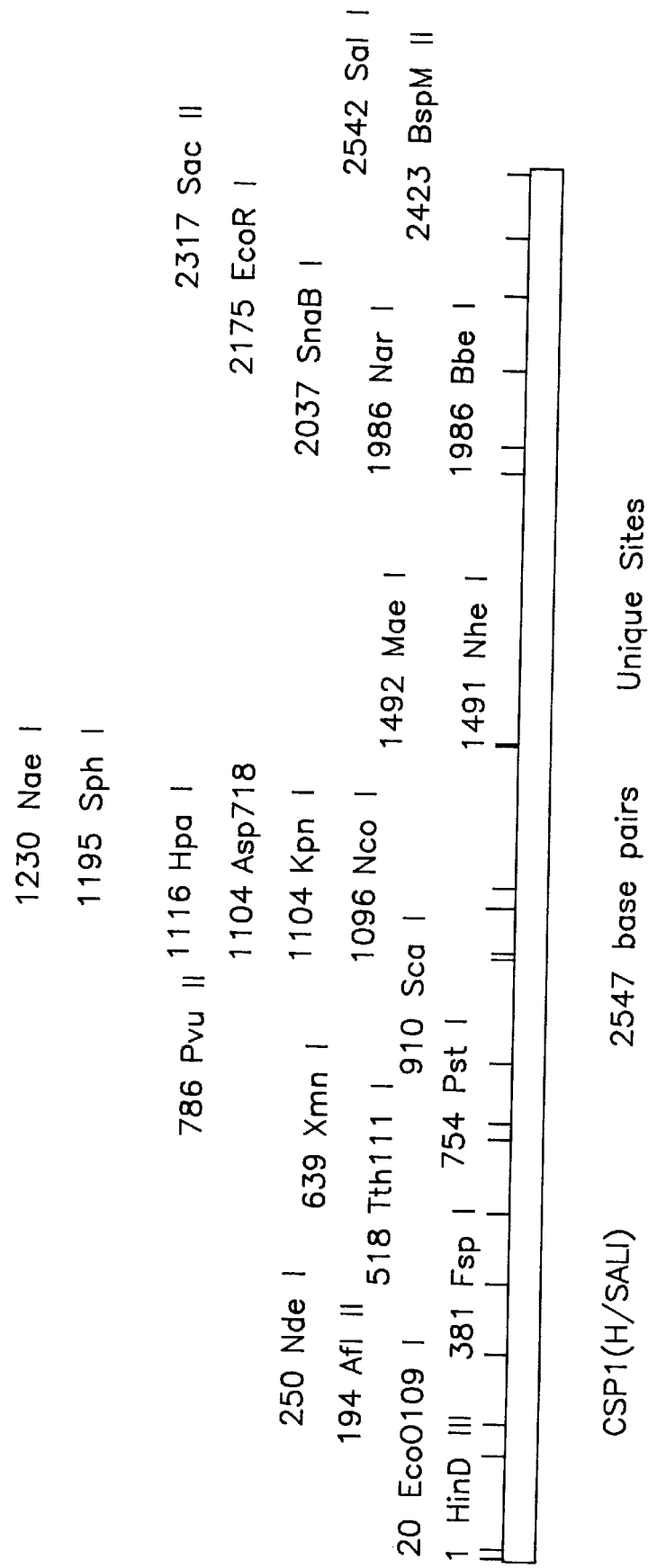

FIG. 3. Restriction map of the sequenced DNA region of *C. melassecola* ATCC17965 carrying csp1.

Figure 4A:
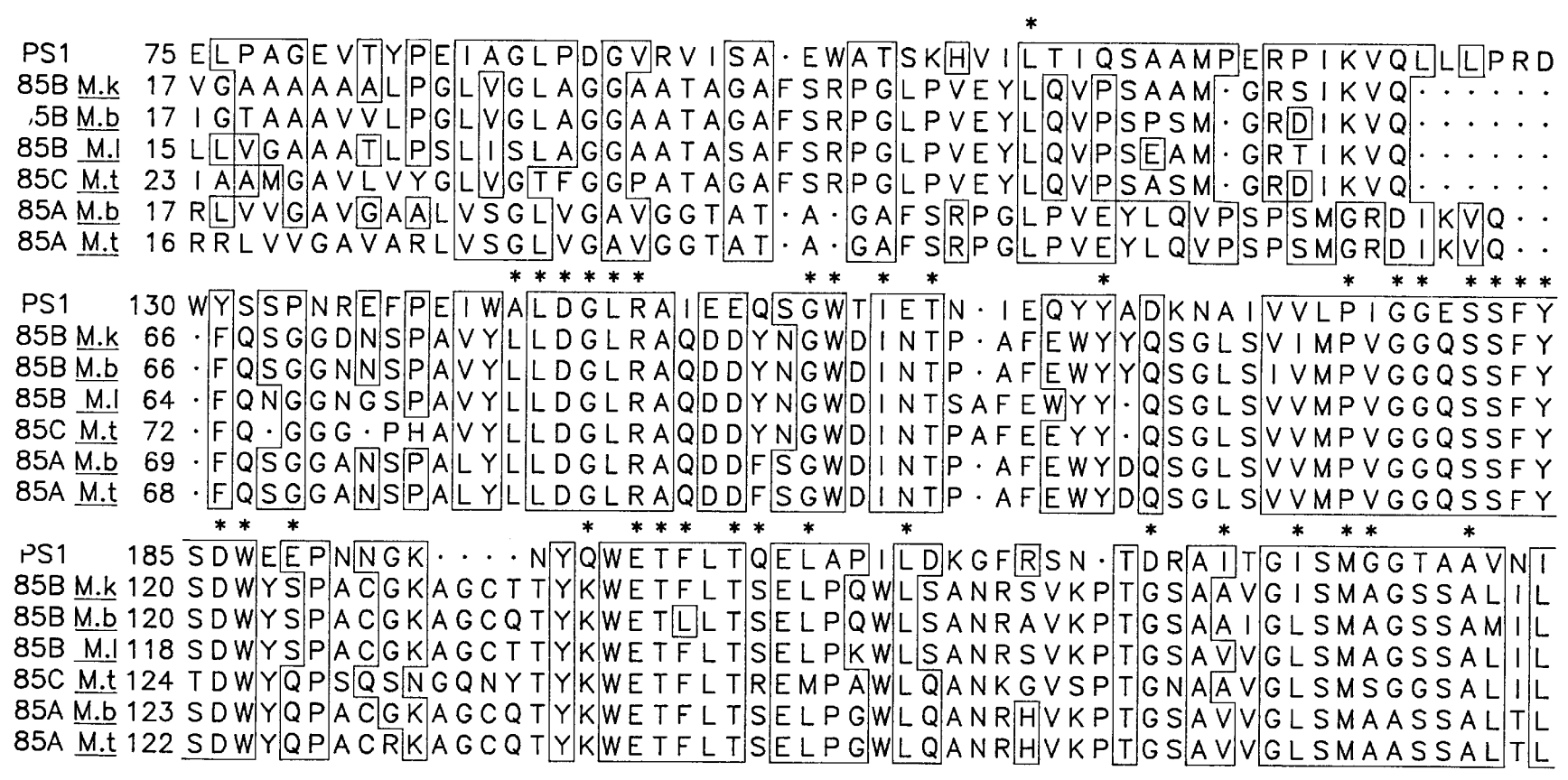
Figure 4B:
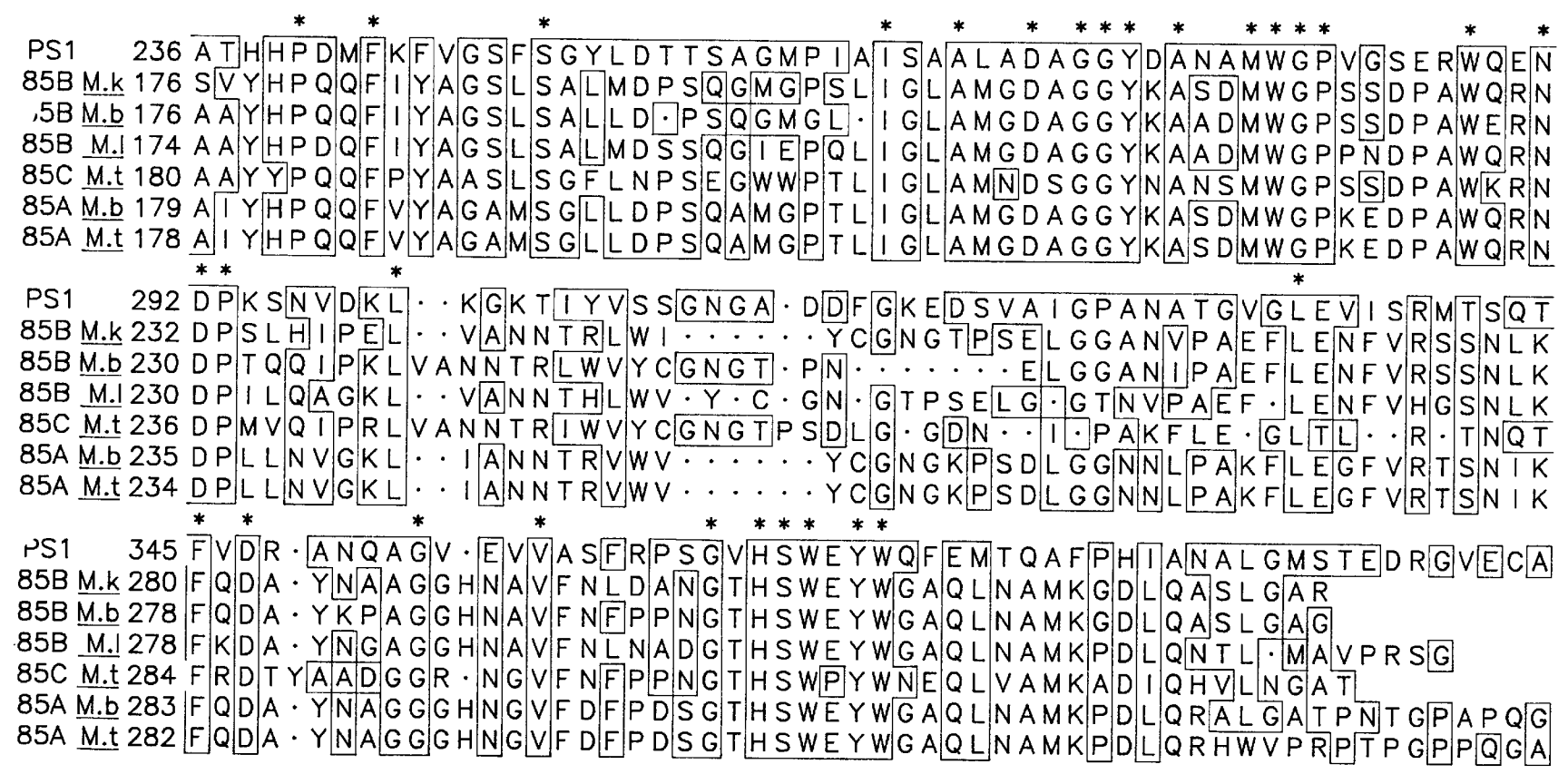

FIGS. 4A and 4B. Alignment of the sequences of protein PS1 of *C. glutamicum* (SEQ ID NO: 2) and of the proteins of the antigen 85 complex of Mycobacterium. 85B M. k. (SEQ ID NO: 32) represents antigen 85-B of M. kansaii (MIPSG16235). 85B M. b. (SEQ ID NO: 33) represents antigen 85-B of M. bovis (MIPSC83179). 85B M. l (SEQ ID NO: 34) represents antigen 85-B of M. leprae (EMBLX60934). 85C M. t. (SEQ ID NO: 35) represents antigen 85-C of M. tuberculosis (EMBLX57229). 85A M. b. (SEQ ID NO: 36) represents antigen 85-A of M. bovis (MIPSA28544). 85A M. t. (SEQ ID NO: 37) represents antigen 85-A of M. tuberculosis (MIPSI60062). The sequences were aligned using the FastA programme of "Genetics Computer Group" (University of Wisconsin, USA). The numbering of the residues is given for each protein at the beginning of each line. Similar amino acid residues found between the different proteins are boxed. The residues considered as similar are the following: acids or amides (D, E, N, Q); basic (H, K, R); polar (P, A, G, S, T); nonpolar (I, L, M, V) and aromatic (F, W, Y). The amino acid residues identical between the seven proteins are indicated by a star above the relevant residues. remark: for each antigen, the accession number is specified associated with the name of the data bank in question and appear in brackets.

Figure 5:
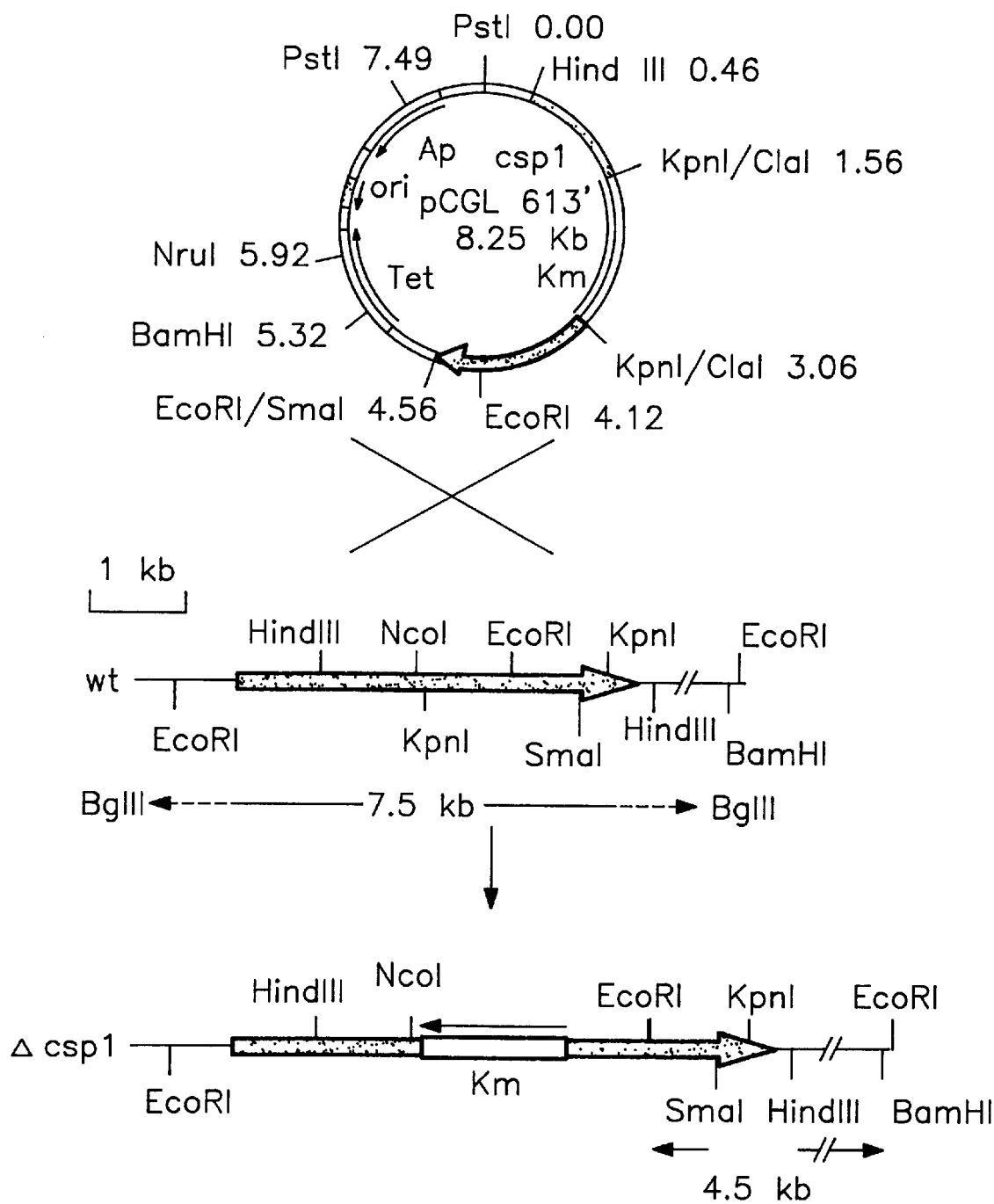

FIG. 5. Interruption of the csp1 gene. Integration into the chromosome of an interrupted csp1 gene. pCGL613' is nonreplicative in *C. glutamicum*, it contains csp1 (dark zone) interrupted by the aphA3 gene (Km). wt, *B. lactofermentum* 15 wild-type and Δcsp1, integrant containing interrupted csp1.

FIG. 6. Construction of the plasmid pCGL616. The plasmid pCGL616 corresponds to the plasmid pCGL125 equipped with the csp1 gene of *C. glutamicum*.

Figure 7:
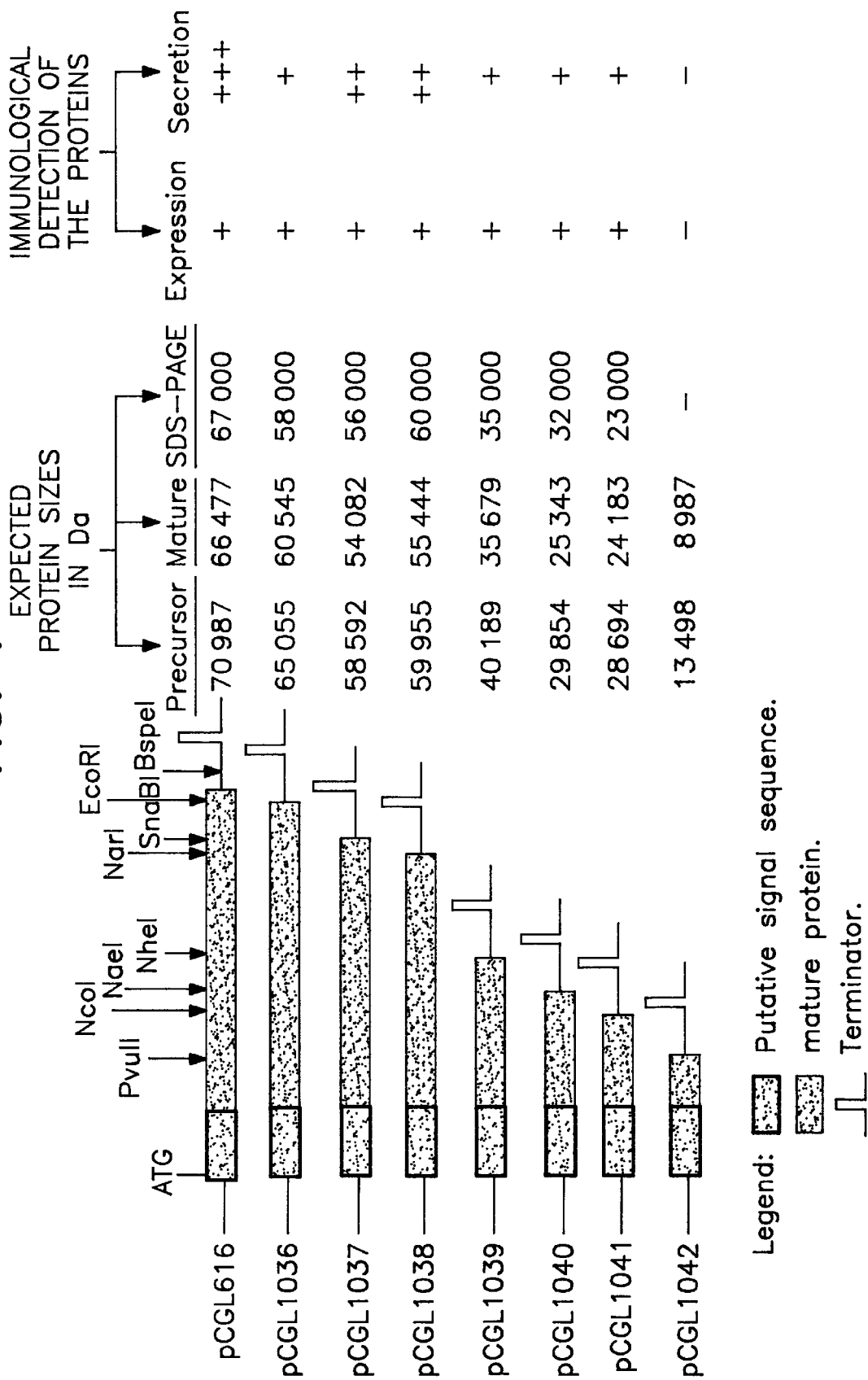

FIG. 7. Plasmids which make it possible to synthesize truncated proteins PS1. Diagram of the vectors derived from pCGL616, specification of the size of the expected proteins and their detection (+) or otherwise (–) by Western blotting with anti-PS1 polyclonal antibodies.

Figure 8:
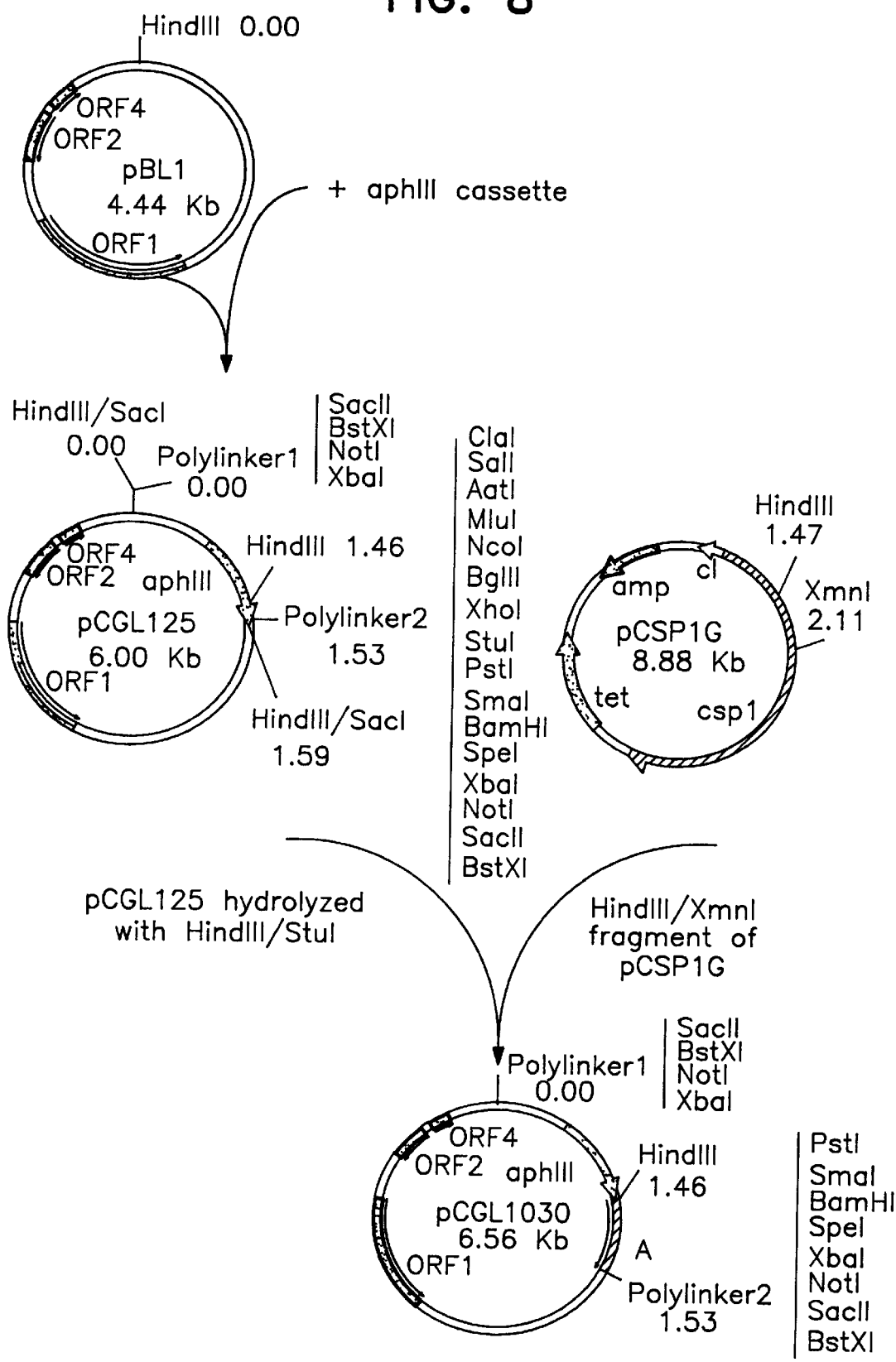

FIG. 8. Construction of the plasmid pCGL1030. The region named A in the diagram contains the promoter of csp1 followed by the DNA region corresponding to the signal sequence of PS1 and the first 30 amino acids of its mature sequence.

Figure 9:
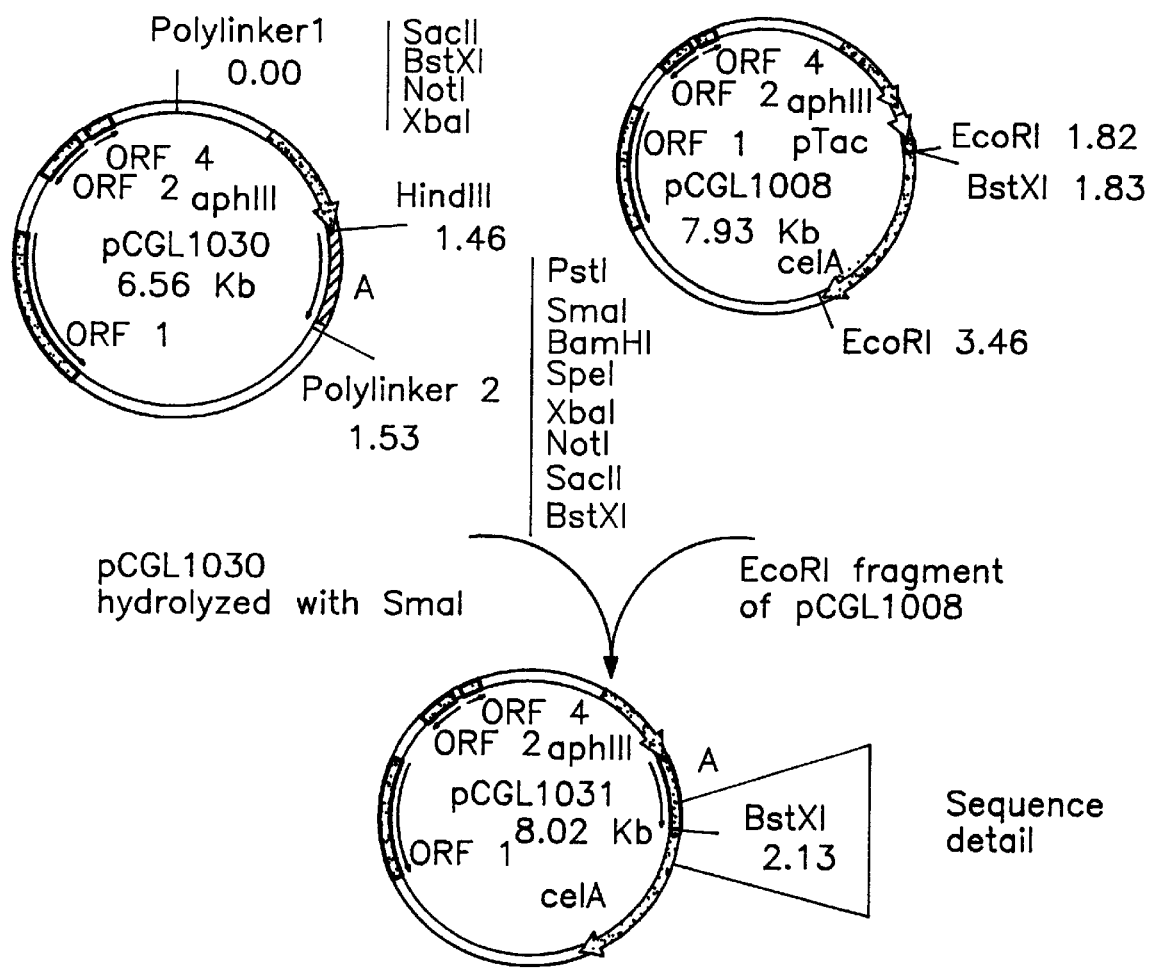

FIG. 9. Construction of the plasmid 1031. The region named A is described in FIG. 8. The junction region between PS1 and EGA has been sequenced and this sequence detail is presented.

Figure 10:
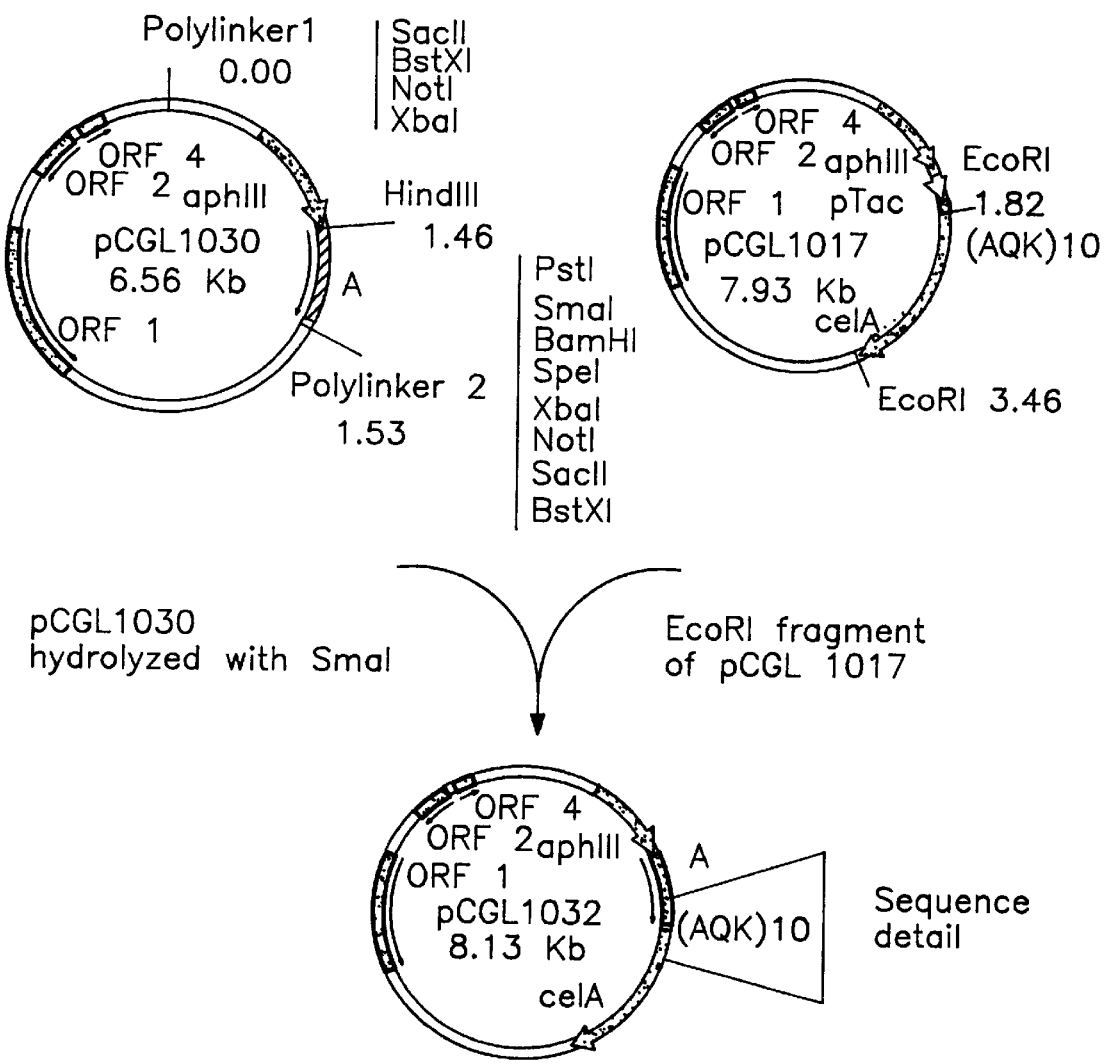

FIG. 10. Construction of the plasmid 1032. The region named A is described in FIG. 8. The junction region between PS1, (AQK)10 and EGA has been sequenced and this sequence detail is presented.

FIG. 11. Construction of the plasmid 1033. The region named A is described in FIG. 8. The junction region between PS1, (AQ)19 and EGA has been sequenced and this sequence detail is presented.

FIG. 12 (SEQ ID NO: 3). Nucleotide sequence (SEQ ID NO: 3) and the corresponding amino acid sequence (SEQ ID NO:3) (SEQ ID NO:4) of the csp2 gene of *Corynebacterium glutamicum* termed *Corynebacterium melassecola* ATCC17965. The numbering of the nucleotides is presented on the right-hand side of the figure. The probable Shine-Dalgarno sequence is underlined. A 22-bp palindrome which probably corresponds to the transcription terminator is indicated by opposite arrows.

Figure 13:
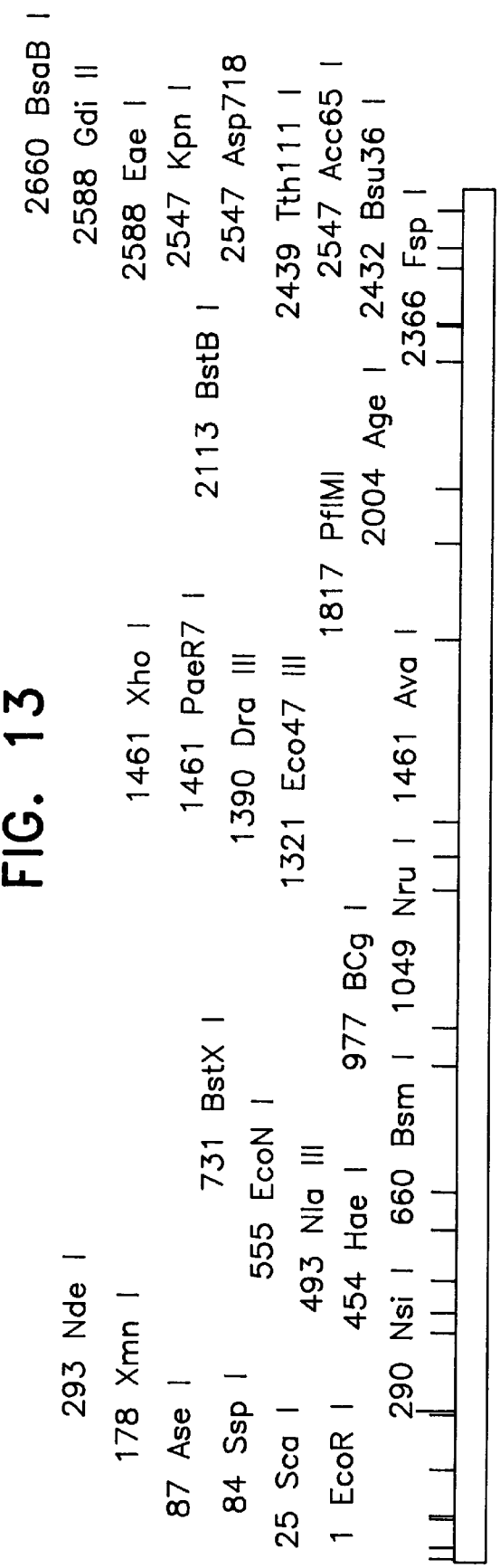

FIG. 13. Restriction map of the sequenced DNA region of *C. melassecola* ATCC17965 carrying csp2.

Figure 14:
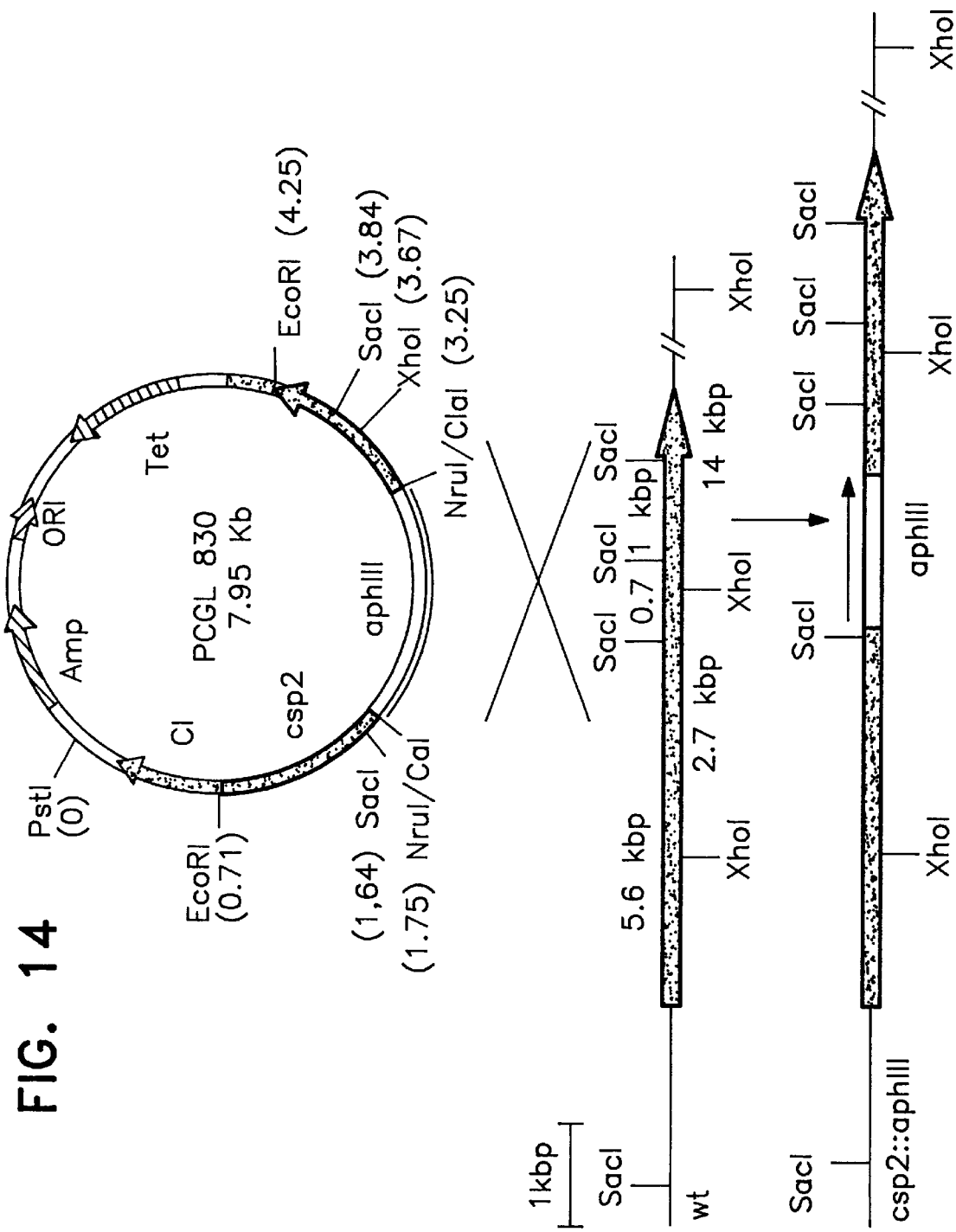

FIG. 14. Interruption of the csp2 gene in *C. glutamicum*. Chromosomal integration of the interrupted gene. The plasmid pCGL830 which is nonreplicative in *C. glutamicum*, carries the csp2 gene interrupted by the aphIII. The direction of transcription of the aphIII and csp2 genes is represented by an arrow on the plasmid pCGL830. Wt represents the strain *B. lactofermentum* 15 and csp2 :: aphIII, the integrant with the interrupted csp2 gene.

Figure 15:
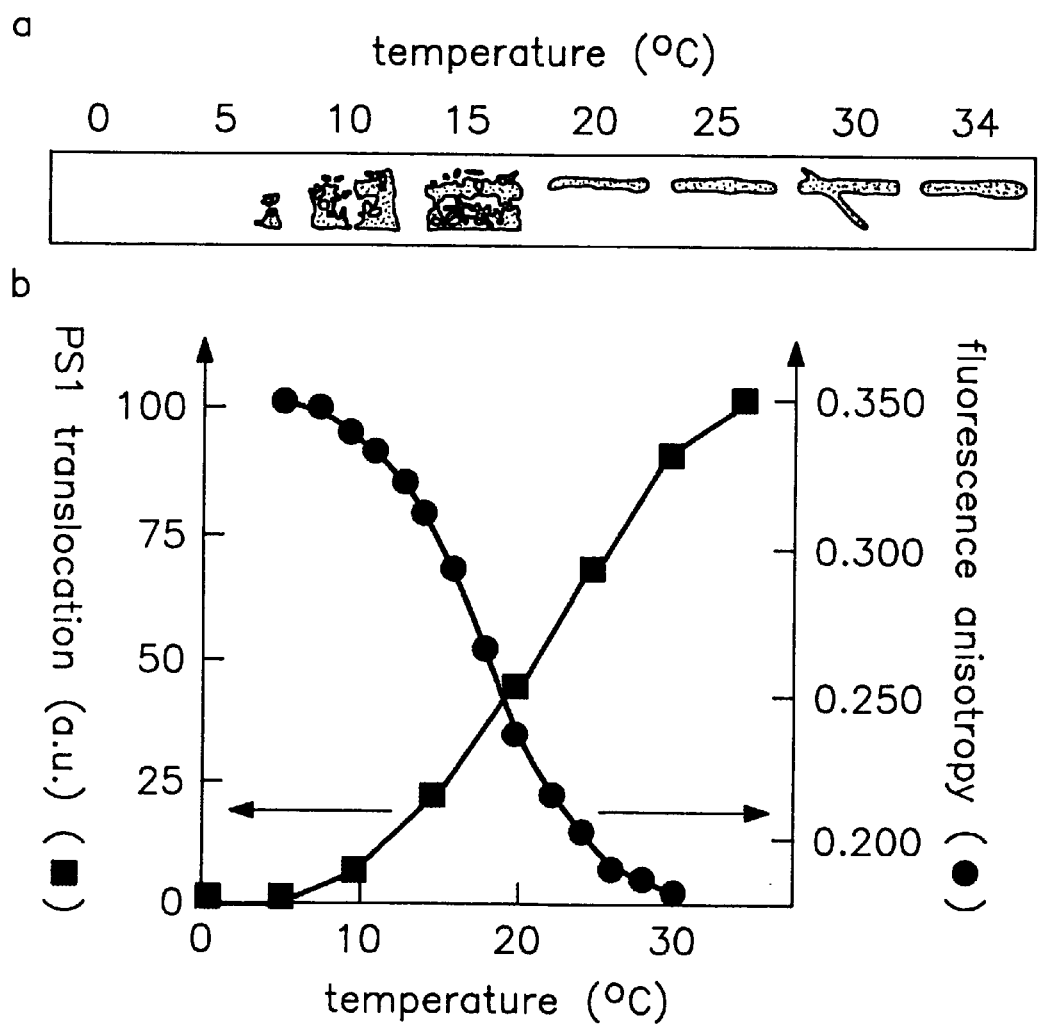

FIG. 15. Translocation of PS1 as a function of the temperature. 10 ml of culture in the exponential phase (OD650=1) at 34° C. was labeled with $^{35}S$ methionine (37 TBq/mmol, 16 nM final concentration) for 1 min. At the end of the pulse, chloramphenicol (100 μg/ml) and $^{32}S$ methionine (final concentration 0.5 mM) are then added. 1 ml of aliquote is removed and rapidly cooled to the temperature indicated. The incubation is continued at this temperature for 30 min and the secreted parietal fraction of PS1 is extracted. The extract is then subjected to an SDS-PAGE and autoradiographed (a). The intensity of the bands is determined by densitometry (b, left-hand axis) and is given in arbitrary units based on 100 at 34° C. The translocation is a function of the phase transition of the membrane lipids.

Figure 16:
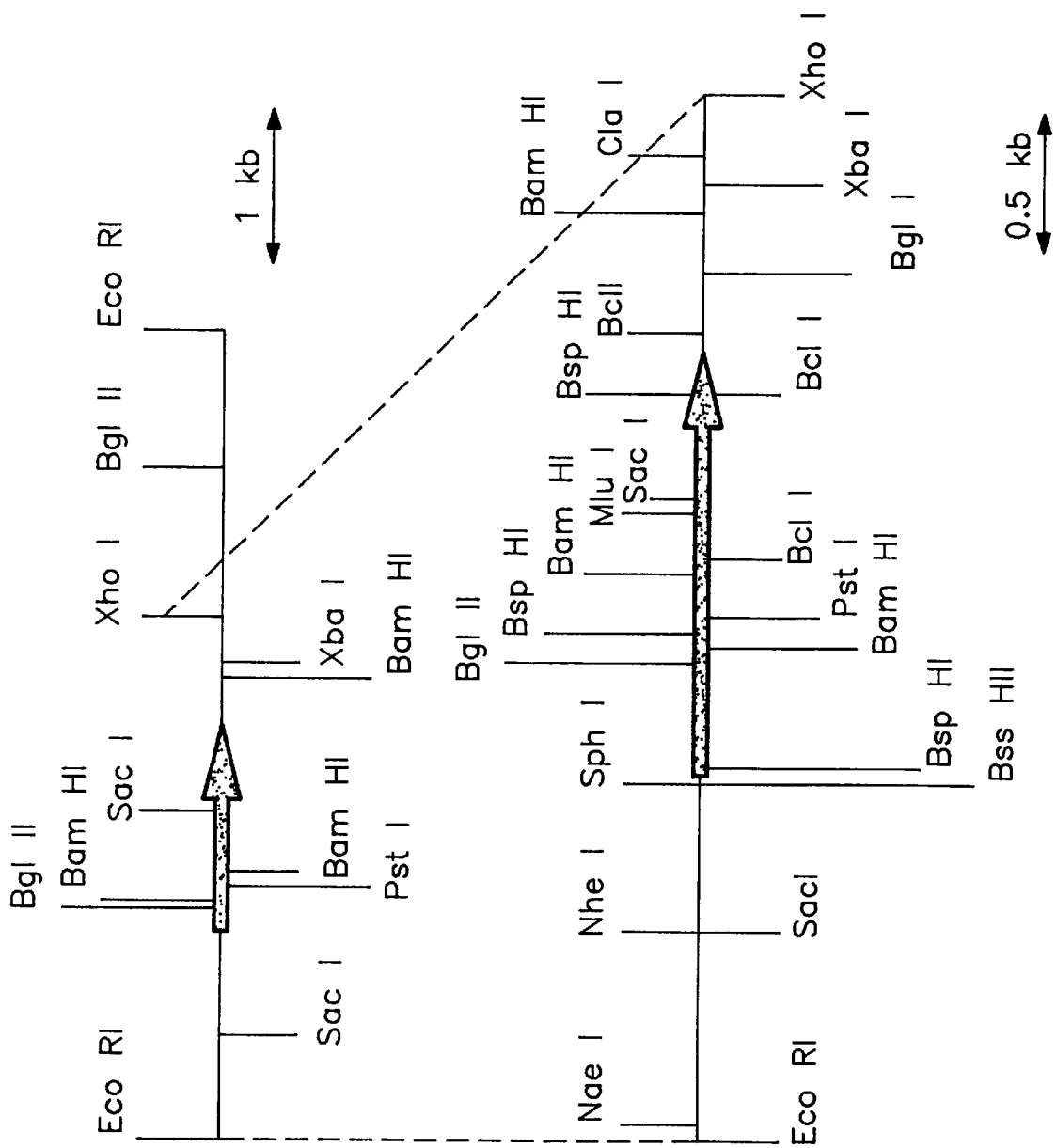

FIG. 16. Restriction map of the gdhA gene.

FIG. 17 (SEQ ID NO: 5). Complete sequence of the NheI-BlgI fragment (SEQ ID NO: 5) containing the gdhA gene of *C. melassecola*.

Figure 18:
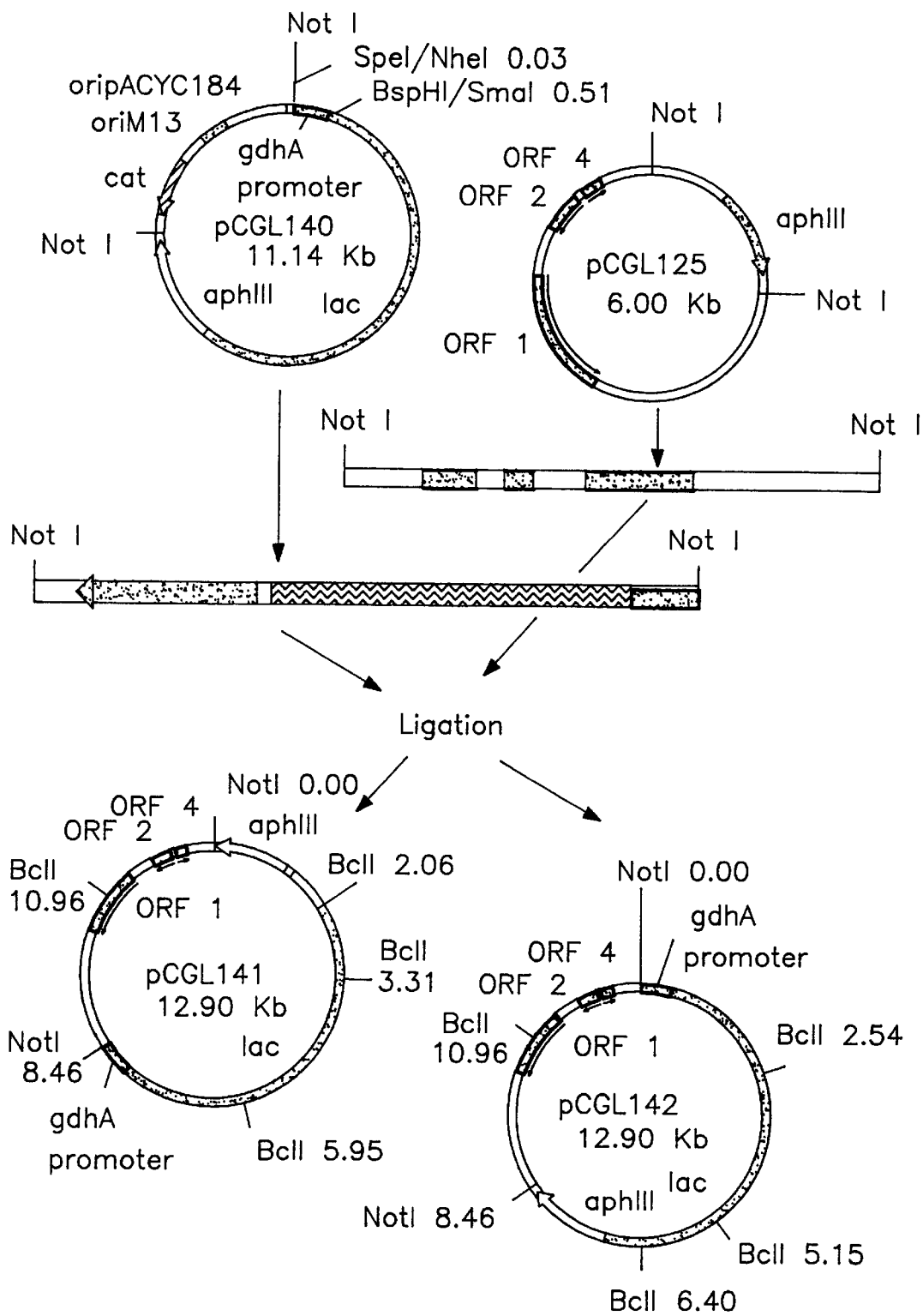

FIG. 18. Construction of pCGL141 and pCGL142, vectors for fusion between the promoter of the gdhA gene and the lacZ gene.

FIG. 19 (SEQ ID NOS: 19–22). Oligonucleotides used in the constructions.

Figure 20A:
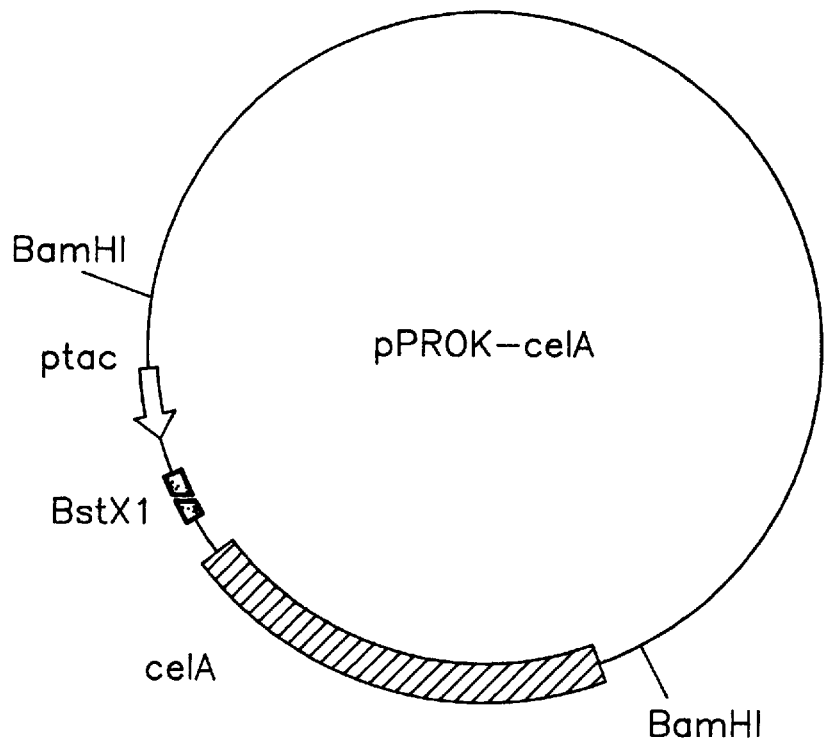
Figure 20B:
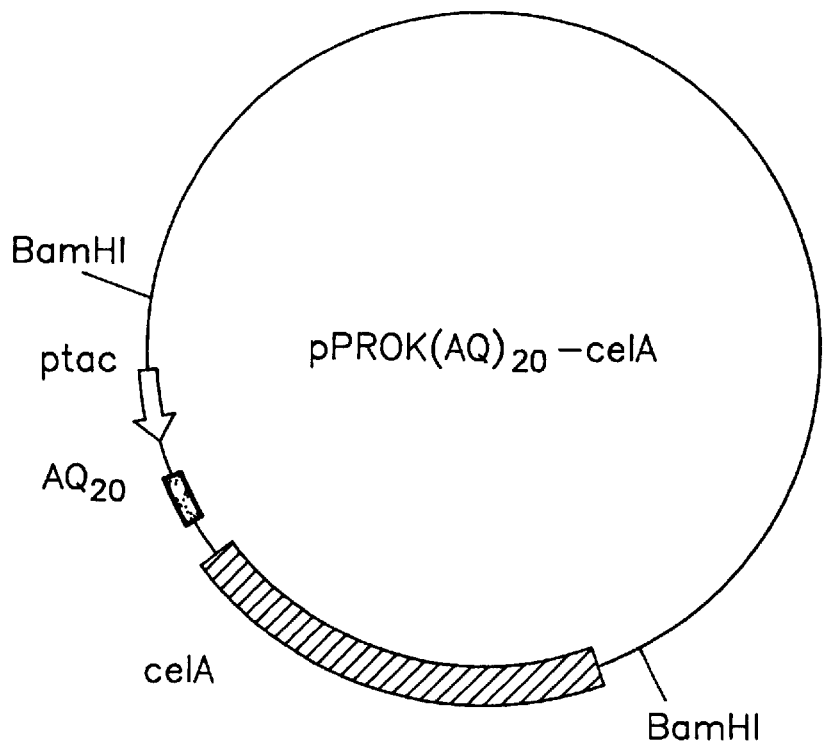

FIGS 20A and 20B. Construction of pPROK(AQ)$_{20}$celA

Figure 21:
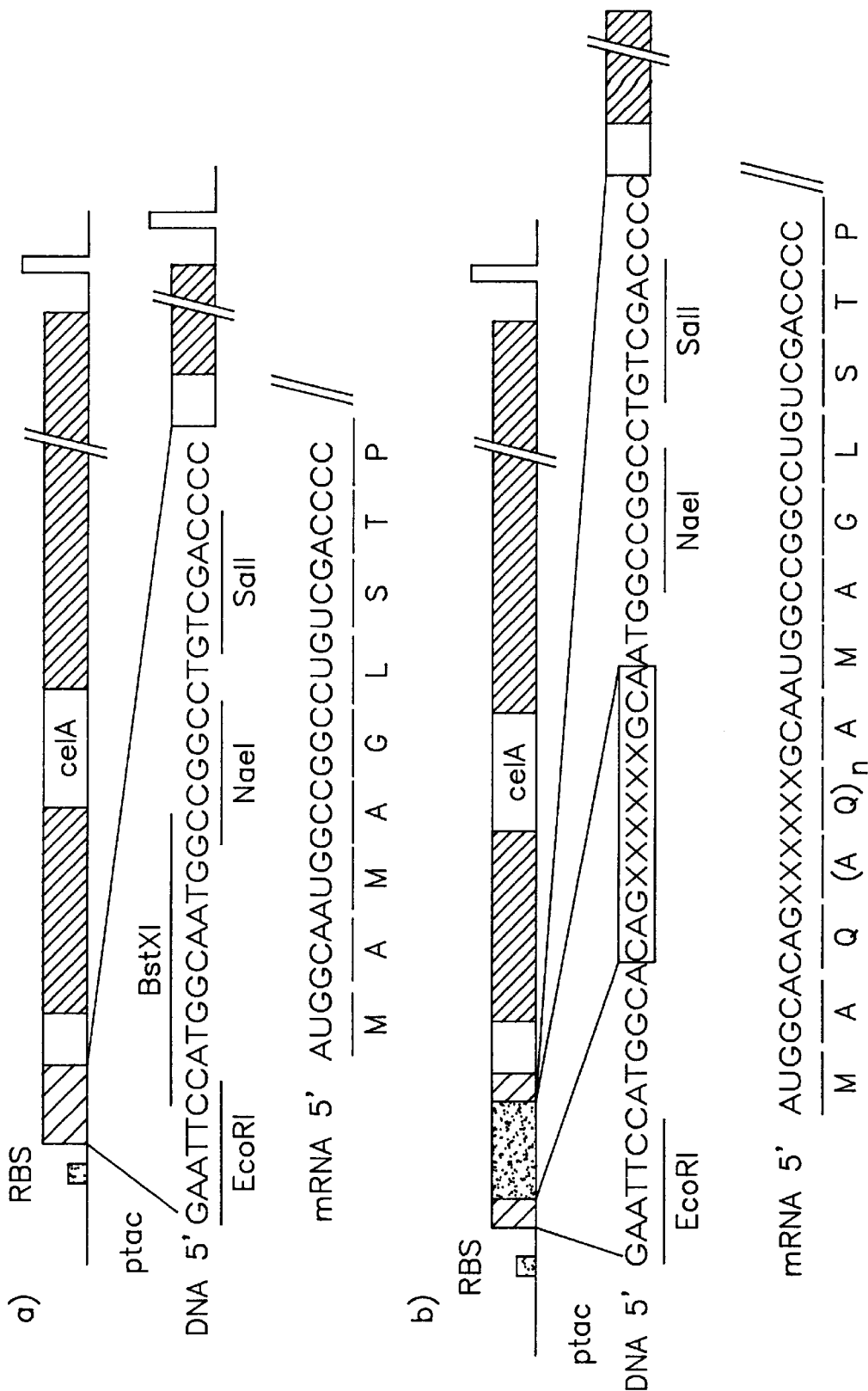

FIG. 21 (SEQ ID NOS: 23—26). Detail of construction placing the synthetic gene between ptac and the celA gene— a) construction placing ceLA under the control of ptac, b) fate of the construct after introduction of the polypeptide AQ.

ptac: tac promoter

RBS : ribosome-binding site

▨: synthetic sequence in 5 of the celA gene which permits the introduction of the sequence equivalent to the polypeptide AG and its fusion with other possible genes (DGF1, DGF2)

■: nucleotides introduced into the BstXI site equivalent to the polypeptide AQ (DGF5, DGF6)

☐ : sequence of DNA equivalent to a portion of the signal sequence of EGA

▨: sequence of DNA equivalent to the coding sequence

⊓: transcription terminator

P : first amino acid belonging to the signal sequence of EGA

Figure 22:
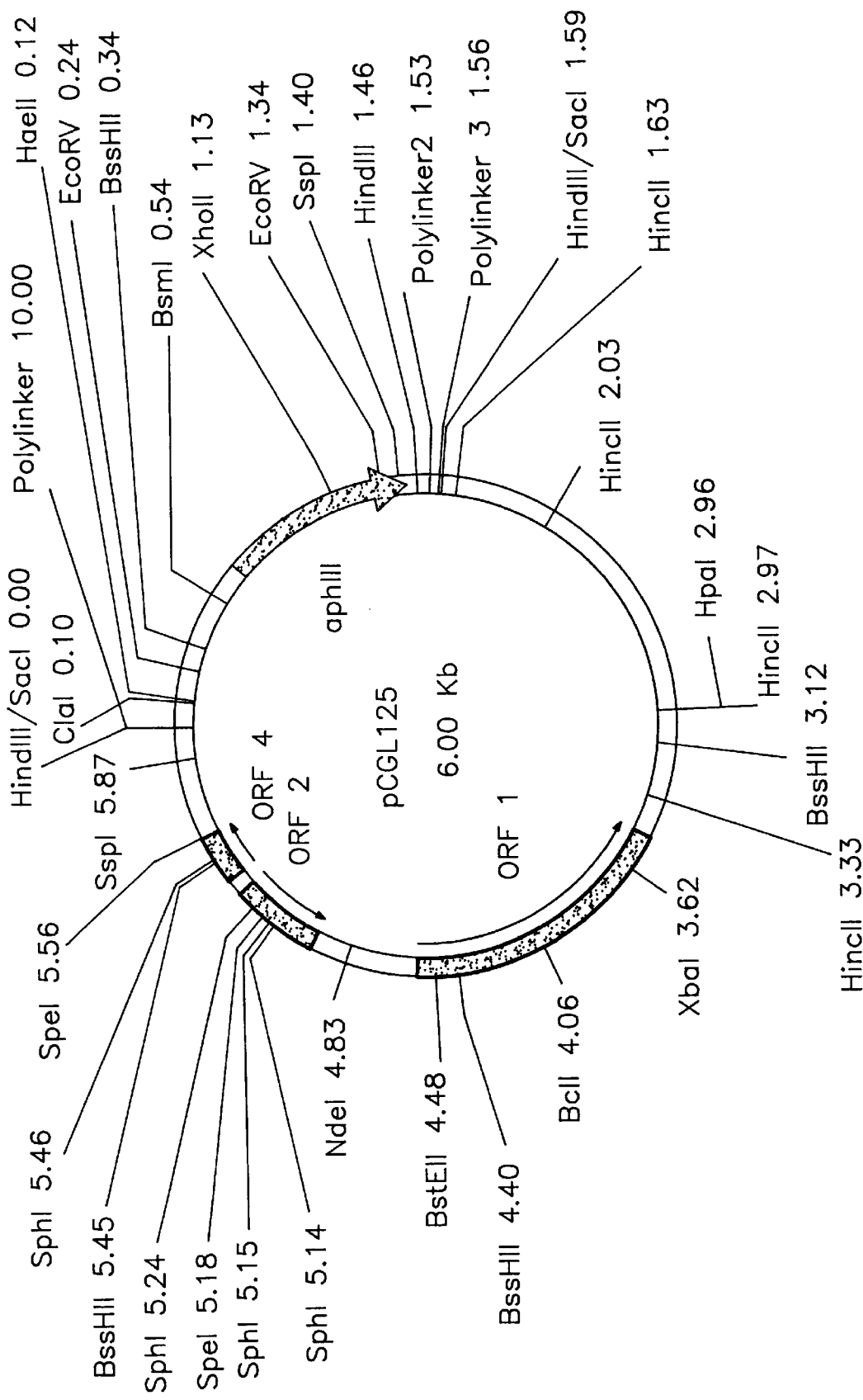

FIG. 22. Structure of pCGL125.

EXAMPLE 1

Identification of PS1 and PS2 in the culture supernatant and in the wall of *Corynebacterium glutamicum*.

Polyacrylamide gel analysis under denaturing conditions (SDS-PAGE) (Laemmli, U. K. (1970) Cleavage of structural proteins during the assembly of the head of bacteriophage T4. Nature 227:680–685) of a culture supernatant of the strain *Corynebacterium melassecola* ATCC17965, currently redefined as a strain of *Corynebacterium glutamicum* (Jones, D., and Collins, M.D. (1986) Irregular nonsporing Gram-positive rods. In Bergey's Manual of Systematic Bacteriology. Williams and Wilkins (eds). Baltimore, vol.2, pp. 1261–1434.) shows two major proteins named PS1 and PS2 of molecular mass approximately 67000 and 63000 respectively. The concentrations of PS1 and PS2 follow the growth curve of the bacterium and reach the maximum in their stationary phase. A substantial secreted fraction of these proteins and especially for PS2 is also situated in the wall of the bacterium. To extract PS1 and PS2 from the wall, an SDS treatment of the bacterium is used which does not cause significant lysis of the bacterium. Thus, in order to obtain a maximum concentration of PS1 and PS2, it is therefore possible to accumulate the two secreted fractions, the culture supernatant and the parietal fraction, and to obtain a final preparation where PS1 and PS2 are highly predominant. Polyclonal antibodies were prepared against PS1 and PS2, there is no immunological cross-reaction between the two proteins, which effectively shows that these proteins are different. Proteins having strong immunological cross-reactivity with PS1 and PS2 were found in the culture supernatant of bacterial strains related to *Corynebacterium melassecola* ATCC17965 such as the strain *Brevibacterium lactofermentum* 15 (Bonnassie, S., Oreglia, J., Trautwetter, A., and Sicard, A.M. (1990) Isolation and characterization of a restriction and modification deficient mutant of *Brevibacterium lactofermentum*. FEMS Microbial Letters 72: 143–146.) , *Brevibacterium lactofermentum* ATCC21086 and *Brevibacterium flavum* ATCC 14067. PS1 and PS2 were tested for several enzymatic activities including the invertase, pectinase, nuclease, collagenase, amylase, bacteriocine, endoglucanase and broad-spectrum protease activity. None of these enzymatic activities could be associated with PS1 or PS2.

EXAMPLE 2

Evidence for the functionality of the signal peptide of PS1 in *Escherichia coli* (FIG. 1).

When the csp1 gene carried by the plasmid pCGL612 (FIG. 1) is expressed in *E. coli* TG1, Western blot analysis of a crude extract of this recombinant with anti-PS1 antibodies reveals the presence of a major protein which has the same molecular mass as protein PS1 which is present in the culture supernatant of *C. melassecola*. A minor protein with a slightly higher molecular mass is also detected. In fact the major protein band corresponds to the mature form of PS1 (without signal sequence) and the minor protein band to the precursor form of PS1 (with the signal sequence).

Indeed, in a first experiment, the release of periplasmic proteins (secreted enzymes) of the recombinant strain *E. coli* TG1(pCGL612) by osmotic shock (Heppel, L.A. (1967) Selective release of enzymes from bacteria. Science 156: 1451–1455.) and the detection of the released protein contents by Western blotting with anti-PS1 antibodies reveals only the major protein. The isocitrate dehydrogenase activity (Shiio, I., and Ujigawa, K. (1978) Enzymes of the glutamate and aspartate synthetic pathways in a glutamate-producing bacterium, *Brevibacterium flavum*. J. Biochem 84: 647–657.) of the strain was measured as a way of monitoring lysis; this lysis was estimated in this experiment at less than 1%. This leads to the conclusion that the major protein band corresponds to the mature form of PS1 and that the protein is exported across the cytoplasmic membrane of *E. coli*.

In a second experiment, the crude extract of the recombinant strain *E. coli* TG1(pCGL612) was analyzed by Western blotting with anti-PS1 antibodies before and after addition of chloramphenicol in order to inhibit protein synthesis. The minor band progressively disappears after the inhibition of protein synthesis. This minor PS1 band does not disappear if there is added 5 minutes before the addition of chloramphenicol CCCP (carbonyl cyanide m-chlorophenylhydrazone), a protonophore which dissipates the proton motive force across the cytoplasmic membrane. The disappearance of the minor PS1 band is therefore not the result of a degradation by proteases. Its progressive disappearance after inhibition of protein synthesis and its absence from the periplasm are in agreement with the hypothesis of the maturation of this precursor form by a peptidase signal sequence situated in the membrane and its translocation across the cytoplasmic membrane. This result also shows that in *E. coli* the maturation of PS1 is dependent on the proton motive force in vivo.

EXAMPLE 3

Nucleotide sequence of the csp1 gene encoding PS1

The sequencing of a 2547-base pair fragment containing the PS1-encoding gene, named csp1, of the region upstream was carried out. The nucleotide sequence is presented in FIG. 2 (sequence ID No. 1). FIG. 3 represents the restriction map of this sequenced region.

Using computer analysis, a 1971-base pair open reading frame was identified corresponding to 657 amino acids.

The putative signals for starting the translation (GAGAAGGAAAACTTCATG) (SEQ ID NO: 8) and for starting the transcription (TACATA(-35) and TAAGAT(-10) have been identified. The AGAAGGA sequence extracted from the ribosome-binding site described above is complementary (underlining) to the 3' end of the rRNA of the Gram-positive type bacteria *Staphylococcus aureus* and *Steptomyces lividans* (5'-GAU CAC CUC CUU UCU OH-3') (SEQ ID NO: 9) (McLaughlin, J. R., Murray, C. L., and Rabinowitz, J. C. (1981) Unique features of the ribosome-binding site sequence of the Gram positive *Staphylococcus aureus* β-lactamase gene. J. Biol. Chem. 256: 11283–11291.) (Bibb, M. J., and Cohen, S. N. (1982) Gene expression in Streptomyces: Construction and application of promoter-probe plasmid vectors in *Streptomyces lividans*. Mol Gen Genet 187: 265–277). The DNA region in 5' preceding the translational start codon contains two nucleotide sequences AAAAGTTATCCACAG (SEQ ID NO: 9) and ATTGAAAAA each repeated twice, from 28 to 42 (SEQ ID NO: 10) and from 70 to 84 for the first, then from 100 to 108 and from 171 to 179 for the second. These two sequences might be involved in the regulation of the transcription of the csp1 gene.

In the case of the secretion signals, a sequence at the NH2 end of the protein exhibits the characteristics of a signal sequence of Gram-positive type bacteria (Watson, M. E. E. (1984) Compilation of published signal sequences. Nucleic Acids Res. 12: 5145–5164). This signal sequence contains an excess of positive charge in the NH2-terminal position (7 amino acids with positive charge in the first 18-amino acids), followed by a sequence with an excess of nonpolar amino acids (18 amino acids in the next 23 amino acids) then by two putative amino acid sequences of a signal sequence cleavage site (pro thr ala ile ala, in position 28 to 32) (pro met ala ser ala, in position 39 to 43). Among these putative amino acid sequences of a signal sequence cleavage site, the second=pro met ala ser ala in position 39 to 43 seems the most probable; indeed, protein PS1 was purified from the culture supernatant of *Corynebacterium glutamicum* until electrophoretic homogeneity is obtained using two different procedures (see Example 5) and the preparations were used to determine the amino-terminal sequence by Edman degradation. No signal was obtained although 5 nmol of purified protein were used. Since two purification procedures were used, it is probable that protein PS1 is blocked in vivo and that the blocking is not a consequence of the purification technique used. The second cleavage sequence proposed is thought to reveal a glutamine (position 44) as first amino acid of the mature sequence, which is easily converted to pyroglutamic acid, making the amino-terminal sequencing of the protein impossible by the Edman technique.

A putative terminator site of rho-dependent type is found in the 3' region of the gene at 55 nucleotides from the three stop codons och-amb-opa (Rosenberg, M., and Court, D. (1979) Regulatory sequences involved in the promotion and termination-of RNA transcription. Annu Rev Genet 13: 319–353.). The ΔG of this hairpin structure is equal to −35.7 kcal/mol (Freier, S. M., Kierzek, R., Jaeger, J. A., Sugimoto, N., Caruthers, M. H., Neilson, T., and Turner, D. H. (1986) Improved free-energy parameters for predictions of RNA duplex stability. Proc Natl. Acad Sci USA 83: 9373–9377.)

The calculated molecular mass corresponding to the 657 amino acids contained in the open reading frame is 70874. Yet, the molecular mass of the most probable signal sequence (cleavage site between amino acid 42 and 43) is 4411, which gives a calculated molecular mass for the mature protein of 66463 and which is very close to the 67000 value estimated on denaturing polyacrylamide gel.

The characteristics of the sequence are restated below:

from 239 to 244 TACATA (signal −35)

from 269 to 274 TAAGAT (signal −10)

from 405 to 414 GAGAAGGAAA (SEQ ID NO: 30) ribosome-binding site from 420 to 2390 coding sequence from 420 to 548 peptide signal of secreted protein from 2455 to 2506 hairpin structure, terminator signal of rho-dependent type.

EXAMPLE 4

Sequence homologies between PS1 of *Corynebacterium glutamicum* and the proteins of the antigen 85 complex of Mycobacterium. (FIG. 4).

The NH2 moiety of protein PS1 is very similar to the three secreted mycobacterial antigens 85-A, 85-B and 85-C (Closs, O., Harboe, M., Axelsen-Christensen, N. H., and Magnussen, M. (1980) The antigens of *Mycobacterium bovis*, strain BCG, studied by crossed immunoelectrophoresis: a reference system Scand J. Immunol 12: 249–263.) (Wiker, H. G., Harboe, M., Nagai, S., and Bennedsen, J. (1990) Quantitative and qualitative studies on the major extracellular antigen of *Mycobacterium tuberculosis* H37Rv and *Mycobacterium bovis* BCG. Am Rev Respir Dis 141: 830–838.). The three corresponding genes of different mycobacterial species have been cloned and sequenced: antigen 85-A of *Mycobacterium bovis* BCG1173P2 and of *Mycobacterium tuberculosis* (Borremans, M., De Wit, L., Volckaert, G., Ooms, J., De Bruyn, J., Huygen, K., Van Vooren, J.-P., Stelandre, M., Verhofstadt, R., and Content, J. (1989) Cloning, sequence determination, and expression of a 32-kilodalton-protein gene of *Mycobacterium tuberculosis*. Infect Immun 57: 3123–3130.) (De Wit, L., De la Cuvellerie, A., Ooms, J., and Content, J. (1990) Nucleotide sequence of the 32 kDa-protein gene (antigen 85A) of *Mycobacterium bovis* BCG. Nucleic Acids Res 18: 3995.), antigen 85-B of *Mycobacterium bovis* Tokyo, *Mycobacterium kansaii* and *Mycobacterium leprae* (Matsuo, K., Yamaguchi, R., Yamazaki, A., Tasaka, H., and Yamada, T. (1988) Cloning and expression of the *Mycobacterium bovis* BCG gene for extracellular a antigen. J. Bacteriol 170: 3847–3854.) (Matsuo, K., Yamaguchi, R., Yamazaki, A., Tasaka, H., Terasaka, K., and Yamada, T. (1990) Cloning and expression of the gene for the cross-reactive a antigen of *Mycobacterium kansaii*. Infect Immun 58: 550–556.) (De Mendonca Lima, L., Content, J., Van Heuverswyn, H., and Degrave, W. (1991) Nucleotide sequence of the gene coding for the 85-B antigen of *Mycobacterium leprae*. Nucleic Acids Res 19: 5789.), and antigen 85-C of *Mycobacterium tuberculosis* (Content, J., De La Cuvellerie, A., De Wit, L., Vincent-Levy-Frébault, V., Ooms, J., and De Bruyn, J. (1991) The genes coding for the antigen 85 complexes of *Mycobacterium tuberculosis* and *Mycobacterium bovis* BCG are members of a gene family: cloning, sequence determination, and genomic organization of the gene coding for antigen 85-C of M. tuberculosis. Infect Immun 59: 3205–3212.). Protein PS1 of Corynebacterium glutamicum has about 33% of identical residues (σ=1.1) and about 52% of similar residues (σ=1.1) with these six proteins over a length of about 330 amino acids (+/−5). This length of about 330 amino acids corresponds for the mycobacterial antigens to the total length of the protein. All these mycobacterial proteins, just like PS1, contain a signal sequence of a length comparable to the longest signal sequences found in Gram-positive type bacteria (about 42 amino acids, σ=2.4). Protein 85-B of *M. bovis* and protein 85-C of *M. tuberculosis*, just like PS1, have a longer hydrophilic NH2 region (5 or more, of positively charged residues) than most signal sequences. Another important characteristic of all these signal sequences is the presence in position 3 or 5 of an acid residue, aspartic acid, except for antigen 85-C of *M. tuberculosis* where it is glutamic acid. The presence of an acidic charged residue is common to the NH2 ends of the Eucaryotic signal sequences, but it is completely unusual for the NH2 ends of Procaryotic signal sequences (Perlman, D., and Halvorson, H.O. (1983) A putative signal peptidase recognition site and sequence in eucaryotic and procaryotic signal peptides. J Mol Biol 167: 391–409.) (Watson, M. E. E. (1984) Compilation of published signal sequences. Nucleic Acids Res. 12: 5145–5164.). The reason for this characteristic is unknown. No other significant similarity has been found between PS1 and other proteins present in the EMBL/MIPS data banks.

EXAMPLE 5

PS1 and PS2 purification procedures used for the determination of the N-terminal sequence.

Procedure 1:

Proteins PS1 and PS2 were purified from the culture supernatant of *C. glutamicum* ATCC17965 by preparative electrophoresis on polyacrylamide gel and electroelution.

Bacteria, cultured in 200 ml rich LB medium at 34° C., were harvested in the stationary growth phase by centrifugation at 8000 g for 15 minutes and at 4° C. The proteins of the culture supernatant were then precipitated with 60% ammonium sulfate and harvested by centrifugation at 13000 g for 15 minutes at 4° C. The pellet is solubilized in 4 ml of 10 mM Tris HCl buffer, pH 6.8, and the solution is then dialyzed for 24 hours at 4° C. in this same buffer.

The dialyzed protein extract obtained after ammonium sulfate precipitation is deposited on an electrophoresis gel of format 16×20×0.75 cm. The electrophoresis is performed according to the procedure described by Laemmli (1970) using a 4% stacking gel and a 7.5% separating gel. The migration is carried out over fifteen hours at 40 mA. The gels are then stained with copper chloride according to the procedure described by Lee et al. (1987). The protein bands corresponding to proteins PS1 and PS2 are cut out and then completely destained. The proteins are then electroeluted from the gel for 5 hours at 48 mA and at 4° C., then dialyzed several times in a 10 mM Tris HCl buffer, pH 6.8, before being divided into several aliquote fractions and frozen at −20° C. The purification yield is of the order of 25% with a purity greater than 90%.

Procedure 2:

Proteins PS1 and PS2 are purified from the culture supernatant of *C. glutamicum* ATCC17965 by ultrafiltration, electrophoresis and transfer on PVDF membrane.

The bacteria, cultured in rich LB medium at 34° C., are harvested in the stationary growth phase by centrifugation at 8000 g for 15 minutes and at 4° C. 4 ml of supernatant are diluted 50-fold in a 50 mM phosphate buffer, pH 7.0, before being centrifuged on an ultrafiltration membrane whose cut-off is 30 kD. This step makes it possible to obtain an 80-μl protein extract which is then deposited on an electrophoresis gel consisting of a 4% stacking gel and a 7.5% separating gel. The electrophoresis is performed according to the procedure described by Laemmli with the following modifications. All the solutions used for preparing the gels as well as the migration buffer are degassed and contain 0.1 M thioglycolate. Furthermore, the separating gel is prerun before being used. All these precautions are taken with the aim of avoiding as far as possible the formation of free radicals which could result in modifications of the N-terminal end of the proteins and consequently in a possible blocking of this end. On completion of the electrophoresis, the proteins are transferred onto a PVDF membrane. This step is carried out in a 50 mM Tris, 50 mM borate buffer, pH 8.0, for 60 minutes and at 50 V. The membrane is then stained with amido black which makes it possible to locate and cut out the bands corresponding to proteins PS1 and PS2. The protein bands are then destained and used as they are for the N-terminal sequencing. (Laemmli, U.K. 1970. Cleavage of structure proteins during assembly of the head of bacteriophage T4. Nature, 227: 680–685. - Lee, C., Levin, A., Branton, D. 1987. Copper staining: a five minute protein stain for sodium dodecyl sulfate polyacrylamide gels. Anal. Biochem., 166: 308–312.)

EXAMPLE 6

Production of a strain of *Corynebacterium glutamicum* no longer synthesizing PS1, called PS1-. (FIG. 5).

The *C. glutamicum* strain called *Brevibacterium lactofermentum* 15 is permissive to modified DNA of *E. coli* K12 (Bonnassie, S., Oreglia, J., Trautwetter, A., and Sicard, A.M. (1990) Isolation and characterization of a restriction and modification deficient mutant of *Brevibacterium lactofermentum*. FEMS Microbiol Letters 72: 143–146), whereas the *C. glutamicum* strain called *C. melassecola* ATCC17965 is a strain which is very restrictive with respect to the DNA of *E. coli* (Reyes, O., Guyonvarch, A., Bonamy, C., Salti, V., David, F., and Leblon, G. (1991) 'Integron'-bearing vectors: a method suitable for stable chromosomal integration in highly restrictive Corynebacteria. Gene 107: 61–68). For this reason, the *B. lactofermentum* 15 strain was chosen for carrying out the interruption of the csp1 gene. It was checked that the physical map of the csp1 gene is identical in *C. melassecola* ATCC17965 and in *B. lactofermentum* 15.

The 1.5 kb ClaI fragment of the plasmid pAT21 (Trieu-Cuot, P., and Courvalin, P. (1983) Nucleotide sequence of the Streptococcus faecalis plasmid gene encoding the 3'5"-aminoglycoside phosphotransferase type III. Gene 23: 331–341.) containing the aphA3 gene of *Streptococcus gaecalis*, which confers the resistance to kanamycin (Km$^r$), was inserted into the unique KpnI site (Asp718) of the csp1 gene present in the plasmid pCGL612, to give the plasmid pCGL613'. It was shown by Western blotting using anti-PS1 polyclonal antibodies that the recombinant *E. coli* strain harboring the plasmid pCGL613' is indeed of the PS1-phenotype. This plasmid is typical of replicating in *E. coli* but not in *C. glutamicum*. It was introduced into the strain of *C. glutamicum* called *B. lactofermentum* 15 by electrotransformation (Bonamy, C., Guyonvarch, A., Reyes, O., David, F., and Leblon, G. (1990) Interspecies electrotransformation in Corynebacteria. FEMS Microbiol Letters 66: 263–270.) and the Km$^r$ transformants were selected. In the Km$^r$ transformants, the plasmid pCGL613' is supposed to be integrated into the chromosome of *C. glutamicum* by homologous recombination with the csp1 region of the host genome. In 22.5% of the transformants, a double crossing-over event occurred resulting in the substitution of the wild-type csp1 gene by the csp1::aphA3 construct of the transformant plasmid, giving a Km$^r$–Tet$^s$ phenotype (FIG. 5). The total chromosomal DNA of the wild-type strain and of one of the Km$^r$–Tet$^s$ recombinants digested either by BglII or BamHI and EcoRI was analyzed by Southern blotting (Sambrook, J., Fritsch, E. F., and Maniatis, T. (1989) Molecular cloning: a Laboratory manual, second edition. Cold Spring Harbor, New York: Cold Spring Harbor Laboratory Publications.) with the pCGL613' probe. The csp1 gene is contained in an approximately 7.5 kb fragment in the wild-type strain whereas the integrant pCGL613' contains an approximately 9-kb fragment corresponding to the 1.5-kb aphA3 gene inserted into the csp1 gene. The BamHI-EcoRI digestion confirms the structure of the integrant presented in FIG. 5.

The Km$^r$-Tet$^s$ integrant was also analyzed by Western blotting for the production of PS1 using anti-PS1 polyclonal antibodies. There is no protein PS1 either in the culture supernatant or in the crude extract of this strain. This confirms that the csp1 gene cloned into λgt11 corresponds to a unique gene which indeed encodes PS1 in *C. glutamicum*.

This PS1- *C. glutamicum* strain is completely viable and its growth rate does not appear to be affected. This result shows that it is possible to use the csp1 gene region as target for the integration of homologous or heterologous DNA into a strain of *C. glutamicum* without affecting, a priori, the viability.

EXAMPLE 7

Expression in *C. glutamicum* of the csp1 gene in multicopies. Analysis of the important reqions of PS1 which are necessary for its synthesis and its secretion.

For this series of experiments, the plasmid pCGL616 was constructed. It contains the entire csp1 gene and was constructed from the plasmid pCGL125, corresponding to the plasmid pBL1 (Santamaria, R., Gil, J. A., Mesas, J. M. and J. F. Martin (1984) Characterization of an endogenous plasmid and development of cloning vectors and a transformation system in *Brevibacterium lactofermentum*. J. Gen. Microbiol. 130: 2237–2246.), replicative in *C. glutamicum*, equipped with a cloning cassette containing the aphA3 gene of *Streptococcus faecalis* and the plasmid pCSP1G, replicative in *E. coli*, containing the csp1 gene.

The plasmid pCGL616 resulting from this construction (FIG. 6) is replicative in *C. glutamicum*.

Restoration of the synthesis of PS1 in a strain of *C. glutamicum* PS1-.

The restoration in the so-called *B. lactofermentum* 15 PS1- strain of the synthesis of PS1 is observed after introduction into the latter of the plasmid pCGL616. In this *B. lactofermentum* 15 PS1- strain harboring the plasmid pCGL616, a larger quantity of secreted PSI is detected compared with the wild-type *B. lactofermentum* 15 strain (naturally PS1+). This indicates that it is possible to increase the concentration of PS1 secreted in a strain of *C. glutamicum* by increasing the number of copies of the csp1 gene.

This result is also demonstrated in the so-called *C. melassecola* ATCC17965 strain.

Constructions of plasmids derived from pCGL616 permitting the synthesis of truncated PS1 proteins (FIG. 7).

This experiment shows that a truncated PS1 protein of a molecular mass then equal to about 23000 (Mw), instead of 67000 (Mw) for the native protein, can still be secreted in *C. glutamicum*.

Seven deletions were performed in the csp1 gene region giving rise to seven different plasmids, starting with the plasmid pCGL616. All these deletions conserve the DNA region equivalent to the signal sequence of PS1 as well as the transcription terminator of the csp1 gene. In all cases, the synthesis and the secretion of the truncated PS1 protein was analyzed by Western blotting using anti-PS1 polyclonal antibodies. These results show that it is possible to delete most of the csp1 gene (FIG. 7) while still making the synthesis and secretion of a truncated protein PS1 possible. The largest deletion permitting this result corresponds to the deletion of the NcoI-BspEI (BspMII) fragment of about 1.3 kb of the csp1 gene (pCGL1041) giving a precursor protein size for PS1 equal to about 29 kD and to about 24 kD for the secreted mature form. A protein of about 23 kD is indeed detected by Western blotting, using anti-PS1 antibodies, in the culture supernatant of the so-called *B. lactofermentum* 15 PS1- strain harboring this plasmid pCGL1041.

EXAMPLE 8

Construction of an expression and secretion vector in *C. glutamicum* named PCGL1030 based on the csp1 system (FIGS. 8, 9, 10, 11)

Construction of the plasmid pCGL1030 (FIG. 8).

This plasmid which is replicative in *C. glutamicum* (contains the plasmid pBL1 of *C. glutamicum*) carries the promoter of the csp1 gene of C. glutamicum and the DNA region of this gene corresponding to the signal sequence plus the first 30 amino acids of the mature PS1 sequence. A multiple cloning site (polylinker 2 in FIG. 8) was placed immediately behind the 30th amino acid of the mature PS1 sequence in order to permit the easy cloning in phase of any heterologous gene which needs to be expressed in *C. glutamicum*. Finally, this plasmid is equipped with the elements of PS1 which are necessary for the secretion and therefore corresponds to both an expression and secretion tool.

Expression of the celA gene of *Clostridium thermocellum* in *Corynebacterium glutamicum* and secretion of the corresponding protein (FIG. 9).

The celA gene of *C. thermocellum* (Cornet, P., Millet, J., Beguin, P. and J.-P. Aubert (1983) Characterization of two cel (cellulose degradation) genes of *Clostridium thermocellum* coding for endoglucanases. Bio/Technology 1: 589–594.) encoding an endoglucanase named endoglucanase A or EGA, was cloned into the vector pCGL1030 at the Sma I site giving rise to the plasmid pCGL1031 (FIG. 9). This celA gene is derived from the plasmid pCGL1008 where a BstXI restriction site has been artificially introduced, very close to the translational start site of the protein EGA, for the purpose of chimeric constructions (see FIGS. 10, 11). The synthesis of the protein EGA is easily detectable by means of a staining test for enzymatic activity in a dish using an endoglucanase substrate, carboxymethyl-cellulose called CMC (Cornet, P., Millet, J., Béguin, P. and J.-P. Aubert (1983) Characterization of two cel (cellulose degradation) genes of *Clostridium thermocellum* coding for endoglucanases. Bio/Technology 1: 589–594.). This CMC test will be used for confirming the synthesis of the protein EGA of *C. thermocellum* in *C. glutamicum*. A CMC test for activity in a dish carried out on whole cells or on the culture supernatant in rich medium (LB -Luria Broth- or BHI -Brain Heart Infusion-) reveals, in both cases, the endoglucanase activity of a strain of *C. glutamicum* called *Brevibacterium lactofermentum* 15 harboring the plasmid pCGL1031. A higher activity will be noted on the LB + fructose or + glucose medium, indicating a stimulating effect of these two sugars on the expression of celA under the control of csp1 promoter. This is confirmed in the zymogram (Béguin, P.

(1983) Detection of cellulase activity in polyacrylamide gels using Congo red stained agar replicas Anal. Biochem. 131: 333–336.), and in the Western blotting performed on the culture supernatants with anti-EGA polyclonal antibodies.
Use of the csp1 system for the expression and the secretion of the synthetic polypeptide (AQK)10 (FIG. 10).

A synthetic gene corresponding to the polypeptide alanine-glutamine-lysine repeated 10 times was chemically synthesized and cloned into the BstXI site of the plasmid pCGL1008, giving rise to the plasmid pCGL1017. The EcoRI fragment of the plasmid pCGL1017 was cloned into the SmaI site of the plasmid pCGL1030 situated downstream of the csp1 promoter of the signal sequence and the first 30 amino acids of PS1 (and upstream of the reporter gene celA), giving rise to the plasmid pCGL1032 (FIG. 10). The detection of the chimeric protein PS1-(AQK)10-EGA is performed as described above, by the CMC test in a dish, by zymogram or by Western blotting.
Use of the csp1 system for the expression and secretion of the synthetic polypeptide (AQ)19 (FIG. 11).

A synthetic gene corresponding to the polypeptide analine-glutamine repeated 20 times was chemically synthesized and cloned into the BstXI site of the plasmid pCGL1008, giving rise to the plasmid pCGL1002. The EcoRI fragment of the plasmid pCGL1002 was cloned into the SmaI site of the plasmid pCGL1030, situated downstream of the csp1 promoter of the signal sequence and the first 30 amino acids of PS1 (and upstream of the reporter gene celA), giving rise to the plasmid pCGL1033 (FIG. 11). The detection of the chimeric protein PS1-(AQ)19-EGA is performed as described above, by the CMC test in a dish, by zymogram or by Western blotting. The sequence in *B. lactofermentum* in the plasmid pCGL1033 revealed the loss of a coding sequence AQ (passage from $AQ_{20}$ to $AQ_{19}$ during the cloning in *B. lactofermentum*).

This series of experiments shows that the promoter of the csp1 gene permits the expression in *C. glutamicum* of the heterologous celA gene of *Clostridium thermocellum* and the chimeric constructs (AQK)10-celA and (AQ)19-celA. Furthermore, these experiments show that the elements of PS1, in this case, its signal sequence followed by the first 30 amino acids of each mature sequence placed upstream of the heterologous genes permit the secretion of the corresponding products. The effect of the culture medium and the addition or otherwise of sugar to this medium, in this case, glucose or fructose, has an effect on the production of the corresponding product. In particular, under the control of the csp1 promoter and in *C. glutamicum*, the production of EGA or of the chimeric proteins (AQK)10-EGA or (AQ)19-EGA, is higher in LB medium than in BHI medium, it is highly stimulated by glucose or fructose in LB medium. The csp1 promoter of *C. glutamicum* appears to be stronger than the natural celA promoter of *C. thermocellum;* indeed, the so-called *B. lactofermentum* 15 strain harboring the plasmid pCGL602, which contains the natural celA promoter has a substantially smaller endoglucanase activity than this same strain harboring the plasmid pCGL1031, where celA is under the control of the csp1 promoter of *C. glutamicum*.

The Western blot experiment performed on the culture supernatants of different strains containing pCGL1032 or pCGL1033 shows that several protein bands react with anti-EGA polyclonal antibodies. These different bands are specific for the endoglucanase EGA (absent from the control) and probably correspond to products of degradation of the protein and the chimeric proteins. However, bands of higher molecular mass are indeed observed with (AQK)10-EGA (pCGL1032) and (AQ)19-EGA (pCGL1033) and in a coherent manner (Mw (AQ)19-EGA>Mw(AQK)10-EGA).

EXAMPLE 9

Nucleotide sequence of the csp2 gene encoding protein PS2 of *Corynebacterium glutamicum* (FIGS. 12. 13).

Sequencing of a 2702-base pair fragment containing the gene encoding PS2, named csp2, and of the region upstream was carried out. The nucleotide sequence is presented in FIG. 12 (sequence ID No. 3). FIG. 13 represents the restriction map of this sequenced region.

Using computer analysis, a 1532-base pair open reading frame was identified corresponding to 510 amino acids.

A Shine Dalgarno type sequence was identified, AAGGAG, just upstream of the translational start codon (−12 to −17).

At the NH2 end of the protein is a very common signal sequence of Gram-positive type bacteria with 30 amino acids. A putative amino acid sequence, ile pro ala phe ala, of a signal sequence cleavage site has been found. The determination of the amino-terminal sequence of the protein by the Edman degradation technique, purified from the culture supernatant of *Corynebacterium glutamicum*, gave no signal although 5 nmol of purified protein was used. Since two purification procedures were used, it is probable that protein PS2 is blocked in vivo, just like PS1, and that the blocking is not a consequence of the purification technique used. The proposed signal sequence of 30 amino acids reveals a glutamine (position 31) as the first amino acid of the mature sequence, easily converted to pyroglutamic acid making the amino-terminal sequencing of the protein by the Edman technique impossible. This protein PS2 possesses the characteristics of the wall proteins, such as its very acidic character (pI=4.1), its lack of cystein residue and its very low content of methionine residue (Sleytr, U. B. (1978) Regular arrays of macromolecules on bacterial cell walls: structure, chemistry, assembly, and function. Int. Rev. Cytol. 53: 1–64.) (Sleytr, U. B. and P. Messner (1983) Crystalline surface layers on bacteria. Ann. Rev. Microbiol. 37: 311–339.). Electron miscroscope analyses confirm that PS2 is indeed a wall protein capable of arranging itself in an organized hexagonal structure at the cell surface.

A putative terminator site of rho-independent type is found in the 3' region of the gene at 76 nucleotides from the stop codon.

The characteristics of the sequence are the following:

from 562 to 567: ribosome-binding site from 579 to 2108: coding sequence from 579 to 668: signal sequence of secreted protein from 2188 to 2233: hairpin structure, putative transcription terminator signal of rho-independent type (present at 76 nucleotides from the stop codon).

EXAMPLE 10

Production of a strain of *Corynebacterium glutamaicum* no longer synthesizing PS2, called PS2−. (FIG. 14).

The interruption of the csp2 gene was performed in *C. glutamicum* called *B. lactofermentum* 15 by means of the vector pCGL830 (FIG. 14), a nonreplicative vector in corynebacteria, and carrying a copy of the csp2 gene inactivated by insertion of the aphIII (cloning of the aphIII gene into the unique NruI site of csp2 carried by the plasmid pCGL811). No PS2 signal was revealed by immunological detection with anti-PS2 polyclonal antibodies, on cellular extracts derived from the E. coli TG1 strain carrying the plasmid pCGL830. The integrated clones were selected by electroporation of the B. lactofermentum 15 strain and selection on Km. Among these integrants, the Tet$^s$ clones were obtained indicating a double crossing-over event resulting in the substitution of the wild-type gene by the interrupted gene.

Southern blot analysis of the XhoI- and SacI-digested chromosomal DNA of the Km$^r$ Tet$^s$ using the probe pCGL811 shows a fragment at 4.2 kb and 2.2 kb respectively instead of 2.7 kb for XhoI and 0.7 kb sacI obtained for the wild-type strain, indicating an increase in size linked to the presence of the aphIII gene.

The lack of detection of PS2 by Western blotting, with anti-PS2 polyclonal antibodies, in the different fractions confirms the interruption of the CSp2 gene in B. lactofermentum. This PS2-strain is completely viable and is not in any way affected in its growth. Like the region of the chromosome of C. glutamicum carrying the csp1 gene, this DNA region carrying the csp2 gene can also be used as target for the integration of foreign DNA without affecting the growth of the bacterium.

Restoration of the PS2+ phenotype in the B. lactofermentum 15 PS2-strain.

The 2.3-kb ScaI-FspI fragment containing the entire csp2 gene as well as the DNA region upstream, was subcloned into the plasmid pCGLB24 and reintroduced into the B. lactofermentum 15 PS2-strain, permitting the restoration of the PS2+ phenotype. It should be noted that a larger quantity of PS2 is obtained when the gene is in multicopies. These results show that the quantity of secreted product derived from the csp2 gene of C. glutamicum can be modified according to the number of copies of the gene.

An electron microscope analysis of a sample of the strains PS2+ and PS2- (obtained by the technique described above) by cryofracture very clearly shows that protein PS2 is effectively a wall protein capable of arranging itself in an organized hexagonal structure at the cell surface.

EXAMPLE 11

Effect of the temprature on the secretion of PS1.
(FIG. 15).

Bacteria in the exponential growth phase (34° C.) were labeled with $^{35}$S methionine for 1 min. Chloramphenicol (100 µg/ml) and an excess amount of cold methionine ($^{32}$S) were then added (time 0). The temperature of the cellular suspension is then rapidly adjusted to the desired temperature and the incubation is continued at the said temperature for 30 min. The translocation of PS1 is determined by SDS-PAGE, autoradiography and quantified by densitometry (FIG. 15). The translocation of PS1 is clearly dependent on the temperature. No translocation occurs below 10° C., it increases rapidly above this temperature to reach a maximum around 30° C. The trans-location is correlated with a phase transition of the lipids (FIG. 15).

EXAMPLE 12

Construction of a chromosomal DNA library for
Corynebacterium melassecola ATCC17965 and
cloning of the gdhA gene The chromosomal DNA of the strain ATCC17965 of C. melassecola was prepared according to the method described by Ausubel, F. M., Brent, R., Kingston, R. E., Moore, D. D., Seidman, J. G., Smith, J. A., Struhl, K. (Eds) ((1987) Current protocols in Molecular Biology. John Wiley and Sons, New York). A controlled digestion by the restriction endonuclease MboI (Boehringer) was performed on 10 µg of this DNA according to the procedure described by Maniatis, T., Fritsch, E. F., Sambrook, J. ((1982) Molecular cloning: a laboratory manual. Cold Spring Harbor Laboratory Press, Cold Spring Harbor, N.Y.). The DNA fragments were separated according to their size on a sucrose gradient as described by Ausubel et al. (1987). The fragments of between 6 and 15 kb in size were selected for constructing the library.

The cloning plasmid pUN121 (Nilsson, B., Uhlen, M., Josephson, S., Gatenberg, S., Philipson, L. (1983) An improved positive selection plasmid vector constructed by oligonucleotide mediated mutagenesis. Nucleic Acids Res 11: 8019–8030) was prepared by the method of Birnboim, H.C., Doly, J. ((1979) A rapid alkaline extraction procedure for screening recombinant plasmid DNA. Nucleic Acids Res 7: 1513–1523), from the strain GM 2929 of E. coli which is freely available from Dr B. Bachmann. The plasmid was linearized by the restriction endonuclease BclI (Boehringer).

The library was constructed by ligation with T4 DNA ligase (Boehringer) under the conditions described by Ausubel et al. (1987), of 1 µg of plasmid pUN121 linearized by BclI and 2 µg of the 6- to 15-kb DNA fragments described above. The ligation mixture was introduced into the strain DH5 of E. coli by electroporation according to the procedure described by Dower, W. J., Miller, J. F., Ragsdale, C. W. ((1988) High efficiency transformation of E. coli by high voltage electroporation. Nucleic Acids Res 16: 6127–6145). E. coli clones carrying the recombinant plasmids were directly selected by their capacity to grow on LB medium containing 10 µg/ml of tetracycline. The plasmids of all the tetracycline-resistant clones were prepared by the method of Birnboim and Doly (1979). The combination of these plasmids corresponds to the DNA library.

The strain CLR207 recA of E. coli (Mattaj, I. W., McPherson, M. J., Wooton, J. C. (1982) Localization of a strongly conserved section of coding sequence in glutamate dehydrogenase genes. FEBS Letters 147: 21–25), deficient for glutamate dehydrogenase activity, was transformed with the C. melassecola ATCC 17965 DNA library. A transformant clone of E. coli CLR207 recA capable of growing on minimum selection medium containing 100 µg/ml of ampicillin was selected. This clone carries a recombinant plasmid pCGL310. The glutamate dehydrogenase activity measured according to the method of Meers, J. L., Tempest, D. W., Brown, C. M. ((1970) Glutamine (amide): 2-oxoglutarate amino transferase oxido-reductase (NADP), an enzyme involved in the synthesis of glutamate by some bacteria. J Gen Microbiol 64: 187–194), is restored in the strain CLR207 recA of E. coli carrying the plasmid pCGL310. Various subclonings made it possible in the first instance to shorten the DNA fragment of C. melassecola carrying the complete gdhA gene to a 3.8-kb DNA fragment delimited by the EcoRI and XhoI restriction sites. A precise restriction map of this EcoRI-XhoI fragment is represented in FIG. 16. Additional subclonings made it possible more precisely to delimit the gdhA gene to a 2.2-kb NheI-BglI fragment. A DNA—DNA hybridization by the method of Southern, E. M. ((1975) Detection of specific sequences among DNA fragments separated by gel electrophoresis. J Mol Biol 98: 503–517), showed that the cloned DNA fragment is indeed derived from the strain ATCC17965 of C. melassecola.

Determination of the nucleotide sequence of the gdhA gene.

In order to carry out the determination of the nucleotide sequence of the EcoRI-XhoI DNA fragment mentioned above, the following subclonings were performed: (1) EcoRI-BglII into the vector M13mp18 (Norrander, J., Kempe, T., Messing, J. (1983) Construction of improved M13 vectors using oligodeoxy-nucleotide directed mutagenesis. Nucleic Acids Res 26: 101–106) cut by EcoRI-BamHI, (2) XbaI-PstI into the vector M13mp18 cut by XbaI-PstI, (3) XhoI-BglII into the vector M13mp18 cut by SalI-BamHi, (4) EcoRI-PstI into the vector M13mp19 (Norrander et al., 1983) cut by EcoRI-PstI. Thus, the complete nucleotide sequence of the EcoRI-XbaI fragment contained in the EcoRI-XhoI fragment could be determined on the two strands by the method of Sanger, F., Nicklen, S., Coulson, A. R. ((1977) DNA sequencing with chain terminating inhibitors. Proc Natl Acad Sci USA 74: 5463–5467). The complete sequence of the NheI-BglI fragment containing the gdhA gene is presented in FIG. 17 (sequence ID No. 5).

Analysis of the nucleotide sequence of the gdhA gene

Analysis of the nucleotide sequence of the NheI-BglI fragment makes it possible to identify the following elements:

a) promoter (nucleotides 1 to 572)

The promoter of the gdhA gene can be characterized in that it comprises the following structural elements:

nucleotides 251 to 266 signal TGGTCATATCTGTGCG (SEQ ID NO: 10) exhibiting a similarity with the sequence TGG(Py)A(Pu)NNNNTTGCA (SEQ ID NO: 11) characteristic of the promoters recognized by the factor σ60 (Merrick, M. J. (1983) Nitrogen control of the nif regulon in Klebsiella pneumoniae: involvement of the ntrA gene and analogies between ntr C and nif A. EMBO J 2: 39–44) and regulated by ammonium.

nucleotides 437 to 442 signal TTCACA exhibiting a similarity with the sequence TTGAC(Pu) characteristic of the -35 region of the promoters of Strentomyces sp. (Strohl, W. R. ((1992) Compilation and analysis of DNA sequences associated with apparent streptomycete promoters. Nucleic Acids Res 20: 961–974)

nucleotides 466 to 471 signal TAGGAT exhibiting a similarity with the sequence TAG(Pu)(Pu)T characteristic of the -10 region of the promoters of Streptomyces sp. (Strohl, *1992*)

nucleotides 558 to 572 signal GGGAACGAGGAAATC (SEQ ID NO: 12) exhibiting a similarity with the ribosome-binding sequence AAAGGAGGTGATC (SEQ ID NO: 13) in Streptomyces sp. (Strohl, 1992)

b) coding sequence (nucleotides 573 to 1913)

The reading frame extending from position 573 to 1913 corresponds to that of glutamate dehydrogenase because of the following data:

The protein deduced from this reading frame contains 447 amino acids, with a predicted molecular weight of 48957 Daltons. This molecular weight is too close to that of the polypeptide (48300 D) observed after denaturing gel electrophoresis of a glutamate dehydrogenase preparation of the strain ATCC17965 of *C. melassecola*.

The primary structure of the glutamate dehydrogenase deduced from the nucleotide sequence of the gdhA gene of *C. melassecola* has strong similarities with the primary structures of glutamate dehydrogenases from other organisms (Teller, J. K., Smith, R. J., McPherson, M. J., Engel, P. C., Guest, J. R. ((1992) The glutamate dehydrogenase gene of *Clostridium symbosium*: cloning by polymerase chain reaction, sequence analysis and over-expression in *Escherichia coli*. Eur J Biochem 206: 151–159).

The amino acids mentioned by Baker, P. J., Britton, K. L., Engel, P. C., Farrants, G. W., Lilley, K. S., Rice, D. W., Stillman, T. J. ((1992) Subunit assembly and active site location in the structure of glutamate dehydrogenase. Proteins 12: 75–86) as being essential for the glutamate dehydrogenase activity are present in the glutamate dehydrogenase of *C. melassecola,* and this at positions equivalent to those described by Baker et al. (1992).

The secondary structure of the glutamate dehydrogenase of *C. melassecola* deduced from the primary sequence mentioned above, exhibits strong similarities with the secondary structures of glutamate dehydrogenases of other organisms (Teller et al., 1992).

c) terminator (nucleotides 1937 to 1977)

The terminator of the gdhA gene may be characterized in that it comprises the following structural element:

sequence CCCTGATCCGCGTTAAGGTCAGGG (SEQ ID NO: 14) capable of forming a hairpin structure rich in GC pairings with a $\Delta G = -13.6$ kcal/mol, followed by the sequence TTATTTGATTTCTT (SEQ ID NO: 15) rich in T. Such a structure is characteristic of rho-independent terminators (Rosenberg, M., Court, D. (1979) Regulatory sequences involved in the promotion and termi-nation of RNA transcription. Ann Rev Genet 13: 319–353).

Regulation of the expression of the gdhA gene of *C. melassecola*

The regulation of the expression of the gdhA gene of *C. melassecola* ATCC17965 was studied by measuring the variations of the glutamate dehydrogenase specific activity as a function of the nature of the medium in which this strain was cultivated. The glutamate dehydrogenase activity was measured by the method of Meers et al. (1970) from acellular extracts of *C. melassecola* obtained by ultrasonication.

The culture media used for this study are synthetic media whose base is that described by Liebl, W., Klamer, R., Schleifer, K. H. (1989) (Requirement of chelating compounds for the growth of Corynebacterium glutamicum in synthetic media. Appl Microbiol Biotechnol 32: 205–210). The following modifications were made:

The carbon source is either glucose at 11 g/l final (media 1, 2 and 4) or fructose at 10 g/l (medium 3).

The concentration of $NH_4^+$ ions is 125 mM in media 1, 3 and 4. It is 1.25 mM in medium 2 (limiting $NH_4^+$).

Medium 4 contains 50 g/l final of L-glutamate.

The specific activities measured for the glutamate dehydrogenase of the *C. melassecola* strain ATCC17965 cultivated in the different media described above are given in the table below. The activities are expressed in micromoles of NADPH2 transformed per minute per milligram of proteins.

| Medium | medium 1 | medium 2 | medium 3 | medium 4 |
| --- | --- | --- | --- | --- |
| GdhA specific activity | 4.4 +/- 0.3 | 23.2 +/- 1.1 | 18.2 +/- 1.8 | 2.8 +/- 0.2 |

This table makes it possible to identify the following three types of regulation of the expression of the gdhA gene of *C. melassecola* ATCC17965.

repression of the expression by glutamate (factor 1.57)

repression of the expression by excess ammonium (factor 5.27)

catabolic repression by glucose (factor 4.13 between fructose and glucose). It should be noted that in the case of catabolic repression, the isocitrate dehydrogenase, aconitase and citrate synthase enzymatic activities are also affected.

Construction of a gdhA-lacZ fusion vector

In order to control in *C. melassecola* the transcriptional character of the regulation of the gdhA gene by glutamate, excess ammonium and glucose, and to have a tool which allows a simple selection of mutants of *C. melassecola* not subjected to these regulations, a construct was produced between the promoter and the ATG codon for initiation of the translation of the gdhA gene and the lac operon of *E. coli* whose first five amino acids had been deleted from the region of the lacZ gene. This fusion was performed as follows:

Isolation of an EcoRI-BspHI fragment containing the promoter of the gdhA gene.

Conversion of the BspHI end into a blunt end.

Cloning of the fragment thus obtained into the vector pMC1403 (Casadaban, M. J., Chou, J., Cohen, S. N. (1980) In vitro gene fusions that join an enzymatically active β-galactosidase segment to amino-terminal fragments of exogenous proteins: *Escherichia coli* plasmid vectors for the detection and cloning of translational initiation signals. J Bacteriol 143: 971–980) linearized by EcoRI and SmaI, giving rise to the plasmid pCGL133.

Isolation of the NHeI-SalI fragment of pCGL133 containing the gdhA promoter—lac operon fusion described above and cloning into the vector pCGL241 (Reyes, O., Guyonvarch, A., Bonamy, C., Salti, V., David, F., Leblon, G. (1991) "Integron" bearing vectors: a method suitable for stable chromosomal integration in highly restrictive Corynebacteria. Gene 107: 61–68) linearized by SpeI and SalI, thus giving rise to the plasmid pCGL140 (FIG. 18).

Transfer of the integron isolated from pCGL140, containing the gdhA-lac fusion as well as the aphIII gene conferring the resistance to kanamycine, into the vector pCGL125, giving rise to pCGL141 and pCGL142 (FIG. 18). The plasmids pCGL141 and pCGL 142 were introduced into the *C. melassecola* strain ATCC17965 by transformation. The functionality of the gdhA-lac fusion was shown by detection of a β-galactosidase activity in the strains ATCC17965 of *C. melassecola* transformed by pCGL141 and pCGL142, activity absent in the same strain transformed by pCGL125. The β-galactosidase activity is detected by culturing the bacteria on complete solidified medium (BHI, Difco) containing the chromogenic substrate X-gal (5-bromo-4-chloro-3-indolyl β-D-galactopyranoside). The colonies derived from bacteria with β-galactosidase activity become blue on such a medium. By culturing bacteria transformed with pCGL141 and pCGL142 on the media 1, 2, 3 and 4 described above, solidified by adding agar to 15 g/l final and supplemented with kanamycine to 25 mg/l final and with X-Gal to 100 mg/l final, we were able to show that the regulation of the gdhA gene is indeed of a transcriptional type since the bacterial colonies obtained on these different media have a gradient of coloration compatible with the regulation shown by enzymatic measurement. Indeed, the colonies obtained on medium 4 are of a lighter blue than those obtained, in order of increasing intensity, on media 1, 3 and 2. We showed that this difference is reflected at the level of the enzymatic measurement of the β-galactosidase activity for cultures of *C. melassecola* transformed by pCGL141 in medium 1 and medium 4 (repression by glutamate).

| medium          | medium 1 | medium 4 |
|-----------------|----------|----------|
| β-gal. sp. act. | 0.118    | 0.052    |

The β-galactosidase activities were measured as described by Miller, J. H. (1972) (Experiments in molecular genetics. Cold Spring Harbor Laboratory Press, Cold Spring Harbor, N.Y.), from acellular extracts of *C. melassecola*.

Selection of mutants deficient in catabolic repression

An NTG mutagenesis of a strain derived from *C. melassecola* ATCC17965 was carried out. From this mutagenesis, a first selection was applied on the criterion of resistance to a glutamate analog, 4-fluoroglutamate. Mutants resistant to this analog may belong to different classes including the noncatabolic repression class. Indeed, in such mutants, it can be expected that the increase in the specific activity of glutamate dehydrogenase results. in an overproduction of intracellular glutamate, and thus in a dilution of the toxic analog, hence the phenomenon of resistance. The 4-fluoro-glutamate-resistant mutants were grouped together and the combination of cells was subjected to transformation with pCGL141. The fransformant bacteria were plated on solidified medium 1 containing X-Gal and kanamycin. The bacterial colonies having the most intense blue color were isolated and cultured in liquid medium 1 containing kanamycin. The glutamate dehydrogenase activity was measured from an acellular extract, the β-galactosidase activity from whole toluenized cells (Miller, 1972). The results obtained for one of the selected mutants are presented below.

| activity  | glutamate dehydrogenase | β-galactosidase |
|-----------|-------------------------|-----------------|
| control   | 6.3                     | 10.79           |
| mutant 90 | 12.1                    | 23.66           |

The results obtained therefore indeed show that it is possible to select by phenotype screening of the mutants for gdhA gene regulation with the tool constructed. It should be noted that it is very easy to eliminate pCGL141 and pCGL142 from the cells after selection, simply by culturing in the absence of kanamycin selection pressure.

EXAMPLE 13

Construction of a plasmid permitting the cloning of Peptides

For this construction, a celA subcloning step was carried out. The celA gene available in the form of a 3.5-kb HindIII fragment containing the promoter region, the gene and the beginning of another, nonidentified, gene, was subcloned in the form of a 2.6-kb HindIII-EcoRI fragment deleted from the unknown gene fragment, into a replicative vector of *E. coli*, pMTL23 (Chambers, S. P., Prior, S. E., Barstow, D. A. and Minton, N. P. (1988) The PMTL nic—cloning vectors. I. Improved pUC polylinker regions to facilitate the use of sonicated DNA for nucleotide sequencing. Gene. 68: 139–149.)

The EcoRI site was introduced by directed mutagenesis immediately behind the transcription terminator of the gene. This intermediate subcloning, given the restriction sites introduced, is necessary for the next cloning step; in particular, the cloning into the pMTL23 polylinker permits the introduction of an NcoI restriction site just behind the EcoRI site, which makes it possible to remove the fragment containing the coding region of celA in the form of an NaeI-NcoI fragment. This step also makes it possible to have a celA gene lacking nonidentified sequences in 3'.

The cloning of celA in the form of a HindIII-EcoRI fragment was carried out into the plasmid pMTL23 using the *E. coli* TG1 receiving strain. The *E. coli* strain possessing this plasmid indeed possesses the CMC+ phenotype associated with the expression of EGA; analysis of the restriction fragments obtained is in conformity with what is expected.

The construction of pPROK-celA (FIG. 20) is as follows:

The 4.6-kb plasmid pPROK-1 available from Clontech Laboratories, Inc. (Palo Alto, Calif., USA) is used.

This plasmid, replicative in *E. coli*, containing the tac promoter (Brossius et al. Gene 27: 161, 1984) is hydrolyzed with EcoRI-NcoI.

There is then introduced into this restriction, the adaptors DGF1/DGF2 of FIG. 19 in the form EcoRI-Blunt, these adaptors create the BstXI site. Then celA is introduced in the form NaeI(blunt)-NcoI from the preceding construct.

The plasmid thus obtained is called pPROK-celA. It contains the celA gene under the control of the tac promoter separated by a BstXI site introduced by means of the adaptors DGF1/DGF2.

EXAMPLE 14

Construction of a Plasmid Permitting the Expression of Multiple AO Sequences

To carry out the insertion of a sequence encoding 20 Ala-Gln (AQ) units, a second pair of synthetic oligonucleotides called DGF5/DGF6 is used (FIG. 19) which oligonucleotides correspond to the synthetic gene:

5' CAG[AQ]$_{20}$CAGGCA 3' (SEQ ID NO: 16)

3' CCGTGTC[AQ]$_{20}$GT 5' (SEQ ID NO: 17)

[AQ] representing the sequence encoding Ala-Gln.

The ends of the DGF5 and DGF6 sequences are compatible with the BstXI site and the sequence can therefore be cloned in this site.

The sequences of the DGF5 and DGF6 ends are such that, on the one hand, they orientate the direction of the cloning, and, on the other hand, they destroy the BstXI site following the cloning.

The use of nonphosphorylated adaptors avoids the introduction of several synthetic genes in tandem.

After digestion of pPROK-celA (FIG. 20) with BstXI and ligation of the synthetic gene, there is obtained: pPROK (AQ)$_{20}$celA having the structure represented in FIG. 20.

FIG. 21 details more particularly the structure of the AQ/EGA fusion site and shows the importance of the BstXI site used. The structure of this site is:

CCATGGCAATGG (SEQ ID NO: 18)

It can be observed that it contains an ATG start codon as well as the alanine-encoding codon GCA and a 2nd ATG codon for the insertion of a methionine after the coding sequence determined.

The insertion of the adaptor DGF5/DGF6 can occur in only one direction and introduces no base which is foreign to the object of interest.

This plasmid is treated with BamHI and treated by ligation with the restriction product of the plasmid pCGL125 treated with the same enzyme. The plasmid pCGL125 (FIG. 22) is a functional plasmid of *Brevibacterium lactofermentum* 15 containing a replication origin pBL1.

A strain according to the present invention is obtained by transformation of the said strain with the plasmid (pCGL125-(AQ)$_{20}$-celA) (pCGL1002 FIG. 11) and selection of the transformant strains.

In all the fusions which are carried out, the translation starts with a methionine immediately followed by (AQ)$_{20}$; the precaution is also taken to flank (AQ)$_{20}$ with a methionine at the COOH terminus; the detection of the polypeptide AQ, fused or otherwise with the protein celA, can be carried out by means of specific antibodies or by analytical detection after partial purification of the fusion protein and cyanogen bromide hydrolysis or conversely. The specific properties of the repetitive peptides permit an easy separation.

The strains mentioned are of the following origins:

| *Escherichia coli* | |
|---|---|
| CLR207 recA | B. Bachman |
| DH5alpha | Gibco BRL |
| GM2929 | B. Bachman |
| TG1 | Institut Pasteur |
| *Brevibacterium flavum* | |
| ATCC 14067 | ATCC |
| *Corynebacterium glutamicum (Brevibacterium lactofermentum)* | |
| 15 | S. Bonassie |
| ATCC 21086 | ATCC |
| *Corynebacterium glutamicum (Corynebacterium melassecola)* | |
| ATCC 17965 | ATCC |

The DH5alpha strain is available in the Clontech laboratories catalog No. C1021-1 (Palo Alto, Calif., USA).

The ATCC strains are available at American Type Culture Collection c/o Sales and Marketing Department, 12301 Parklawn Drive, Rockville, Md. 20852 USA.

A strain was deposited in the Collection Nationale de Cultures de Microorganismes (CNCM) of Institut Pasteur (Paris) on Jul. 23, 1991:

*Brevibacterium lactofermentum* 15 (CGL2005(B115) under the No. I-1126.

SEQ ID NO: 1
SEQUENCE TYPE: Nucleotide with corresponding protein
SEQUENCE LENGTH: 2547 base pairs
STRANDEDNESS: double strand with a single strand representation in the 5'–3' direction
TOPOLOGY: linear
MOLECULE TYPE: genomic DNA
ORIGINAL SOURCE
ORGANISM: *Corynebacterium melassecola*
STRAIN: ATCC17965
IMMEDIATE EXPERIMENTAL SOURCE: clone pCSP1G
FEATURES OF THE SEQUENCE
from 239 to 244 TACATA (signal −35) (S)
from 269 to 274 TAAGAT (signal −10) (S)
from 405 to 415 GAGAAGGAAAA ribosome-binding site (S)
from 420 to 2390 coding sequence (S)
from 420 to 548 secreted protein peptide (S)
from 2455 to 2506 hairpin structure rho-dependent terminator signal (S)
ASSOCIATED BIOLOGICAL ACTIVITY: precursor of the extracellular protein PS1 of *Corynebacterium melassecola* and of *Brevibacterium lactofermentum*
Homolog of the precursor of the proteins of the extracellular antigen 85 complex of Mycobacterium

```
AAGCTTCAAGGGGAAAACAAGGGCCTTAAAAGTTATCCACAGATCCGAAGTG          52

ATCCGCGCACTGGGGTGAAAAGTTATCCACAGGAAGCGGAGGGGCGGATTGA         104

AAAATTCAGCGAAATGCGAAAAGGTGGAGGGGAAATGCTGCGAGTCTTGCGG         156

ATTCCCGGCGTGGCATTGAAAAAAGTCTAAAGTTGAACTTAAGATTGAGGTC         208

ATTCTGAGGTTGTGACCTGCATCAGAAGAGTTACATACCCACATATGTAACC         260

TTCTGGACTAAGATCACGACAGACTGAAAAGAACTGAAGACTCTCAAGGCAT         312

AGCCCACGTGTGTTTGTCGGGCCGGAAGCGGGGAACTTTCGGGACGGATCTA         364

ACTCATTGCGGGCCTGTGCGCAGTATCCAAAAATCAAAATGAGAAGGAAAAC         416
```

| | | | | | | | | | | |
|---|---|---|---|---|---|---|---|---|---|---|
| TTC | ATG CGC GAC ACC GCA TTT CGT TCC ATC AAG GCT AAA | | | | | | | | | 455 |
| | Met Arg Asp Thr Ala Phe Arg Ser Ile Lys Ala Lys | | | | | | | | | |

```
GCT CAG GCT AAG CGC CGT TCC CTC TGG ATT GCA GCA GGC          494
Ala Gln Ala Lys Arg Arg Ser Leu Trp Ile Ala Ala Gly

GCT GTC CCA ACC GCA ATT GCG TTG ACT ATG TCC CTG GCA          533
Ala Val Pro Thr Ala Ile Ala Leu Thr Met Ser Leu Ala

CCT ATG GCT TCG GCT CAG TCC AGC AAC CTT TCC TCT GAT          572
Pro Met Ala Ser Ala Gln Ser Ser Asn Leu Ser Ser Asp

GCC GTA GTT GGC AGC ATC GCG CAG GGC GTC ACC GAT GGC          611
Ala Val Val Gly Ser Ile Ala Gln Gly Val Thr Asp Gly

CTG ACT GAC TAC CTG AAG CCT CGC GTC GAA GAG CTT CTT          650
Leu Thr Asp Tyr Leu Lys Pro Arg Val Glu Glu Leu Leu

GCT GGT GAA GTC ACC TAC CCA GAG ATC GCC GGG CTG CCT          689
Ala Gly Glu Val Thr Tyr Pro Glu Ile Ala Gly Leu Pro

GAT GGT GTG CGC GTG ATC AGC GCT GAG TGG GCA ACC TCC          728
Asp Gly Val Arg Val Ile Ser Ala Glu Trp Ala Thr Ser

AAG CAT GTC ATT TTG ACT ATT CAG TCT GCA GCA ATG CCA          767
Lys His Val Ile Leu Thr Ile Gln Ser Ala Ala Met Pro

GAG CGC CCA ATC AAG GTG CAG CTG CTG CTT CCG CGT GAC          806
Glu Arg Pro Ile Lys Val Gln Leu Leu Leu Pro Arg Asp

TGG TAC TCT TCC CCG AAC CGT GAG TTC CCT GAA ATC TGG          845
Trp Tyr Ser Ser Pro Asn Arg Glu Phe Pro Glu Ile Trp

GCA CTT GAC GGT CTG CGC GCG ATT GAA GAG CAG AGT GGT          884
Ala Leu Asp Gly Leu Arg Ala Ile Glu Glu Gln Ser Gly

TGG ACC ATT GAG ACC AAC ATT GAG CAG TAC TAC GCC GAT          923
Trp Thr Ile Glu Thr Asn Ile Glu Gln Tyr Tyr Ala Asp

AAG AAC GCC ATT GTT GTG CTC CCA ATC GGT GGC GAG AGC          962
Lys Asn Ala Ile Val Val Leu Pro Ile Gly Gly Glu Ser

TCC TTC TAC TCT GAC TGG GAA GAG CCA AAC AAC GGC AAG         1001
Ser Phe Tyr Ser Asp Trp Glu Glu Pro Asn Asn Gly Lys

AAC TAC CAG TGG GAG ACC TTC CTG ACT CAG GAG CTC GCA         1040
Asn Tyr Gln Trp Glu Thr Phe Leu Thr Gln Glu Leu Ala

CCG ATC CTG GAC AAG GGC TTC GTT TCC AAC ACC GAT CGC         1079
Pro Ile Leu Asp Lys Gly Phe Arg Ser Asn Thr Asp Arg

GCC ATC ACC GGT ATC TCC ATG GGC GGT ACC GCT GCG GTT         1118
Ala Ile Thr Gly Ile Ser Met Gly Gly Thr Ala Ala Val

AAC ATC GCA ACC CAC CAC CCA GAC ATG TTT AAG TTC GTC         1157
Asn Ile Ala Thr His His Pro Asp Met Phe Lys Phe Val

GGT TCC TTC TCC GGC TAT CTG GAC ACC ACC TCC GCT GGC         1196
Gly Ser Phe Ser Gly Tyr Leu Asp Thr Thr Ser Ala Gly
```

```
ATG CCA ATC GCT ATT TCC GCA GCC CTG GCA GAC GCC GGC      1235
Met Pro Ile Ala Ile Ser Ala Ala Leu Ala Asp Ala Gly

GGA TAC GAT GCC AAC GCA ATG TGG GGA CCA GTC GGT TCT      1274
Gly Tyr Asp Ala Asn Ala Met Trp Gly Pro Val Gly Ser

GAG CGC TGG CAG GAA AAC GAT CCA AAG AGC AAC GTA GAC      1313
Glu Arg Trp Gln Glu Asn Asp Pro Lys Ser Asn Val Asp

AAG CTC AAG GGC AAG ACC ATC TAC GTT TCC TCT GGT AAC      1352
Lys Leu Lys Gly Lys Thr Ile Tyr Val Ser Ser Gly Asn

GGT GCA GAT GAC TTC GGT AAG GAA GAC TCT GTA GCT ATT      1391
Gly Ala Asp Asp Phe Gly Lys Glu Asp Ser Val Ala Ile

GGA CCT GCA AAC GCG ACA GGT GTC GGT CTG GAA GTT ATC      1430
Gly Pro Ala Asn Ala Thr Gly Val Gly Leu Glu Val Ile

TCC CGT ATG ACT TCC CAG ACC TTC GTC GAT CGT GCA AAC      1469
Ser Arg Met Thr Ser Gln Thr Phe Val Asp Arg Ala Asn

CAG GCT GGC GTG GAA GTT GTT GCT AGC TTC CGT CCA TCC      1508
Gln Ala Gly Val Glu Val Val Ala Ser Phe Arg Pro Ser

GGC GTC CAC TCA TGG GAA TAC TGG CAG TTC GAG ATG ACT      1547
Gly Val His Ser Trp Glu Tyr Trp Gln Phe Glu Met Thr

CAG GCG TTC CCT CAC ATC GCT AAC GCT CTT GGC ATG TCC      1586
Gln Ala Phe Pro His Ile Ala Asn Ala Leu Gly Met Ser

ACT GAG GAC CGT GGC GTT GAG TGT GCA CCT GTC GGC GCA      1625
Thr Glu Asp Arg Gly Val Glu Cys Ala Pro Val Gly Ala

ATG GCT GAC GCT GTT GCC GAC GGC GCG ATG GGC ACC TGC      1664
Ile Ala Asp Ala Val Ala Asp Gly Ala Met Gly Thr Cys

CTG ACC AAC GAA TAC GAT GTT ACC GGC GGT AAG GCC CAG      1703
Leu Thr Asn Glu Tyr Asp Val Thr Gly Gly Lys Ala Gln

GAC TTC GCT AAC GGT CGC GCA TAC TGG TCT GCA AAC ACT      1742
Asp Phe Ala Asn Gly Arg Ala Tyr Trp Ser Ala Asn Thr

GGC GCT TTC GGC CTG GTT GGA CGC ATC AAC GCT CGT TAC      1781
Gly Ala Phe Gly Leu Val Gly Arg Ile Asn Ala Arg Tyr

TCT GAG CTG GGT GGA CCT GAC TCC TGG TTG GGC TAC CCA      1820
Ser Glu Leu Gly Gly Pro Asp Ser Trp Leu Gly Tyr Pro

ACC TCT TCT GAG TTG AAG ACA CCA GAC GGA CGT GGC CGC      1859
Thr Ser Ser Glu Leu Lys Thr Pro Asp Gly Arg Gly Arg

TTC GTC ACC TTC GAG CAC GGC TCC ATC TAC TGG ACC GCC      1898
Phe Val Thr Phe Glu His Gly Ser Ile Tyr Trp Thr Ala

ACC ACT GGT CCT TGG GAA ATC CCA GGC GAT ATG CTC GCC      1937
Thr Thr Gly Pro Trp Glu Ile Pro Gly Asp Met Leu Ala

GCA TGG GGC ACC CAG GAC TAT GAG AAG GGC AGC CTC GGC      1976
Ala Trp Gly Thr Gln Asp Tyr Glu Lys Gly Ser Leu Gly

TAC CCA ACC GGC GCC GCA GTT GAA TAC AAC GGT GGC CTG      2015
Tyr Pro Thr Gly Ala Ala Val Glu Tyr Asn Gly Gly Leu

CGC CAG CAG TTC GAA GGT GGC TAC GTA TTC CGT ACC TCC      2054
Arg Gln Gln Phe Glu Gly Gly Tyr Val Phe Arg Thr Ser

AAT AAC CAG TCT TAC TGG GTT CGC GGA GAA ATC TCC AAG      2093
Asn Asn Gln Ser Tyr Trp Val Arg Gly Glu Ile Ser Lys

AAG TAC GCC GAT GAC GGA ATC TTC GCT CAG CTT GGT TTC      2132
Lys Tyr Ala Asp Asp Gly Ile Phe Ala Gln Leu Gly Phe

CCA ACC GGC AAT GAG AAG TTG ATC AAC GGT GGC GCT TTC      2171
Lys Tyr Gly Asn Gln Lys Leu Ile Asn Gly Gly Ala Phe

CAG GAA TTC GAA AAG GGC AAC ATC TAC TGG TCC GTG TCC      2210
Gln Glu Phe Glu Lys Gly Asn Ile Tyr Trp Ser Val Ser

ACT GGC GCG CAC GTG ATT CTG CAC GGC GAC ATC TTC GAC      2249
Thr Gly Ala His Val Ile Leu His Gly Asp Ile Phe Asp
```

-continued

```
GCA TGG GGT GCT AAG GGC TGG GAG CAG GGC GAA TAC GGC         2288
Ala Trp Gly Ala Lys Gly Trp Glu Gln Gly Glu Tyr Gly

TTC CCA ACC TCT GAC CAG ACC GCA ATC ACC GCG GGT GGA         2327
Phe Pro Thr Ser Asp Gln Thr Ala Ile Thr Ala Gly Gly

CAG ACC ATT GAT TTC CAG AAC GGC ACC ATC CGT CAG GTC         2366
Gln Thr Ile Asp Phe Gln Asn Gly Thr Ile Arg Gln Val

AAT GGC CGA ATT GAG GAG TCT CGC TAATAGTGA AGCGCATCTA        2409
Asn Gly Arg Ile Glu Glu Ser Arg

CGCAACTCTCGCTTCCGGACTTTTGTGCCTGAGCCTTGCTGCTTGTGGGGGA        2461

GTCACTGTTGAAGGAGATGATTCTCCCTCGACAGCGGCAGCCCCAACAGAAA        2513

GCAGCGCTGGGTCAAGCAGCACCGCAAGGTCGAC                          2547
```

SEQ ID NO: 3
SEQUENCE TYPE: Nucleotide with corresponding protein
SEQUENCE LENGTH: 2702 base pairs
STRANDEDNESS: double strand with single strand representation in the 5'–3' direction
TOPOLOGY: linear
MOLECULE TYPE: genomic DNA
ORIGINAL SOURCE
ORGANISM: Corynebacterium melassecola
STRAIN: ATCC17965
IMMEDIATE EXPERIMENTAL SOURCE: clone pCGL815, pCGL824

FEATURES OF THE SEQUENCE
from 562 to 567 AAGGAG ribosome-binding site (S)
from 579 to 2108 coding sequence (S)
   from 579 to 668 secreted protein signal peptide (S)
   from 2188 to 2333 hairpin structure transcription terminator signal (S)
ASSOCIATED BIOLOGICAL ACTIVITY: precursor of the protein which constitutes the external surface layer of the wall and of the extracellular antigen PS2 of Corynebacterium melassecola and of Brevibacterium lactofermentum.

```
GAATTCCTGTGAATTAGCCGGTTTAGTACTTTTCAGGGGTGTCTATTCTTAC        52

CAGATCGTCAAGTTGTGGGTAGAGTCACCTGAATATTAATTGCACCGCACGG       104

GTGATATATGCTTATTTGCTCAAGTAGTTCGAGGTTAAGTGTATTTTAGGTG       156

AACAAATTTCAGCTTCGGGTAGAAGACTTTCTATGCGCTTCAGAGCTTCTAT       208

TAGGAAATCTGACACCACTTGATTAAATAGCCTACCCCCGAATTGGGGGATG       260

GGTGATTTTTTGCTGTGAAGGTAGTTTTGATGCATATGACCTGCGTTTATAA       312

AGAAATGTAAACGTGATCAGATCGATATAAAAGAAACAGTTTGTACTCAGGT       364

TTGAAGCATTTTCTCCGATTCGCCTGGCAAAAATCTCAATTGTCGCTTACAG       416

TTTTTCTCAACGACAGGCTGCTAAGCTGCTAGTTCGGTGGCCTAGTGAGTGG       468

CGTTTACTTGGATAAAAGTAATCCCATGTCGTGATCAGCCATTTTGGGTTGT       520

TTCCATAGCAATCCAAAGGTTTCGTCTTTCGATACCTATTCAAGGAGCCTTC       572

GCCTCT ATG TTT AAC AAC CGT ATC CGC ACT GCA GCT CTT         611
       Met Phe Asn Asn Arg Ile Arg Thr Ala Ala Leu

GCT GGT GCA ATC GCA ATC TCC ACC GCA GCT TCC GGC GTT         650
Ala Gly Ala Ile Ala Ile Ser Thr Ala Ala Ser Gly Val

GCT ATC CCA GCA TTC GCT CAG GAG ACC AAC CCA ACT TTC         689
Ala Ile Pro Ala Phe Ala Gln Glu Thr Asn Pro Thr Phe

AAC ATC ACC AAC GGC TTC AAC GAT GCT GAT GGA TCC ACC         728
Asn Ile Thr Asn Gly Phe Asn Asp Ala Asp Gly Ser Thr

ATC CAG CCA GTT GGC CCT GTT AAC CAC ACC GAG GAA ACC         767
Ile Gln Pro Val Gly Pro Val Asn His Thr Glu Glu Thr

CTC CGC GAC CTG ACT GAC TCC ACC GGC GCT TAC CTG GAA         806
Leu Arg Asp Leu Thr Asp Ser Thr Gly Ala Tyr Leu Glu

GAG TTC CAG AAC GGC ACC GTT GAG GAA ATC GTT GAA GCA         845
Glu Phe Gln Asn Gly Thr Val Glu Glu Ile Val Glu Ala

TAC CTG CAG GTT CAG GCT TCC GCA GAC GGA TTC GAT CCT         884
```

-continued

```
                Tyr Leu Gln Val Gln Ala Ser Ala Asp Gly Phe Asp Pro

TCT GAG CAG GCT GCT TAC GAG GCT TTC GAG GCT GCT CGC              923
Ser Glu Gln Ala Ala Tyr Glu Ala Phe Glu Ala Ala Arg

GTC CGT GCA TCC CAG GAG CTC GCA GCT TCC GCT GAG ACC              962
Val Arg Ala Ser Gln Glu Leu Ala Ala Ser Ala Glu Thr

ATC ACC AAG ACC CGC GAG TCC GTT GCT TAC GCA CTC AAG             1001
Ile Thr Lys Thr Arg Glu Ser Val Ala Tyr Ala Leu Lys

GTT GAC CAG GAA GCT ACC GCT GCT TTC GAG GCA TAC CGC             1040
Val Asp Gln Glu Ala Thr Ala Ala Phe Glu Ala Tyr Arg

AAC GCA CTT CGC GAT GCA GCT ATC TCT ATC AAC CCA GAT             1079
Asn Ala Leu Arg Asp Ala Ala Ile Ser Ile Asn Pro Asp

GGC TCT ATC AAC CCA GAT ACC TCT ATC AAC CTA CTG ATC             1118
Gly Ser Ile Asn Pro Asp Thr Ser Ile Asn Leu Leu Ile

GAT GCT GCT AAC GCT GCT AAC CGC ACC GAT CGT GCA GAG             1157
Asp Ala Ala Asn Ala Ala Asn Arg Thr Asp Arg Ala Glu

ATC GAG GAT TAC GCT CAC CTT TAC ACC CAG ACC GAT ATT             1196
Ile Glu Asp Tyr Ala His Leu Tyr Thr Gln Thr Asp Ile

GCT CTT GAA ACT CCA CAG CTT GCA TAC GCT TTC CAG GAC             1235
Ala Leu Glu Thr Pro Gln Leu Ala Tyr Ala Phe Gln Asp

CTG AAG GCT CTT CAG GCT GAG GTC GAC GCA GAC TTC GAG             1274
Leu Lys Ala Leu Gln Ala Glu Val Asp Ala Asp Phe Glu

TGG TTG GGC GAG TTC GGA ATC GAC CAG GAA GAC GGT AAC             1313
Trp Leu Gly Glu Phe Gly Ile Asp Gln Glu Asp Gly Asn

TAC GTT CAG CGC TAC CAC CTC CCT GCT GTA GAG GCA CTC             1352
Tyr Val Gln Arg Tyr His Leu Pro Ala Val Glu Ala Leu

AAG GCT GAG GTC GAC GCT CGC GTC GCA GCA ATT GAG CCA             1391
Lys Ala Glu Val Asp Ala Arg Val Ala Ala Ile Glu Pro

CTT CGT GCA GAC TCC ATC GCT AAG AAC CTT GAG GCG CAG             1430
Leu Arg Ala Asp Ser Ile Ala Lys Asn Leu Glu Ala Gln

AAG TCT GAC GTT CTG GTT CGC CAG CTC TTC CTC GAG CGT             1469
Lys Ser Asp Val Leu Val Arg Gln Leu Phe Leu Glu Arg

GCA ACC GCA CAG CGC GAC ACC CTG CGT GTT GTA GAG GCG             1508
Ala Thr Ala Gln Arg Asp Thr Leu Arg Val Val Glu Ala

ATC TTC TCT ACC TCT GCT CGT TAC GTT GAA CTC TAC GAG             1547
Ile Phe Ser Thr Ser Ala Arg Tyr Val Glu Leu Tyr Glu

AAC GTC GAG AAC GTT AAC GTT GAG AAC AAG ACC CTT CGC             1586
Asn Val Glu Asn Val Asn Val Glu Asn Lys Thr Leu Arg

CAG CAC TAC TCT GCG CTG ATC CCT AAC CTC TTC ATC GCA             1625
Gln His Tyr Ser Ala Leu Ile Pro Asn Leu Phe Ile Ala

GCA GTT GCA AAC ATC AGC GAG CTC AAC GCT GCA GAT GCT             1664
Ala Val Ala Asn Ile Ser Glu Leu Asn Ala Ala Asp Ala

GAA GCA GCA GCT TAC TAC CTC CAC TGG GAC ACC GAC CTC             1703
Glu Ala Ala Ala Tyr Tyr Leu His Trp Asp Thr Asp Leu

GCA ACC AAC GAT GAG GAC GAA GCT TAC TAC AAG GCT AAG             1742
Ala Thr Asn Asp Glu Asp Glu Ala Tyr Tyr Lys Ala Lys

CTC GAC TTC GCT ATC GAG ACC TAC GCA AAG ATC CTG TTC             1781
Leu Asp Phe Ala Ile Glu Thr Tyr Ala Lys Ile Leu Phe

AAC GGT GAA GTT TGG CAG GAG CCA CTG GCT TAC GTC CAG             1820
Asn Gly Glu Val Trp Gln Glu Pro Leu Ala Tyr Val Gln

AAC CTG GAT GCA GGC GCA CGT CAG GAA GCA GCT GAC CGT             1859
Asn Leu Asp Ala Gly Ala Arg Gln Glu Ala Ala Asp Arg

GAG GCA GCT CGC GCA GCT GAC GAA GCT TAC CGC GCT GAG             1898
Glu Ala Ala Arg Ala Ala Asp Glu Ala Tyr Arg Ala Glu

CAG CTC CGC ATC GCT CAG GAA GCA GCT GAC GCT CAG AAG             1937
Gln Leu Arg Ile Ala Gln Glu Ala Ala Asp Ala Gln Lys
```

-continued

```
Gln Leu Arg Ile Ala Gln Glu Ala Ala Asp Ala Gln Lys

GCT ATC GCT GAG GCG CTT GCT AAG GAA GCA GAA GGC AAC        1976
Ala Ile Ala Glu Ala Leu Ala Lys Glu Ala Glu Gly Asn

AAC GAC AAC TCC TCC GAC AAC ACG GAG ACC GGT TCT TCT        2015
Asn Asp Asn Ser Ser Asp Asn Thr Glu Thr Gly Ser Ser

GAC ATC GGA TCC TGG GGA CCT TTC GCA GCA ATT GCA GCT        2054
Asp Ile Gly Ser Trp Gly Pro Phe Ala Ala Ile Ala Ala

ATC ATC GCA GCA ATC GCA GCT ATC TTC CCA TTC CTC TCC        2093
Ile Ile Ala Ala Ile Ala Ala Ile Phe Pro Phe Leu Ser

GGT ATC GTT AAG TTC TAA TTTCGAACCGAGATAGCTAAAAGTTAAA       2139
Gly Ile Val Lys Phe

CCACCTCCTTTCTTGCGGGAGGTGGTTTTTCCCTTGGCTAACAGCACCAAAA       2191

GAAAAGCCACCTCCTTGATCTCAAGGAGGTGGCTTATCTTTTATTTACTGGG       2243

GAGCCGGAGGTTGGCGTCGATAAGCAAAAATCTTTTGCTTTTAAGGGAACGT       2295

GATAATCGGCTTAATGACTCGCCACTGGCGGAATCCGCAAAGGCATCATTGA       2347

TTTGTTCCAGCGGGTAAGTGCGCACGAGCTTCTCGATCGGGAACTTGCCCTG       2399

GCGCCACAAATGAACCAGGCGAGGGATGAAATCCTGAGGGACGGCGTCGCCC       2451

TCAATGATGGTCTGGAACTTCCAACCACGGACCAGTGACGCGCCAACCTCGA       2503

AGGTAGCTTCCGTGCCAGGGGCAGGGGCGCCGACGAGACCGACGGTACCGTT       2555

GATCGCCAAGGAATCGGCTGCTTGCCTGGTCACGGCCACGACACCAGTTGTA       2607

TCGAGAGCGAATTGCACACCATCGCCGGTCAGTTCCTTGATTTTCTCCGCAG       2659

GATCCTCATCCTTGGAGTTGATCGTGTGGGTAGCTCCGAGCTC               2702
```

SEQ ID NO: 5
SEQUENCE TYPE: Nucleotide and corresponding protein
SEQUENCE LENGTH: 2160 base pairs
STRANDEDNESS: double strand with a single strand representation in the 5'–3' direction
TOPOLOGY: linear
MOLECULE TYPE: genomic DNA
ORIGINAL SOURCE
ORGANISM: Corynebacterium melassecola
STRAIN: ATCC17965
IMMEDIATE EXPERIMENTAL SOURCE: pCGL315, pCGL313, pCGL310
FEATURES OF THE SEQUENCE from 251 to 266 TGGTCATATCTGTGCG promoter site recognized by the factor sigma 60 and regulated by ammonium (S)
from 437 to 442 TTCACA promoter signal region –35 (S)
from 466 to 471 TAGGAT promoter signal region –10 (S)
from 558 to 572 GGGAACGAGGAAATC ribosome-binding site (S)
from 573 to 1913 coding sequence (S)
from 1937 to 1977 hairpin structure rho-independent transcription terminator signal (S)
ASSOCIATED BIOLOGICAL ACTIVITY: NADPH-dependent glutamate dehydrogenase activity which migrates in denaturing gel as a 48300d polypeptide.

```
GCTAGCCTCGGGAGCTCTAGGAGATTGTGAAAAACGGGTCAAATTTCTCCGA       52

TGCAGCGCCTATAAAAGTCGTACCAATTCCATTTGAGGGTGCTCAAGTGTGG      104

CCAGGTTATATAACCAGTCAGTCAACTGGTCTCATTCGCTGGTCGGATGAAT      156

TTAATTAAAGAAGAGACTTCATGCAGTTACCGCGCGTTTTGGCGATACACAA      208

TTGATAAACCTAAAGAAATTTTCAAACAATTTTAATTCTTTGTGGTCATATC      260

TGTGCGACACTGCCATAATTGAACGTGAGCATTTACCAGCCTAAATGCCCGC      312

AGTGAGTTAAGTCTCAAAGCAAGAAGTTGCTCTTTAGGGCATCCGTAGTTTA      364

AAACTATTAACCGTTAGGTATGACAAGCCGGTTGATGTGAACGCAGTTTTTA      416

AAAGTTTCAGGATCAGATTTTTCACAGGCATTTTGCTCCAGCAAACGCCTAG      468

GATGTACATGGTGCCCTCAATGGGAACCACCAACATCACTAAATGGCCCAGA      520

TACACACTTTAAAATCGTGCGCGCATGCAGCCGAGATGGGAACGAGGAAATC      572
```

```
ATG ACA GTT GAT GAG CAG GTC TCT AAC TAT TAC GAC ATG      611
met thr val asp glu gln val ser asn tyr tyr asp met CTT CTG AAG CGC AAT GCT GGC GAG CCT GAA TTT CAC CAG      650
leu leu lys arg asn ala gly glu pro glu phe his gln GCA GTG GCA GAG GTT TTG GAA TCT TTG AAG ATC GTC CTG      689
ala val ala glu val leu glu ser leu lys ile val leu GAA AAG GAC CCT CAT TAC GCT GAT TAC GGT CTC ATC CAG      728
glu lys asp pro his tyr ala asp tyr gly leu ile gln CGC CTG TGC GAG CCT GAG CGT CAG CTC ATC TTC CGT GTG      767
arg leu cys glu pro glu arg gln leu ile phe arg val CCT TGG GTT GAT GAC CAG GGC CAG GTC CAC GTC AAC CGT      806
pro trp val asp asp gln gly gln val his val asn arg GGT TTC CGC GTG CAG TTC AAC TCT GCA CTT GGA CCA TAC      845
gly phe arg val gln phe asn ser ala leu gly pro tyr AAG GGC GGC CTG CGC TTC CAC CCA TCT GTA AAC CTG GGC      884
lys gly gly leu arg phe his pro ser val asn leu gly ATT GTG AAG TTC CTG GGC TTT GAG CAG ATC TTT AAA AAC      923
ile val lys phe leu gly phe glu gln ile phe lys asn TCC CTA ACC GGC CTG CCA ATC GGT GGT GGC AAG GGT GGA      962
ser leu thr gly leu pro ile gly gly gly lys gly gly TCC GAC TTC GAC CCT AAG GGC AAG TCC GAT CTG GAA ATC     1001
ser asp phe asp pro lys gly lys ser asp leu glu ile ATG CGT TTC TGC CAG TCC TTC ATG ACC GAG CTG CAC CGC     1040
met arg phe cys gln ser phe met thr glu leu his arg CAC ATC GGT GAG TAC CGC GAC GTT CCT GCA GGT GAC ATC     1079
his ile gly glu tyr arg asp val pro ala gly asp ile GGA GTT GGT GGC CGC GAG ATC GGT TAC CTG TTT GGC CAC     1118
gly val gly gly arg glu ile gly tyr leu phe gly his TAC CGT CGC ATG GCC AAC CAG CAC GAG TCC GGC GTT TTG     1157
tyr arg arg met ala asn gln his glu ser gly val leu ACC GGT AAG GGC CTG ACC TGG GGT GGA TCC CTG GTC CGC     1196
thr gly lys gly leu thr trp gly gly ser leu val arg ACC GAG GCA ACT GGC TAC GGC TGC GTT TAC TTC GTG AGT     1235
thr glu ala thr gly tyr gly cys val tyr phe val ser GAA ATG ATC AAG GCT AAG GGC GAG AGC ATC AGC GGC CAG     1274
glu met ile lys ala lys gly glu ser ile ser gly gln AAG ATC ATC GTT TCC GGT TCC GGC AAC GTA GCA ACC TAC     1313
lys ile ile val ser gly ser gly asn val ala thr tyr GCG ATT GAA AAG GCT CAG GAA CTC GGC GCA ACC GTT ATT     1352
ala ile glu lys ala gln glu leu gly ala thr val ile GGT TTC TCC GAT TCC AGC GGT TGG GTT CAT ACC CCT AAT     1391
gly phe ser asp ser ser gly trp val his thr pro asn GGC GTT GAC GTG GCT AAG CTC CGC GAA ATC AAG GAA GTT     1430
gly val asp val ala lys leu arg glu ile lys glu val CGC CGC GCA CGC GTA TCC GTG TAC GCC GAC GAA GTT GAA     1469
arg arg ala arg val ser val tyr ala asp glu val glu GGC GCA ACC TAC CAC ACC GAC GGG TCC ATC TGG GAT CTC     1508
gly ala thr tyr his thr asp gly ser ile trp asp leu AAG TGC GAT ATC GCT CTT CCT TGT GCA ACT CAG AAC GAG     1547
lys cys asp ile ala leu pro cys ala thr gln asn glu CTC AAC GGT GAG AAC GCT AAG ACT CTT GCA GAC AAC GGC     1586
leu asn gly glu asn ala lys thr leu ala asp asn gly TGC CGT TTC GTT GCT GAA GGC GCG AAC ATG CCT TCC ACC     1625
cys arg phe val ala glu gly ala asn met pro ser thr
```

-continued

```
CCA GAG GCT GTT GAG GTC TTC CGT GAG CGC GAC ATC CGC    1664
pro glu ala val glu val phe arg glu arg asp ile arg TTC GGA CCA GGC AAG GCA GCT AAC GCT GGT GGC GTT GCA    1703
phe gly pro gly lys ala ala asn ala gly gly val ala ACC TCC GCT CTG GAG ATG CAG CAG AAC GCT TCG CGC GAT    1742
thr ser ala leu glu met gln gln asn ala ser arg asp TCC TGG AGC TTC GAG TAC ACC GAC GAG CGC CTC CAG GTG    1781
ser trp ser phe glu tyr thr asp glu arg leu gln val ATC ATG AAG AAC ATC TTC AAG ACC TGT GCA GAG ACC GCA    1820
ile met lys asn ile phe lys thr cys ala glu thr ala GCA GAG TAT GGA CAC GAG AAC GAT TAC GTT GTC GGC GCT    1859
ala glu tyr gly his glu asn asp tyr val val gly ala AAC ATT GCT GGC TTC AAG AAG GTA GCT GAC GCG ATG CTG    1898
asn ile ala gly phe lys lys val ala asp ala met leu GCA CAG GGC GTC ATC TAA GACCCCTGCACTTTACTTAAACCCCTGA   1944
ala gln gly val ile OCH

TCCGCGTTAAGGATCAGGGATTTTTGATTTCTTCCAGGTCAATTATCCGATC   1996

CACATGGGTTAATGCAGCTGTGCGGTGCGCAATGATGATCACCGTGGTGTCT   2048

TTAAGCGTGGCCAGAGTCTGGGAAAGATCCGCTTGATTGAGCGCATCTTGGT   2100

GGCTGGTGGCTTCATCGACAATCAGTACCTGAGGGGTGCGTGCCAAAGCACG   2152

CGCCAGGCAGAGCCGTTGTTGCTGTCCGCCAGATAGGC                2190
```

REPLACEMENT SHEET

ISA/EP

As Legends to the Figures

FIG. 8:
  A=p: promoter of csp1
  s: putative csp1 signal sequence
  m: first 30 amino acids of mature PS1

FIG. 9:
  A=p: promoter of csp1
  s: putative csp1 signal sequence
  m: first 30 amino acids of mature PS1

Sequence detail from 5' to 3' (SEQ ID NO: 27)

ACACCGCATTTCGTTCCATCAAGGCTAAAGCTCAGGCTAAGCGCCGTTCCC

TCTGGATTGCAGCAGGCGCTGTCCCAACCGCAATTGCGTTGACTATGTCCC

TGGCACCTATGGCTTCGGCTCAGTCCAGCAACCTTTCCTCTGATGCCGTAG

TTGGCAGCATCGCGCAGGGCGTCACCGATGGCCTGACTGACTACCTGAAG

CCTCGCGTCGAAGACCTGCAGCCCAATTCCATGGCAATGGCCGGCCTGTCG

ACCCCGGCAAACACTGTGTCAGCGGCAGGTGTGCCTTTTAACACAAAATAC

CCCTATGGTCCTACTTCTATTGCCGATAATCAGTCGGAAGTAACTGCAATG

CTCAAAGCAGAATGGGAAGACTGGAAGAGCAAGAGAATTACCTCGAACGGT

GCAGGAGGATA

FIG. 10:
  A=p: promoter of csp1
  s: putative csp1 signal sequence
  m: first 30 amino acids of mature PS1

Sequence detail from 5' to 3' (SEQ ID NO: 28)

CCTTTCCTCTGATGCCGTAGTTGGCAGCATCGCGCAGGGCGTCACCGATGG

CCTGACTGACTACCTGAAGCCTCGCGTCGAAGACCTGCAGCCCAATTCCAT

GGCACAGAAGGCACAGAAGGCACAGAAGGCACAGAAGGCACAGAAGGCACA

GAAGGCACAGAAGGCACAGAAGGCACAGAAGGCACAGAAGGCAATGGCCGG

CCTGTCGACCCCGGCAAACACTGTGTCAGCGGCAGGTGTG

FIG. 11:
  A=p: promoter of csp1
  s: putative csp1 signal sequence
  m: first 30 amino acids of mature PS1

Sequence detail from 5' to 3' (SEQ ID NO: 29)

CCTTTCCTCTGATGCCGTAGTTGGCAGCATCGCGCAGGGCGTCACCGATGG

CCTGACTGACTACCTGAAGCCTCGCGTCGAAGACCTGCAGCCCAATTCCAT

GGCACAGGCACAGGCTCAGGCCCAGGCACAGGCCCAGGCGCAGGCCCAGGC

CCAGGCTCAGGCACAGGCGCAGGCGCAGGCACAGGCACAGGCTCAGGCGCA

GGCTCAGGCTCAGGCAATGGCCGGCCTGTCGACCCCGGCAAACACTGTGTC

AGCGGCAGGT

FIG. 22:

Polylinker1: 0.001/SacII.BstXI.NotI.XbaI.

Polylinker2: 1.531/ClaI.SalI.AatI.MluI.NcoI.BglII.XhoI.StuI.PstI. SmaI.BamHI-.SpeI.

Polylinker3: 1.561/XbaI.NotI.SacII.BstXI.

We claim:

1. A DNA cassette for expression and secretion of a given amino acid, polypeptide or protein in a host strain of corynebacterium, comprising:

a sequence which encodes the amino acid, polypeptide or protein, and a region of chromosomal or plasmid DNA;

wherein the sequence is situated in the region of chromosomal or plasmid DNA such that the sequence is located 3' of at least a sequence encoding the signal sequence of the protein PS1 or PS2 or a point mutation thereof, said at least a sequence ensuring the secretion of the amino acid, polypeptide or protein after translation when the DNA cassette is incorporated into the host strain of corynebacterium.

2. The DNA cassette of claim 1, wherein the host strain of corynebacterium is a strain of the genus Brevibacterium.

3. A DNA cassette for expression and secretion of a given amino acid, polypeptide or protein in a host strain of corynebacterium, comprising:

a first functional DNA sequence which encodes the elements necessary for expression in the host strain of corynebacterium, a second DNA sequence which encodes the amino acid, polypeptide or protein to be expressed in the host strain of corynebacterium, and a third DNA sequence inserted between the first and second DNA sequences which encodes the elements of PS1 or PS2 necessary for secretion of the amino acid, polypeptide or protein in the host strain of corynebacterium.

4. The DNA cassette of claim 3, wherein the first functional DNA sequence contains a promoter and a ribosome-binding site.

5. The DNA cassette of claim 3, wherein the DNA cassette is carried on an autonomously replicating plasmid containing a replication origin which is functional in the host strain of corynebacterium.

6. The DNA cassette of claim 3, wherein the DNA cassette further comprises elements of DNA causing integration of the cassette into the chromosome of the host strain of corynebacterium.

7. The DNA cassette of claim 3, wherein the elements necessary for secretion encoded by the third DNA sequence comprise all or a functional portion of the signal sequence of PS1 or PS2.

8. The DNA cassette of claim 3, further comprising a marker gene, a translational stop sequence at the end of the second DNA sequence, and a transcriptional stop sequence at the end of the second DNA sequence.

9. The DNA cassette of claim 3, wherein the DNA cassette comprises a csp1 or csp2 gene and the second sequence is inserted into the csp1 or csp2 gene in phase and downstream of the elements of PS1 or PS2 necessary for secretion of the amino acid, polypeptide or protein in the host strain of corynebacterium.

10. The DNA cassette of claim 3, wherein the elements encoded by the third sequence encode truncated PS1 or PS2.

11. The DNA cassette of claim 3, wherein the second sequence encodes a polypeptide.

12. The DNA cassette of claim 3, wherein the second sequence contains all or a portion of the gdhA gene corresponding to FIG. 17, SEQ ID NO: 5.

13. The DNA cassette of claim 3, wherein the elements encoded by the first DNA sequence are selected from the group consisting of the expression elements of csp1, csp2 and gdhA.

14. The DNA cassette of claim 3, wherein the elements encoded by the first DNA sequence are selected such that expression is dependent on the concentration of salts, metabolites or sugars.

15. A bacterial strain transformed with the DNA cassette of claim 3.

16. The DNA cassette of claim 3, wherein the third DNA sequence encodes a leader sequence of PS1 or PS2.

17. The DNA cassette of claim 4, wherein the promoter is selected from the group consisting of csp1, csp2 and gdhA promoters.

18. The DNA cassette of claim 8, wherein the marker gene is celA.

19. The DNA cassette of claim 8, wherein the marker gene is lacZ.

20. The DNA cassette of claim 11, wherein the polypeptide contains at the COOH-terminal position a positively- or negatively-charged amino acid.

21. The strain of claim 15, wherein the strain is a corynebacterium strain.

22. The DNA cassette of claim 20, wherein the positively- or negatively-charged amino acid is one that can be removed by a specific carboxypeptidase.

23. The strain of claim 21, wherein the corynebacterium strain belongs to the genus Brevibacterium.

24. A method for producing an amino acid, polypeptide or protein, comprising:

culturing in a culture medium the transformed strain of corynebacterium of claim 21, and optionally separating the amino acid, polypeptide or protein from the culture medium and/or the transformed bacterial strain after culturing.

25. The strain of claim 23, wherein the Brevibacterium is *Brevibacterium lactofermentum*.

26. The method of claim 24, wherein a surface-active agent is used during the separation of the amino acid, polypeptide, or protein from the culture medium and/or the transformed bacterial strain.

27. A purified protein consisting of PS1 or PS2.

28. An antibody directed against PS1 or PS2.

* * * * *